United States Patent
Lee et al.

(10) Patent No.: US 9,412,954 B2
(45) Date of Patent: Aug. 9, 2016

(54) HETEROCYCLIC COMPOUND AND ORGANIC ELECTRONIC ELEMENT CONTAINING SAME

(71) Applicant: LG CHEM, LTD., Seoul (KR)

(72) Inventors: Sangbin Lee, Daejeon (KR); Dong Hoon Lee, Daejeon (KR); Hoyong Lee, Daejeon (KR); Kongkyeom Kim, Daejeon (KR); Jungi Jang, Daejeon (KR); Sung Kil Jung, Daejeon (KR); Changhwan Shin, Daejeon (KR); Hyungjin Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/355,165

(22) PCT Filed: May 13, 2013

(86) PCT No.: PCT/KR2013/004230
§ 371 (c)(1),
(2) Date: Apr. 29, 2014

(87) PCT Pub. No.: WO2014/010823
PCT Pub. Date: Jan. 16, 2014

(65) Prior Publication Data
US 2014/0299192 A1    Oct. 9, 2014

(30) Foreign Application Priority Data

Jul. 13, 2012   (KR) .................. 10-2012-0076493
May 13, 2013  (KR) .................. 10-2013-0053866

(51) Int. Cl.
H01L 51/00   (2006.01)
H01L 51/05   (2006.01)
(Continued)

(52) U.S. Cl.
CPC .......... H01L 51/0067 (2013.01); C07D 213/06 (2013.01); C07D 239/26 (2013.01);
(Continued)

(58) Field of Classification Search
CPC ............ H01L 51/0074; H01L 51/0073; H01L 51/0067; H01L 51/0052; H01L 51/5056; H01L 51/5072; H01L 51/5088; H01L 51/5092; H01L 51/0512; H01L 51/42
USPC ........................................... 136/263; 247/40
See application file for complete search history.

(56) References Cited

U.S. PATENT DOCUMENTS 6,057,048 A    5/2000   Hu et al.
6,352,791 B1   3/2002   Fink et al.
(Continued)

FOREIGN PATENT DOCUMENTS

CN    101381601 A  *  3/2009
CN    101412907 A     4/2009
(Continued)

OTHER PUBLICATIONS

Machine translation of CN 101381601A.*
(Continued)

*Primary Examiner* — Ling Choi
*Assistant Examiner* — Catherine S Branch
(74) *Attorney, Agent, or Firm* — Dentons US LLP

(57) ABSTRACT

The present disclosure provides a novel compound capable of greatly improving the lifetime, efficiency, electrochemical stability and thermal stability of an organic electronic device, and an organic electronic device including an organic compound layer containing the compound.

18 Claims, 1 Drawing Sheet

(51) Int. Cl.
  H01L 51/42      (2006.01)
  H01L 51/50      (2006.01)
  C07D 403/10     (2006.01)
  C09K 11/06      (2006.01)
  C07D 405/14     (2006.01)
  C07D 401/10     (2006.01)
  C07D 409/14     (2006.01)
  C07D 251/24     (2006.01)
  H05B 33/10      (2006.01)
  C07D 213/06     (2006.01)
  C07D 239/26     (2006.01)
  H01L 51/52      (2006.01)

(52) U.S. Cl.
  CPC ............ *C07D251/24* (2013.01); *C07D 401/10* (2013.01); *C07D 403/10* (2013.01); *C07D 405/14* (2013.01); *C07D 409/14* (2013.01); *C09K 11/06* (2013.01); *H01L 51/0052* (2013.01); *H01L 51/0058* (2013.01); *H01L 51/0073* (2013.01); *H01L 51/0074* (2013.01); *H01L 51/0512* (2013.01); *H01L 51/42* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0508* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5221* (2013.01); *Y02E 10/549* (2013.01)

(56) References Cited

U.S. PATENT DOCUMENTS

| | | | |
|---|---|---|---|
| 2004/0086745 A1 | 5/2004 | Iwakuma et al. | |
| 2007/0122652 A1 | 5/2007 | Hashimoto et al. | |
| 2008/0145699 A1 | 6/2008 | Yabe et al. | |
| 2008/0154040 A1 | 6/2008 | Kosuge et al. | |
| 2009/0017331 A1 | 1/2009 | Iwakuma et al. | |
| 2009/0066226 A1 | 3/2009 | Sugita et al. | |
| 2011/0227053 A1 | 9/2011 | Bae et al. | |
| 2011/0240983 A1 | 10/2011 | Sekiguchi et al. | |
| 2012/0001164 A1* | 1/2012 | Gao et al. | 257/40 |
| 2012/0098413 A1 | 4/2012 | Lin et al. | |
| 2012/0104941 A1 | 5/2012 | Jung et al. | |
| 2012/0228554 A1* | 9/2012 | Franz et al. | 252/500 |
| 2012/0273771 A1 | 11/2012 | Jung et al. | |
| 2013/0037788 A1 | 2/2013 | Kosuge et al. | |
| 2013/0087771 A1 | 4/2013 | Qiu et al. | |
| 2014/0203272 A1 | 7/2014 | Hong et al. | |

FOREIGN PATENT DOCUMENTS

| | | | |
|---|---|---|---|
| CN | 102471679 A | | 5/2012 |
| DE | 102009053664 A1 * | | 5/2011 |
| EP | 1695952 A1 | | 8/2006 |
| EP | 1829871 A1 | | 9/2007 |
| EP | 2060574 A1 | | 5/2009 |
| JP | 2004-281390 A | | 10/2004 |
| JP | 2005-302657 A | | 10/2005 |
| JP | 2006-016577 A | | 1/2006 |
| JP | 2006-124373 A | | 5/2006 |
| JP | 2006-225322 A | | 8/2006 |
| JP | 2006199679 A | | 8/2006 |
| JP | 200742973 A | | 2/2007 |
| JP | 2007-223928 A | | 9/2007 |
| JP | 2008-156316 A | | 7/2008 |
| JP | 200957326 A | | 3/2009 |
| JP | 2009-184987 | | 8/2009 |
| JP | 2010138121 A | | 6/2010 |
| JP | 2010254635 A | | 11/2010 |
| JP | 2011-035386 A | | 2/2011 |
| JP | 2011509247 A | | 3/2011 |
| JP | 2011225501 A | | 11/2011 |
| JP | 2012-017265 A | | 1/2012 |
| JP | 201233784 A | | 2/2012 |
| KR | 10-2012-0038032 | | 4/2012 |
| KR | 1020120116838 A | | 10/2012 |
| WO | 03/012890 | | 2/2003 |
| WO | 2006/035997 A1 | | 4/2006 |
| WO | 2006067976 A1 | | 6/2006 |
| WO | 2006114966 A1 | | 11/2006 |
| WO | 2009/008099 A1 | | 1/2009 |
| WO | 2009086028 A2 | | 7/2009 |
| WO | 2009/142870 A1 | | 11/2009 |
| WO | 2011-005060 | | 1/2011 |
| WO | 2011013959 A2 | | 2/2011 |
| WO | 2011057461 A1 | | 5/2011 |
| WO | 2011-081290 | | 7/2011 |
| WO | 2011157790 A1 | | 12/2011 |
| WO | 2013/068376 A1 | | 5/2013 |
| WO | 2013/129835 1 A | | 9/2013 |

OTHER PUBLICATIONS

Melzer et al., "Enlightened organic transistors," Nature Materials, vol. 9, Jun. 2010, pp. 470-472.*

Ma et al., "Organic light-emitting diodes based on new n-doped electron transport layer," Synth. Met., 158 (2008) 810-814.*

Annual Report Prog. Chem., Sect. A:Inorg. Chem., May 15, 2012, 108, 292-314.

Chinese Office Action with English translation dated Oct. 12, 2015 in Chinese Application No. 2013800347909 (13 pages total).

Lu, X., et al., "From supramolocular triangle to heteroleptic rhombus: a simple bridge can make a difference," CHem. Commun., 2012, 48, pp. 9873-9875.

El-Batal, H., et al., "Perylene-Based Bis-, Tetrakis-, and Hexakis(terpyridine) Ligands and Their Ruthenium(II)-Bis (terpyridine) Complexes: Synthesis and Photophysical Properties," Eur. J. Org. Chem., 2013, pp. 3640-3644.

Wang, Jin-Liang, et al., "Stoichiometric Self-Assembly of Shape-Persistent 2D Complexes: A Facile Route to a Symmetric Supramacromolecular Spoked Wheel," J. Am. Chem. Soc., 2011, 133, pp. 11450-11453.

Schultz, A., et al., "Stoichiometric Self-Assembly of Isomeric, Shape-Persistent Supramacromolecular Bowtie and Butterfly Structures," J. Am. Chem. Soc., 2012, 134, pp. 7672-7675.

Chow, H.S., et al., "Comformationally-locked metal-lomacrocycles—prototypes for a novel type of axial chirality," New J. Them., 2009, 33, pp. 376-385.

Pal, R. R., et al., "Optically Active Metallo-Supramolecular Polymers Derived from Chiral Bis-terpyridines," Org. Lett., 2009, vol. 11, No. 16, pp. 3562-3565.

Han, Fu-She, et al., "Synthesis of π-conjugated, pyridine ring functionalized bis-terpyridines with efficient green, blue, and purple emission," Tetrahedron 64, 2008, pp. 9108-9116.

Schultz, A., et al., "Stable, trinuclear Zn(II)- and Cd(II)-metal-locycles: TWIM-MS, photophysical properties, and nanofiber formation," Dalton Trans., 2012, 41, pp. 11573-11575.

* cited by examiner

HETEROCYCLIC COMPOUND AND ORGANIC ELECTRONIC ELEMENT CONTAINING SAME

TECHNICAL FIELD

The present disclosure relates to a novel heterocyclic compound and to an organic electronic device comprising the same.

This application is a 35 USC §371 National Stage entry of International Application No. PCT/KR2013/004230, filed on May 13, 2013, which claims the benefit of the filing date of Korean Patent Application No. 10-2012-0076493, filed with the Korean Intellectual Property Office on Jul. 13, 2012, the disclosure of which is incorporated herein in its entirety by reference. This application also claims the benefit of the filing date of Korean Patent Application No. 10-2013-0053866, filed with the Korean Intellectual Property Office on May 13, 2013, the disclosure of which is incorporated herein in its entirety by reference.

BACKGROUND ART

As used herein, the term "organic electronic device" refers to a device that requires the exchange of an electronic charge between an electrode and an organic material using holes and/or electrons. The organic electronic device can be largely classified according to its operational principle into two types as follows. One type is an electronic device having a configuration in which an exciton is formed in an organic material layer by the entry of photons into the device from an external light source, and is then separated into an electron and a hole, which are transferred to different electrodes as a current source (voltage source), and the other type is an electric device having a configuration in which a voltage or a current is applied to two or more electrodes to inject a hole and/or an electron into an organic semiconductor positioned at the interface between the electrodes, and the device is operated using the injected electron and hole.

Examples of the organic electronic device include an organic light-emitting device, an organic solar cell, an organic transistor and the like, all of which require a hole-injecting or hole-transporting material, an electron-injecting or electron-transporting material or a light emitting material to drive the device. Hereinafter, the organic light-emitting device will be mainly and specifically described, but in the above-mentioned organic electronic devices, the hole-injecting or hole-transporting material, the electron-injecting or electron-transporting material, or the light-emitting material injection functions according to a similar principle.

In general, the term "organic light-emitting phenomenon" refers to a phenomenon in which electric energy is converted to light energy using an organic material. The organic light-emitting device that uses the organic light-emitting phenomenon usually has a structure comprising an anode, a cathode and an organic material layer interposed therebetween. Herein, the organic layer often has a multilayer structure consisting of a plurality of layers made of different materials in order to increase the efficiency and stability of the organic light-emitting device. For example, the organic material layer may consist of a hole-injecting layer, a hole-transporting layer, a light-emitting layer, an electron-transporting layer, an electron-injecting layer and the like. In the organic-light emitting device having this structure, when a voltage is applied between two electrodes, holes from the anode and electrons from the cathode are injected into the organic material layer, and the injected holes and electrons are combined with each other to form excitons. When the excitons subsequently drop to the ground state, light is emitted.

The development of novel materials for organic light-emitting devices as described above has been continuously demanded, and the development of materials for other organic electronic devices as described above has also been demanded.

PRIOR ART DOCUMENTS

Patent Documents

International Patent Application Publication No. WO 2003/012890

DISCLOSURE

Technical Problem

Accordingly, it is an object of the present disclosure to provide a heterocyclic compound having a chemical structure, which, depending on the substituent groups thereof, may provide various functions required for an organic electronic device, and to provide an organic electronic device comprising the same.

Technical Solution

The present disclosure provides the compound represented by the following formula 1:

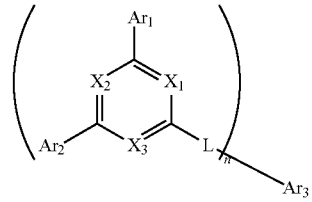

Formula 1 wherein
n is 2,
$X_1$ to $X_3$ are the same or different, and are each independently a trivalent heteroatom or CH, and at least one of $X_1$ to $X_3$ is a trivalent heteroatom,
$Ar_1$ and $Ar_2$ are the same or different, and are each independently a substituted or unsubstituted aryl group or heterocyclic group,
L is a substituted or unsubstituted arylene group, a substituted or unsubstituted alkenylene group, a substituted or unsubstituted fluorenylene group or a substituted or unsubstituted heterocyclic group having a heteroatom selected from O, N, S and P, and
$Ar_3$ is selected from the group consisting of a substituted or unsubstituted 1,3-phenyl group, a substituted or unsubstituted 1,2-phenyl group, a substituted or unsubstituted 9,10-phenanthryl group, a substituted or unsubstituted 2,7-phenanthryl group, a substituted or unsubstituted 1,8-phenanthryl group, a substituted or unsubstituted 3,6-dibenzothiophene group, a substituted or unsubstituted 3,6-dibenzofuran group, a substituted or unsubstituted 1,8-dibenzothiophene group, a substituted or unsubstituted 1,8-dibenzofuran group, a substituted or unsubstituted tetracenyl group, a substituted or unsubstituted chrysenyl group, a substituted or unsubstituted fluoranthene group, a substituted or unsubstituted xanthene group and a substituted or unsubstituted acenaphthyl group.

The present disclosure also provides an organic electronic device comprising a first electrode, a second electrode and one or more organic material layers interposed between the first electrode and the second electrode, wherein one or more of the organic material layers comprise the heterocyclic compound of formula 1.

Advantageous Effects

The novel compound according to the present invention may be used as a material for the organic material layer of organic electronic devices, including organic light-emitting devices. The use of the novel compound according to the present disclosure makes it possible to improve the efficiency of organic electronic devices, including organic light-emitting devices, lower the driving voltage of the devices and/or improve the lifetime characteristics of the devices.

MODE FOR INVENTION

Figure 1:
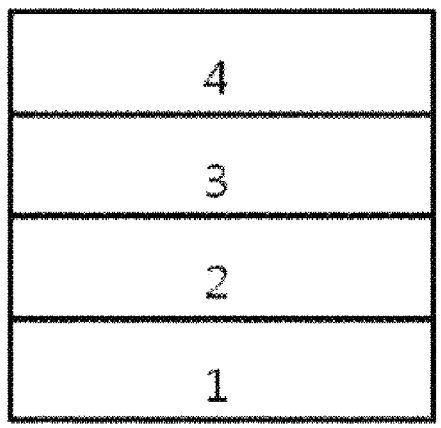
FIG. 1 shows an example of an organic light-emitting device consisting of a substrate 1, an anode 2, a light-emitting layer 3 and a cathode 4.

The present disclosure provides the compound represented by formula 1 above.

In the present disclosure, examples of the trivalent heteroatom include, but are not limited to, N and P.

In an embodiment of the present disclosure, the trivalent heteroatom is N.

In an embodiment of the present disclosure, $X_1$ to $X_3$ are the same or different, and are each independently N or CH, and at least one of $X_1$ to $X_3$ is N.

In an embodiment of the present disclosure, n is 2.

In an embodiment of the present disclosure, when n is 2, $X_1$ to $X_3$, $Ar_1$ to $Ar_3$ and L may be the same or different.

In an embodiment of the present disclosure, n is 2, and $Ar_3$ is selected from among the following structures:

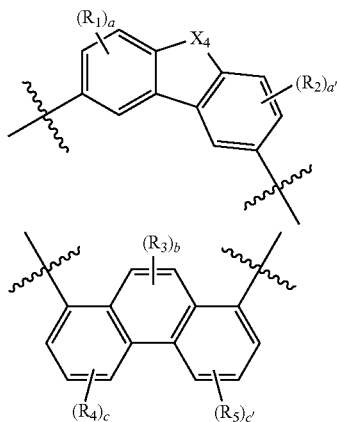

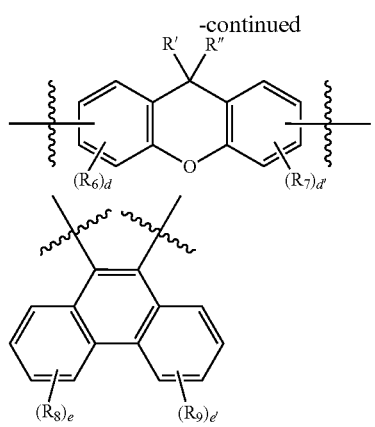

wherein a, a', c, c', d and d' are each an integer ranging from 1 to 3,
b are an integer ranging from 1 to 2,
e and e' are each an integer ranging from 1 to 4,
$X_4$ is S or O,
$R_1$ to $R_9$ are the same or different, and are each independently hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heterocyclic group containing at least one heteroatom selected from among N, O, S and P,
R' and R" are the same or different, and are each independently selected from the group consisting of hydrogen, deuterium, a halogen group, a nitrile group, a nitro group, hydroxyl group, substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, substituted or unsubstituted heteroarylamine group, a substituted or unsubstituted aryl group, a substituted or unsubstituted fluorenyl group, a substituted or unsubstituted carbazole group, and substituted or unsubstituted heterocyclic group containing at least one heteroatom selected from among N, O, S and P, or may form a condensed ring with an aliphatic, aromatic, aliphatic heterocyclic or aromatic heterocyclic ring or form a spiro linkage.

In the present disclosure,

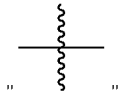

means a portion linked to other substituent groups. In an embodiment,

may be linked to L of formula 1.

In an embodiment of the present disclosure, $Ar_1$ and $Ar_2$ are the same or different, and are each independently a substituted or unsubstituted phenyl group, a substituted or unsubstituted naphthyl group or a substituted or unsubstituted pyridine group.

In another embodiment, L is a substituted or unsubstituted phenylene group.

Examples of the substituent groups will be described below, but are not limited thereto.

In the present disclosure, the alkyl group may be linear or branched, and the number of carbon atoms thereof is not specifically limited, but is preferably 1-50. Specific examples of the alkyl group include, but are not limited to, methyl, ethyl, propyl, isopropyl, butyl, t-butyl, pentyl, hexyl and heptyl groups.

In the present disclosure, the alkenyl group may be linear or branched, and the number of carbon atoms thereof is not specifically limited, but is preferably 2-50. Specific examples of the alkenyl group include, but are not limited to, aryl-substituted alkenyl groups, such as stylbenyl and styrenyl groups.

In the present disclosure, the alkoxy group may be linear or branched, and the number of carbon atoms thereof is not specifically limited, but is preferably 1-50.

The lengths of the alkyl, alkenyl and alkoxy groups in the compound do not influence the conjugation length of the compound, and merely influence a method for applying the compound to an organic electronic device, for example, a vacuum deposition method or a solution application method, and thus the numbers of carbon atoms of these groups are not specifically limited.

In the present disclosure, the cycloakyl group is not specifically limited, but preferably contains 3-60 carbon atoms. Preferred examples of the cycloalkyl group include cyclopentyl and cyclohexyl groups.

In the present disclosure, examples of the halogen group include fluorine, chlorine, bromine or iodine.

In the present disclosure, the fluorenyl group has a structure in which two cyclic organic compounds are linked to each other by one atom, and examples thereof include

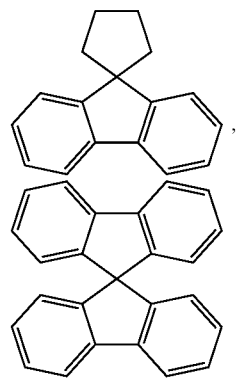

and the like.

In the present disclosure, the fluorenyl groups include an open fluorenyl group having a structure in which one of two cyclic compounds linked to each other by one atom is broken. Examples of the open fluorenyl group include

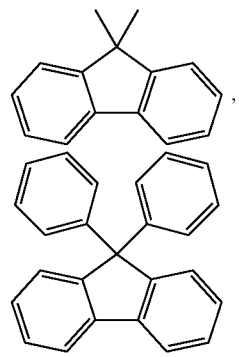

and the like.

In the present disclosure, the number of carbon atoms of the amine group is not specifically limited, but is preferably 1-50. Specific examples of the amine group include, but are not limited to, methylamine, dimethylamine, ethylamine, diethylamine, phenylamine, naphthylamine, biphenylamine, anthracenylamine, 9-methyl-anthracenylamine, diphenylamine, phenylnaphthylamine, ditolylamine, phenyltolylamine and triphenylamine groups.

In the present disclosure, examples of the arylamine group include a substituted or unsubstituted monoarylamine group, a substituted or unsubstituted diarylamine group or a substituted or unsubstituted triarylamine group. The aryl group of the arylamine group may be a monocyclic or polycyclic aryl group. The arylamine group containing two or more aryl groups may include a monocyclic aryl group, a polycyclic aryl group or both the monocyclic aryl group and the polycyclic aryl group.

Specific examples of the arylamine group include, but are not limited to, phenylamine, naphthylamine, biphenylamine, anthracenylamine, 3-methyl-phenylamine, 4-methyl-naphthylamine, 2-methyl-biphenylamine, 9-methyl-anthracenylamine, diphenylamine, phenylnaphthylamine, ditolylamine, phenyltolylamine, carbazole and triphenylamine groups.

In the present disclosure, the number of carbon atoms of each of the aryloxy, arylthioxy, arylsulfoxy and aralkylamine groups is not specifically limited, but is preferably 6-50. The aryl group of each of the aryloxy, arylthioxy, arylsulfoxy and aralkylamine groups is as defined above.

In the present disclosure, the alkyl group of each of the alkylthioxy, alkylsulfoxy, alkylamine and aralkylamine groups is as defined above.

In the present disclosure, the heteroaryl group of the heteroarylamine group may be selected from the above-described examples of the heterocyclic group.

In the present disclosure, the arylene, alkenylene, fluorenylene and heteroarylene groups are divalent aryl, alkenyl, fluorenyl and heteroaryl groups, respectively. These groups are as defined above for the aryl, alkenyl, fluorenyl and heteroaryl groups, except that they are divalent groups.

As used herein, the term "substituted or unsubstituted" means that it is unsubstituted or substituted with one or more substituents selected from the group consisting of deuterium, a halogen group, an alkyl group, an alkenyl group, an alkoxy group, a cycloalkyl group, a silyl group, an arylalkenyl group, an aryl group, an aryloxy group, an alkylthioxy group, an alkylsulfoxy group, an arylsulfoxy group, a boron group, an alkylamine group, an aralkylamine group, an arylamine group, a heteroaryl group, a carbazole group, an arylamine group, a fluorenyl group, a nitrile group, a nitro group, a hydroxyl group, a cyano group and a heterocyclic group containing at least one heteroatom selected from among N, O, S and P.

The present disclosure provides a novel heterocyclic compound represented by formula 1 above. This compound may be used for an organic material layer in an organic electronic device due to its structural specificity.

In an embodiment, $Ar_3$ is a substituted or unsubstituted 9,10-phenanthryl group, a substituted or unsubstituted 1,8-phenanthryl group, a substituted or unsubstituted 1,8-xanthene group, a substituted or unsubstituted 3,6-dibenzothiophene group or a substituted or unsubstituted 3,6-dibenzofuran group.

In an embodiment of the present disclosure, $Ar_3$ is a 3,6-dibenzothiophene group.

In the present disclosure, when $Ar_3$ is a 3,6-dibenzothiophene group, it has an excellent electron donor effect, and thus can increase the efficiency with which an electron is injected into and transported to a light-emitting layer. For this reason, the compound may have more excellent characteristics in terms of voltage and efficiency.

In another embodiment, $Ar_3$ is a 3,6-dibenzofuran group.

In the present disclosure, when $Ar_3$ is a 3,6-dibenzofuran group, it has an excellent electron donor effect, and thus can increase the efficiency with which an electron is injected into and transported to a light-emitting layer. For this reason, the compound may have more excellent characteristics in terms of voltage and efficiency.

In an embodiment of the present disclosure, $Ar_3$ is a 9,10-phenanthryl group.

In an embodiment of the present disclosure, $Ar_3$ is a 1,8-phenanthryl group.

In an embodiment of the present disclosure, $Ar_3$ is a 1,8-xanthene group.

In an embodiment of the present disclosure, $Ar_3$ is a 3,6-dibenzothiophene group substituted with a phenyl group.

In an embodiment of the present disclosure, $Ar_3$ is a 3,6-dibenzothiophene group substituted with an aryl group.

In an embodiment of the present disclosure, $Ar_3$ is a 3,6-dibenzofuran group substituted with an aryl group.

In an embodiment of the present disclosure, $Ar_3$ is a 3,6-dibenzofuran group substituted with a phenyl group.

In an embodiment of the present disclosure, $Ar_3$ is a 9,10-phenanthryl group substituted with an aryl group.

In an embodiment of the present disclosure, $Ar_3$ is a 9,10-phenanthryl group substituted with a phenyl group.

In an embodiment of the present disclosure, $Ar_3$ is a 1,8-phenanthryl group substituted with an aryl group.

In an embodiment of the present disclosure, $Ar_3$ is a 1,8-phenanthryl group substituted with a phenyl group.

In an embodiment of the present disclosure, $Ar_3$ is a 1,8-xanthene group substituted with an aryl group.

In an embodiment of the present disclosure, $Ar_3$ is a 1,8-xanthene group substituted with a phenyl group.

In an embodiment of the present disclosure, the compound represented by formula 1 is represented by any one of the following formulas 1-a, 1-b, 1-c, 1-d, 1-e and 1-f:

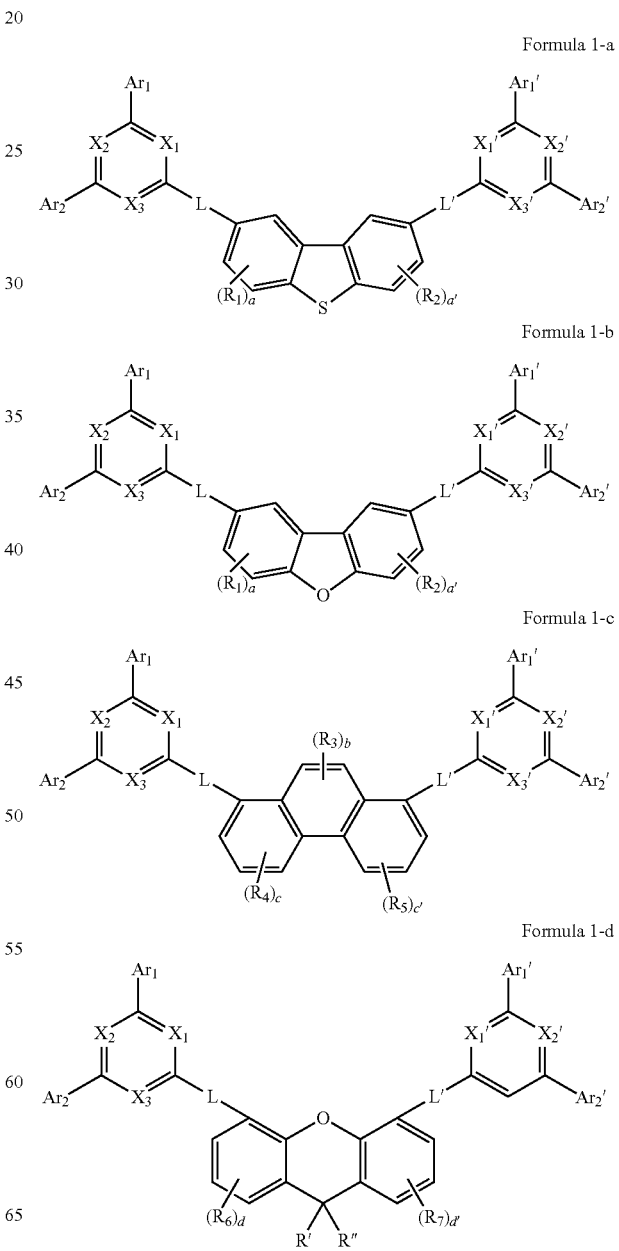

-continued

Formula 1-e

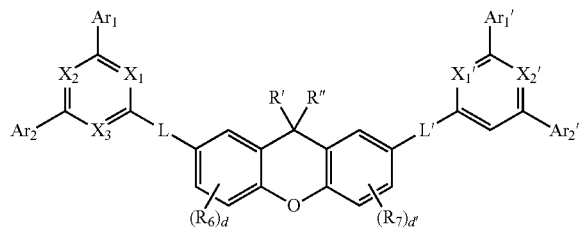

Formula 1-f

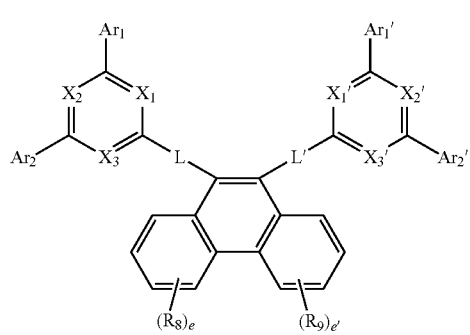

wherein $Ar_1$, $Ar_2$, L and $X_1$ to $X_3$ are as defined in formula 1 above, $Ar_1'$, $Ar_2'$, L' and $X_1'$ to $X_3'$ are the same as the definitions of $Ar_1$, $Ar_2$, L and $X_1$ to $X_3$, respectively, and $R_1$ to $R_7$, R', R", a, a', b, c, c', d, d', e and e' are as defined above.

In an embodiment, at least one of $X_1$ to $X_3$ in formula 1 may be a trivalent heteroatom.

Specifically, at least one of $X_1$ to $X_3$ may be N or P.

In an embodiment of the present disclosure, $X_1$ to $X_3$ may all be N.

In an embodiment of the present disclosure, $X_1$ may be N, and $X_2$ and $X_3$ may be CH.

In an embodiment of the present disclosure, $X_2$ may be N, and $X_1$ and $X_3$ may be CH.

In an embodiment of the present disclosure, $X_3$ may be N, and $X_1$ and $X_2$ may be CH.

In an embodiment of the present disclosure, $X_1$ and $X_2$ may be N. In this case, $X_3$ is CH.

In an embodiment of the present disclosure, $X_1$ and $X_3$ may be N. In this case, $X_2$ is CH.

In an embodiment of the present disclosure, $X_2$ and $X_3$ may be N. In this case, $X_1$ is CH.

In an embodiment of the present disclosure, when n in formula 1 is 2, the structures linked to $Ar_3$ may be the same or different.

In another embodiment of the present disclosure, $Ar_1$ and $Ar_2$ in formula 1 may be a substituted or unsubstituted aryl or heteroaryl group.

Specifically, $Ar_1$ and $Ar_2$ may be the same or different, and may be each independently a substituted or unsubstituted phenyl group, a substituted or unsubstituted biphenyl group, a substituted or unsubstituted pyridyl group or a substituted or unsubstituted naphthyl group.

In an embodiment of the present disclosure, $Ar_1$ and $Ar_2$ are the same or different, and may be each independently an alkyl-substituted phenyl group, an alkoxy-substituted phenyl group, a halogen-substituted phenyl group or a trifluoro-substituted phenyl group.

In an embodiment of the present disclosure, $Ar_1$ and $Ar_2$ are the same or different, and may be each independently an alkyl-substituted biphenyl group, an alkoxy-substituted biphenyl group, a halogen-substituted biphenyl group or a trifluoro-substituted biphenyl group.

In an embodiment of the present disclosure, $Ar_1$ and $Ar_2$ are the same or different, and may be each independently an alkyl-substituted pyridyl group, an alkoxy-substituted pyridyl group, a halogen-substituted pyridyl group or a trifluoro-substituted pyridyl group.

In an embodiment of the present disclosure, $Ar_1$ and $Ar_2$ are the same or different, and may be each independently an alkyl-substituted phenyl group, an alkoxy-substituted naphthyl group, a halogen-substituted naphthyl group or a trifluoro-substituted naphthyl group.

In an embodiment of the present disclosure, $Ar_1$ and $Ar_2$ are the same or different, and may be each independently a methyl-substituted phenyl group, a methoxy-substituted phenyl group, a fluoro-substituted phenyl group or a trifluoro-substituted phenyl group.

In an embodiment of the present disclosure, $Ar_1$ and $Ar_2$ are the same or different, and may be each independently

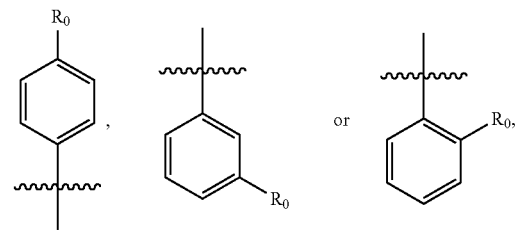

wherein $R_0$ may be selected from the group consisting of alkyl, alkoxy, halogen and trifluoro groups.

In an embodiment of the present disclosure, $Ar_1$ and $Ar_2$ are the same or different, and may be each independently a methyl-substituted biphenyl group, a methoxy-substituted biphenyl group, a fluoro-substituted biphenyl group or a trifluoro-substituted biphenyl group.

In an embodiment of the present disclosure, $Ar_1$ and $Ar_2$ are the same or different, and may be each independently a methyl-substituted pyridyl group, a methoxy-substituted pyridyl group, a fluoro-substituted pyridyl group or a trifluoro-substituted pyridyl group.

In an embodiment of the present disclosure, $Ar_1$ and $Ar_2$ are the same or different, and may be each independently a methyl-substituted naphthyl group, a methoxy-substituted naphthyl group, a fluoro-substituted naphthyl group or a trifluoro-substituted naphthyl group.

In an embodiment of the present disclosure, $Ar_1$ and $Ar_2$ are the same or different, and may be each independently a phenyl, biphenyl, pyridyl or naphthyl group.

In an embodiment of the present disclosure, $Ar_1$ and $Ar_2$ are the same or different, and may be each independently In an embodiment of the present disclosure, Ar₁ and Ar₂ are the same or different, and may be each independently

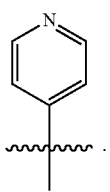

In an embodiment of the present disclosure, Ar₁ and Ar₂ are the same or different, and may be each independently

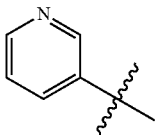

In an embodiment of the present disclosure, Ar₁ and Ar₂ are the same or different, and may be each independently

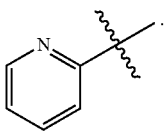

In an embodiment of the present disclosure, Ar₁ and Ar₂ are the same or different, and may be each independently

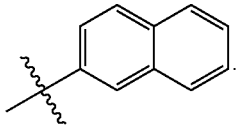

In an embodiment of the present disclosure, Ar₁ and Ar₂ are the same or different, and may be each independently

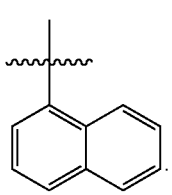 [SMILES: *c1cccc2ccccc12]

In an embodiment of the present disclosure, Ar₁ and Ar₂ are the same or different, and may be each independently

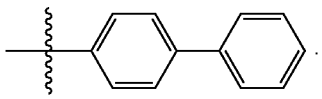 [SMILES: *c1ccc(-c2ccccc2)cc1]

In the present disclosure,

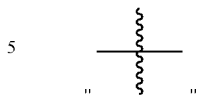

means that Ar₁ or Ar₂ is linked to the heterocyclic ring including X₁ to X₃ of formula 1.

In another embodiment of the present disclosure, L may be a substituted or unsubstituted arylene group, a substituted or unsubstituted alkenylene group, a substituted or unsubstituted fluorenylene group or a substituted or unsubstituted heteroarylene having a heteroatom selected from among O, N, S and P.

Specifically, L may be a substituted or unsubstituted phenylene group, a substituted or unsubstituted naphthalene group, a substituted or unsubstituted fluorenylene group, a substituted or unsubstituted pyridylene group or a substituted or unsubstituted biphenylene group.

In an embodiment of the present disclosure, L may be a phenylene, naphthalene, fluorenylene, pyridylene or biphenylene group.

In an embodiment of the present disclosure, L may be a phenylene group. Specifically, L may be

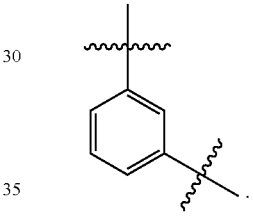

In another embodiment, L may be

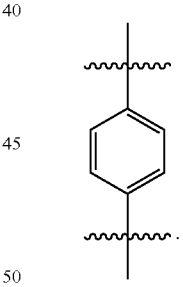

Herein,

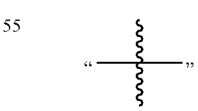

means that L is linked to either the heterocyclic ring including X₁ to X₃ of formula 1 or Ar₃.

In an embodiment of the present disclosure, the compound represented by formula 1 is any one of the following compounds 1-a-1 to 1-a-16, 2-a-1 to 2-a-8,1-b-1 to 1-b-16, 2-b-1 to 2-b-8,1-c-1 to 1-c-12, 2-c-1 to 2-c-8,1-d-1 to 1-d-10, 2-d-1 to 2-d-8,1-e-1 to 1-e-10, 2-e-1 to 2-e-8,1-f-1 to 1-f-12 and 2-f-1 to 2-f-8.

In an embodiment of the present disclosure, the compound represented by formula 1-a is any one of the following compounds 1-a-1 to 1-a-16 and 2-a-1 to 2-a-8:
Compound 1-a-1
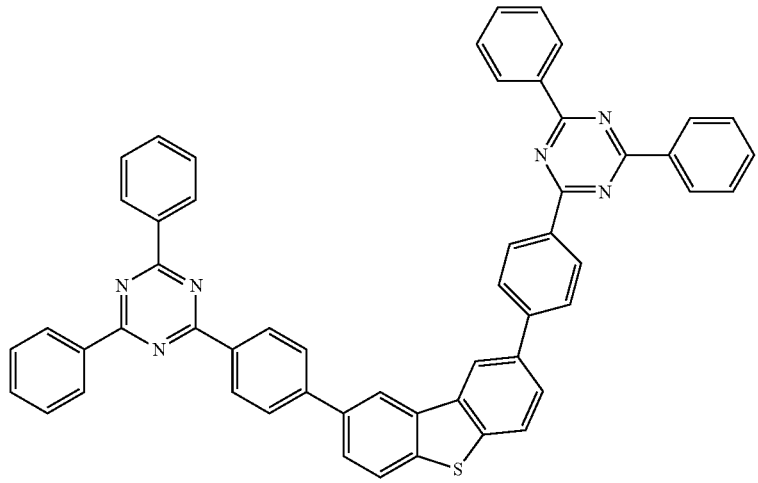
Compound 1-a-2
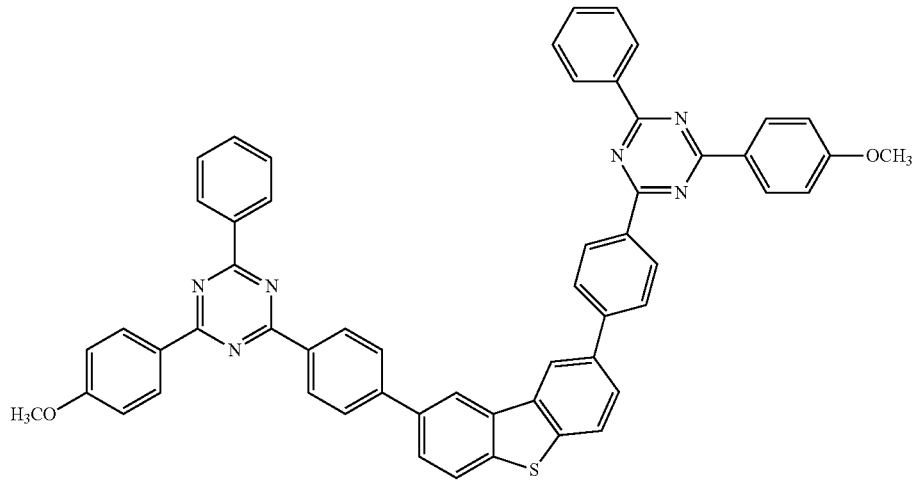
Compound 1-a-3
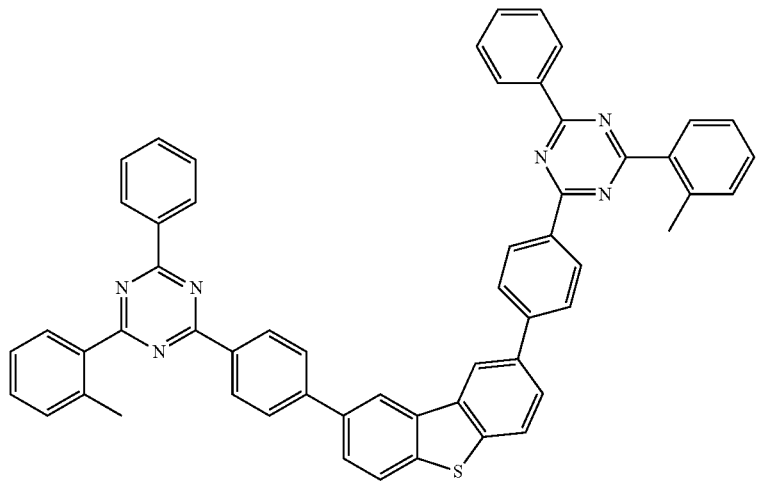

-continued
Compound 1-a-4
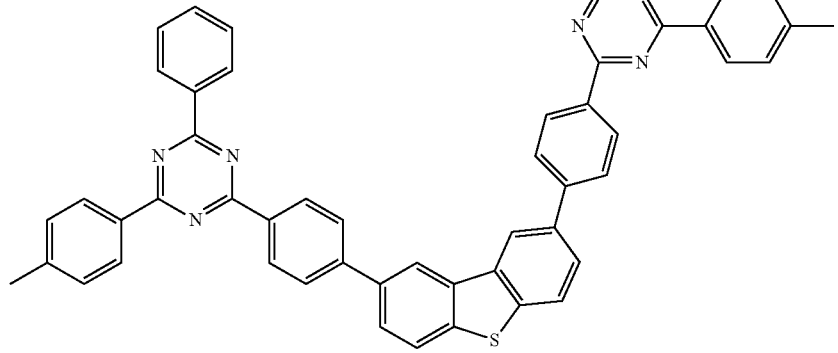
Compound 1-a-5
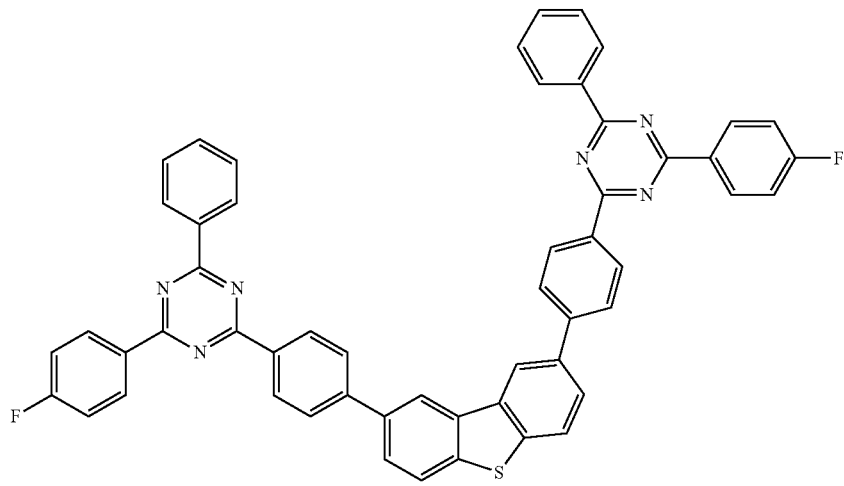
Compound 1-a-6
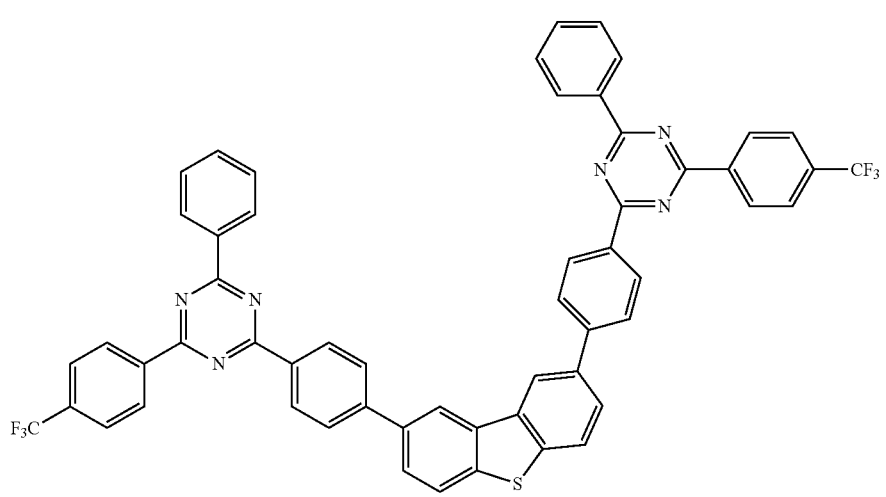

Compound 1-a-7
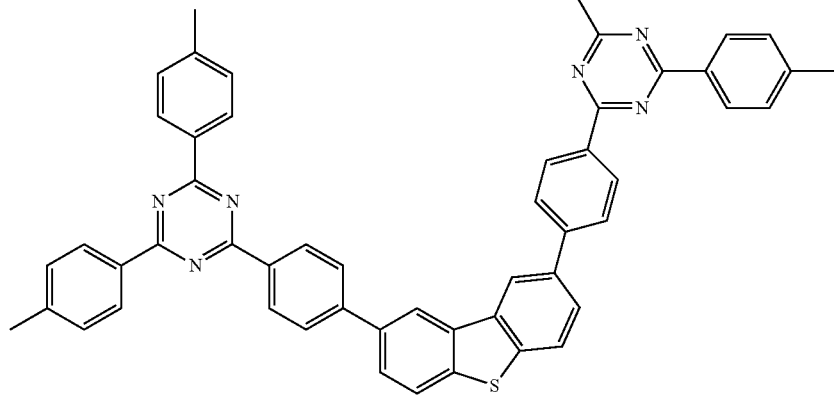
Compound 1-a-8
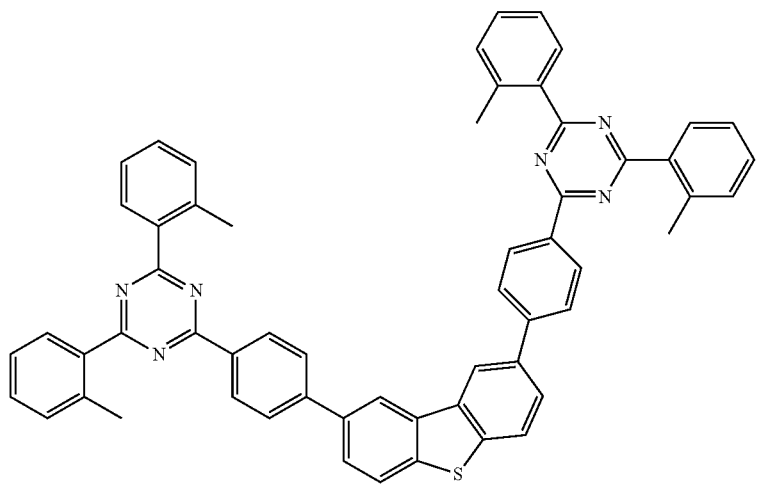
Compound 1-a-9
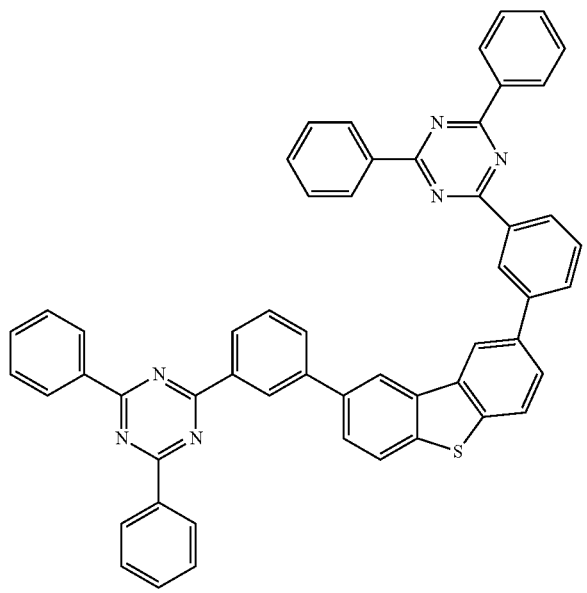

Compound 1-a-10
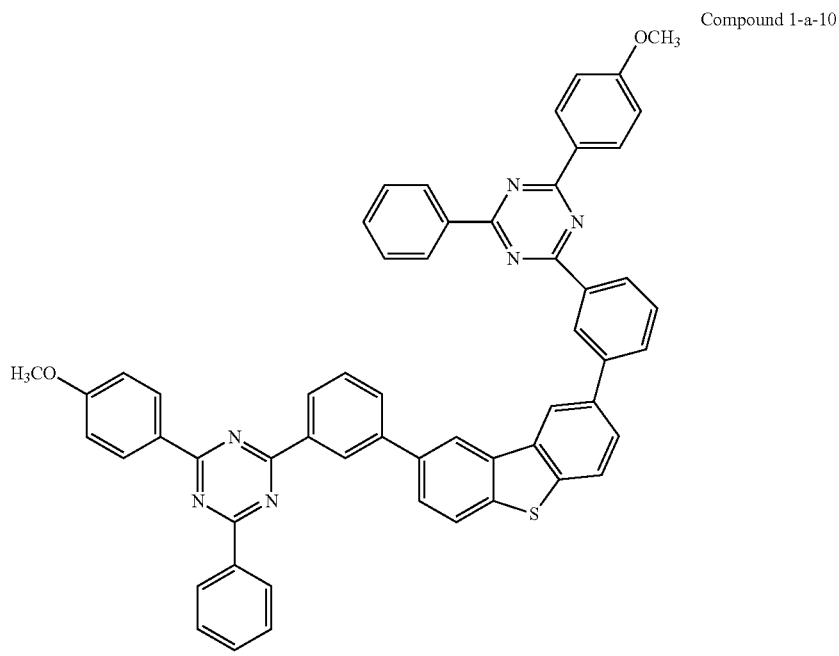
Compound 1-a-11
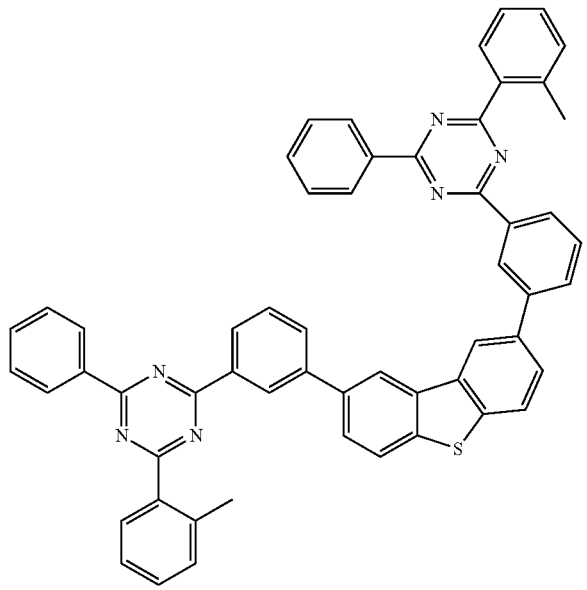

Compound 1-a-12
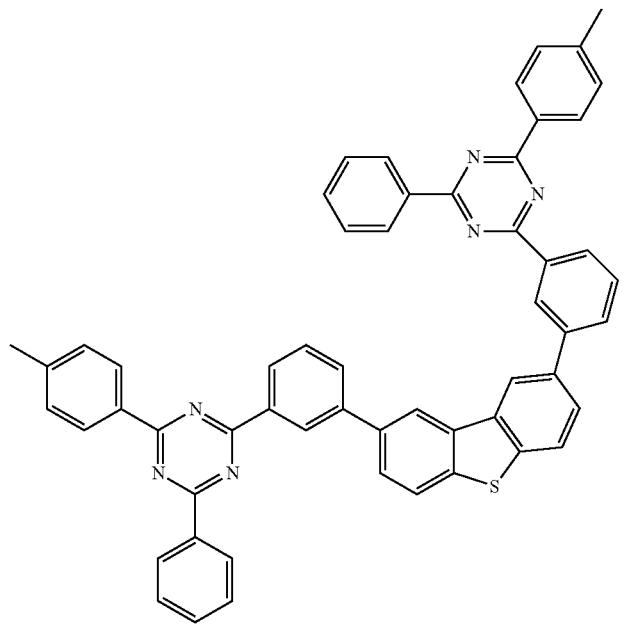
Compound 1-a-13
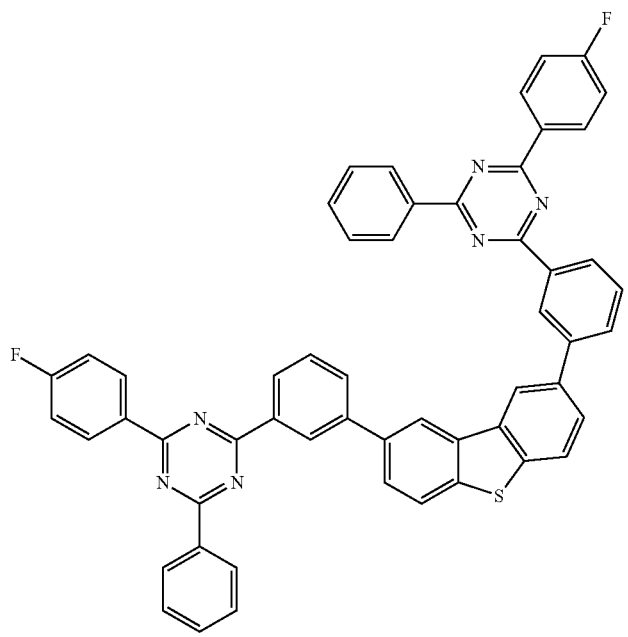

-continued
Compound 1-a-14
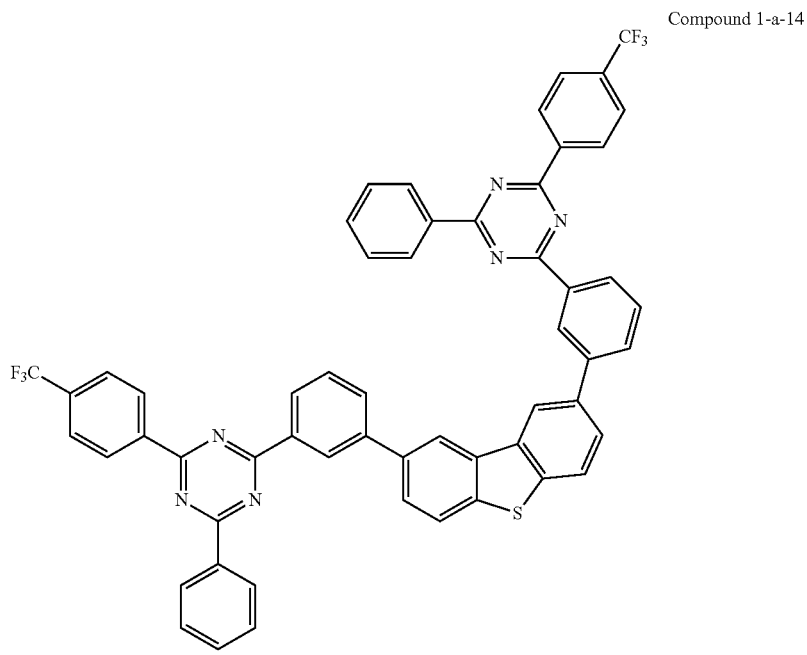
Compound 1-a-15
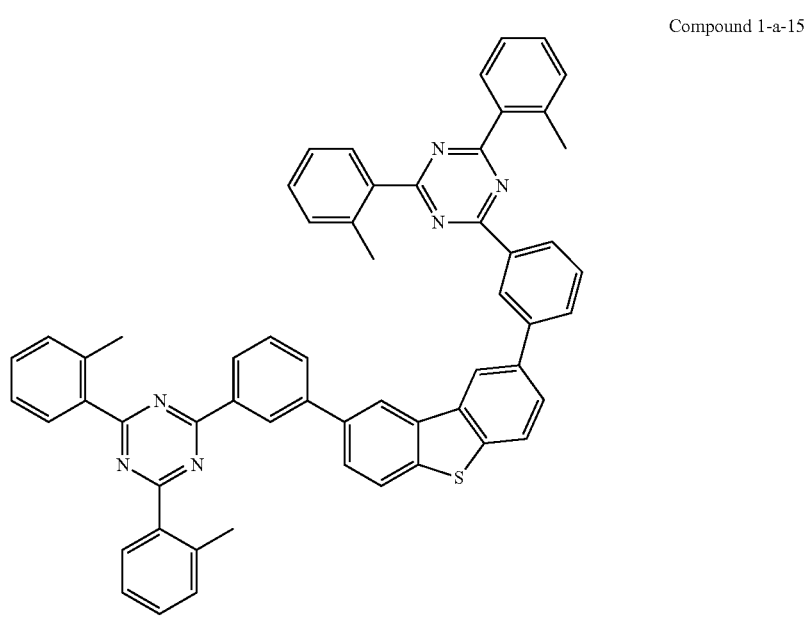

Compound 1-a-16
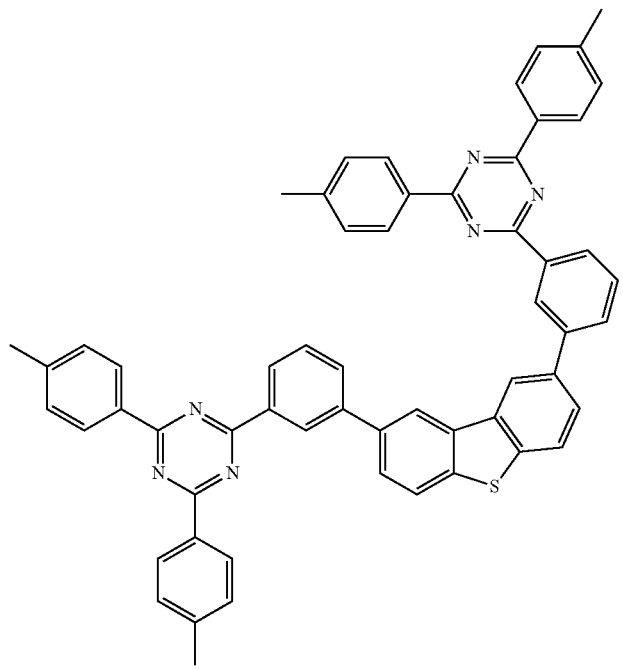
Compound 2-a-1
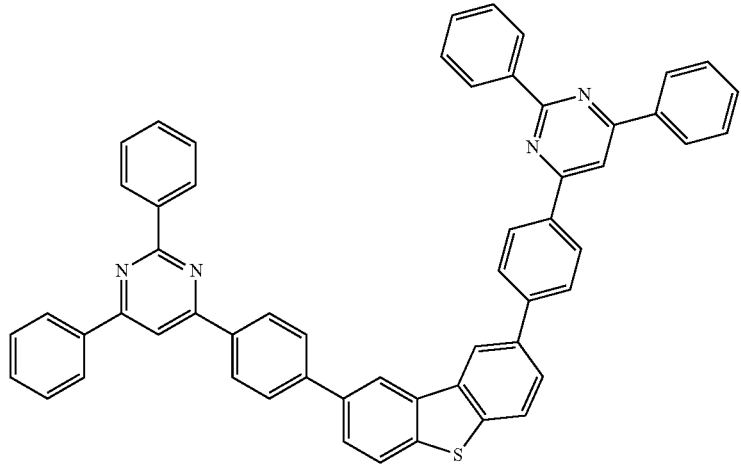
Compound 2-a-2
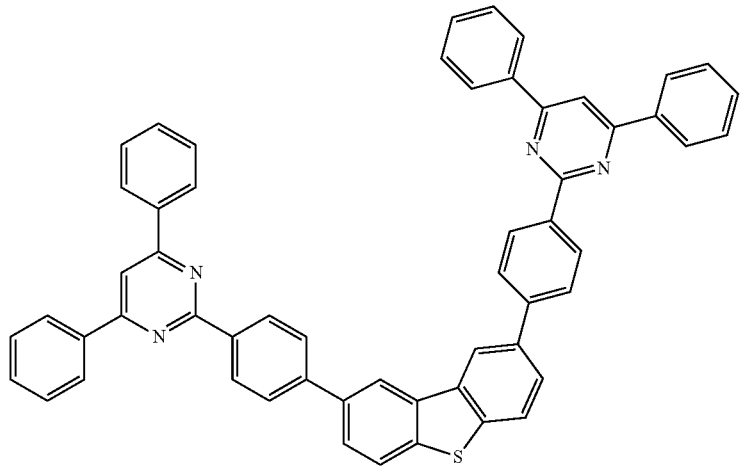

Compound 2-a-3
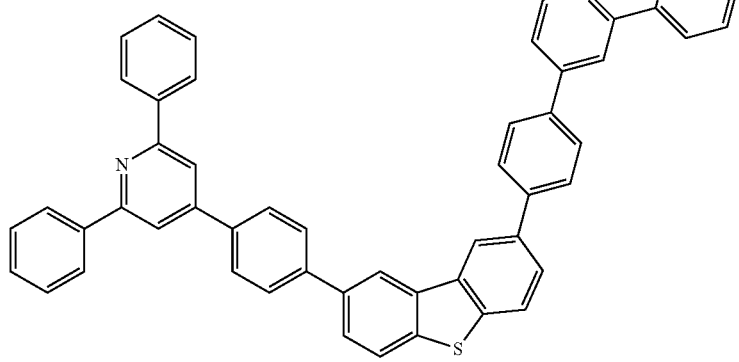
Compound 2-a-4
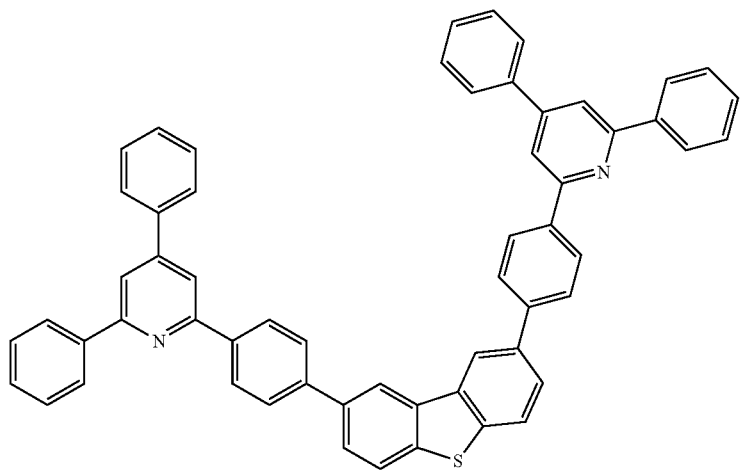
Compound 2-a-5
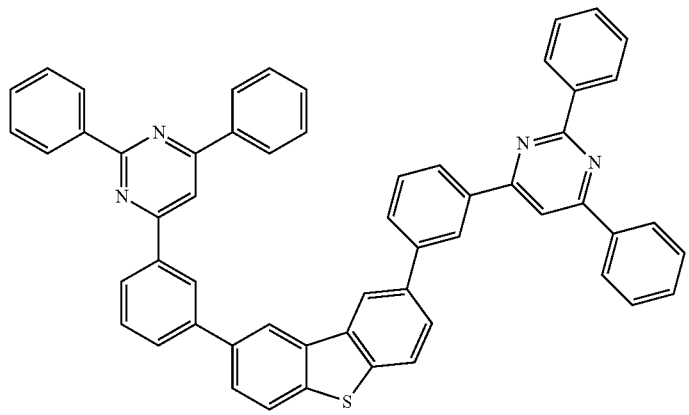

Compound 2-a-6
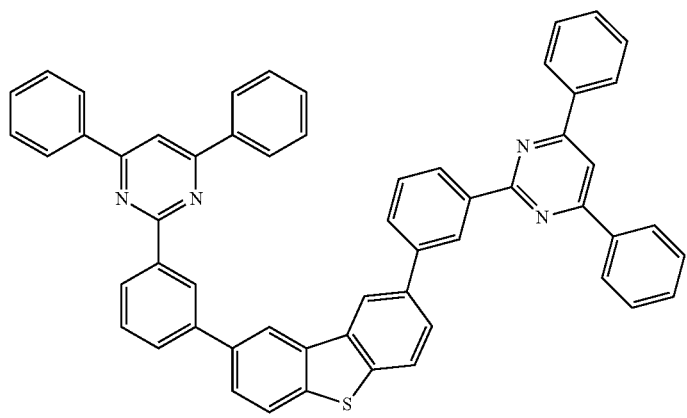
Compound 2-a-7
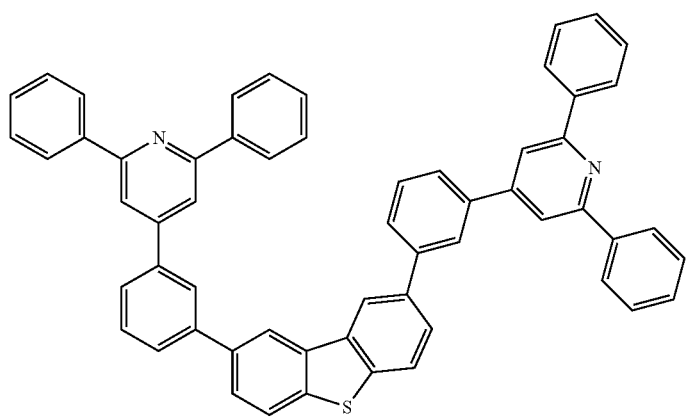
Compound 2-a-8
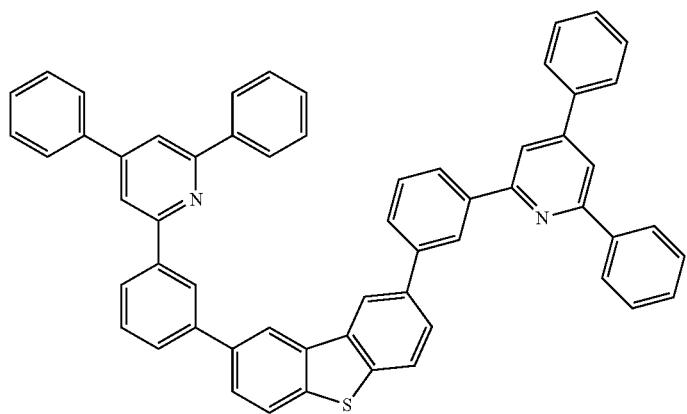

In an embodiment of the present disclosure, the compound represented by formula 1-b is any one of the following compounds 1-b-1 to 1-b-16 and 2-b-1 to 2-b-8:
Compound 1-b-1
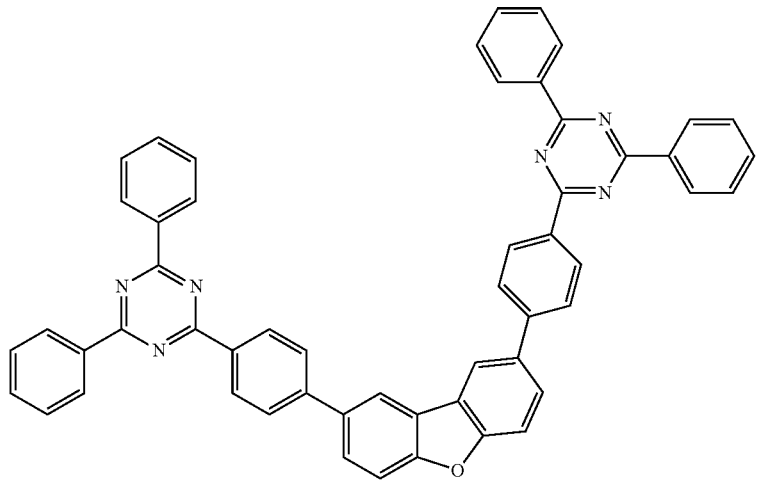
Compound 1-b-2
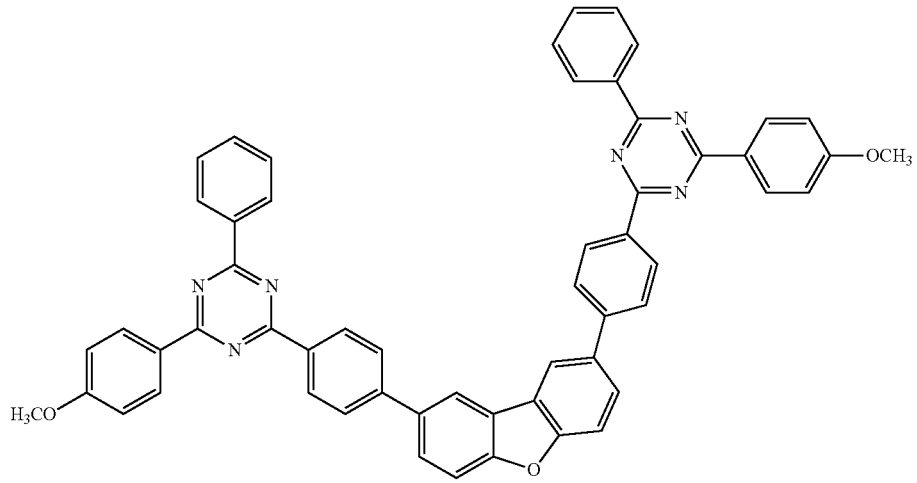
Compound 1-b-3
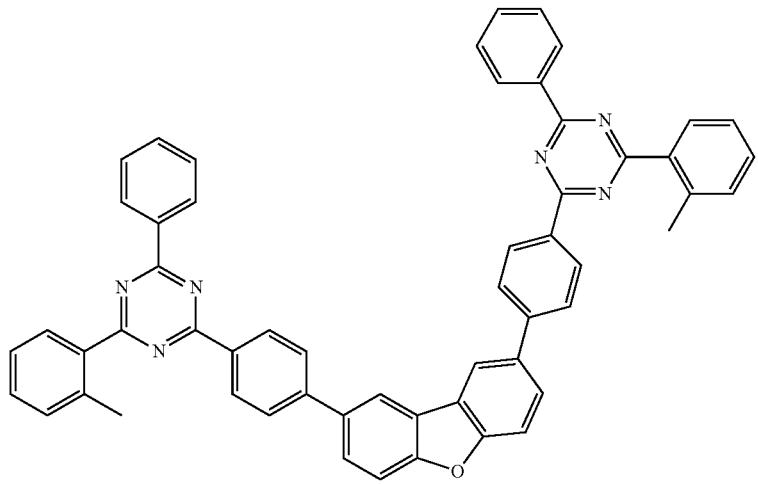

Compound 1-b-4
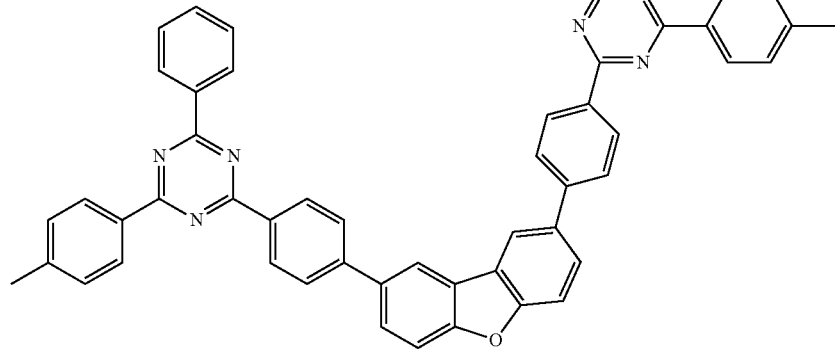
Compound 1-b-5
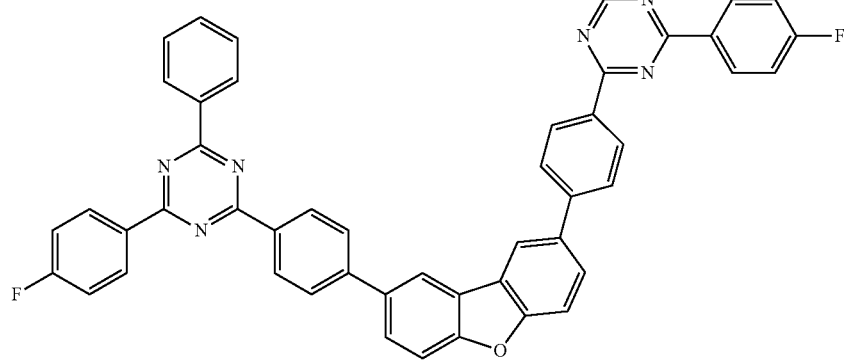
Compound 1-b-6
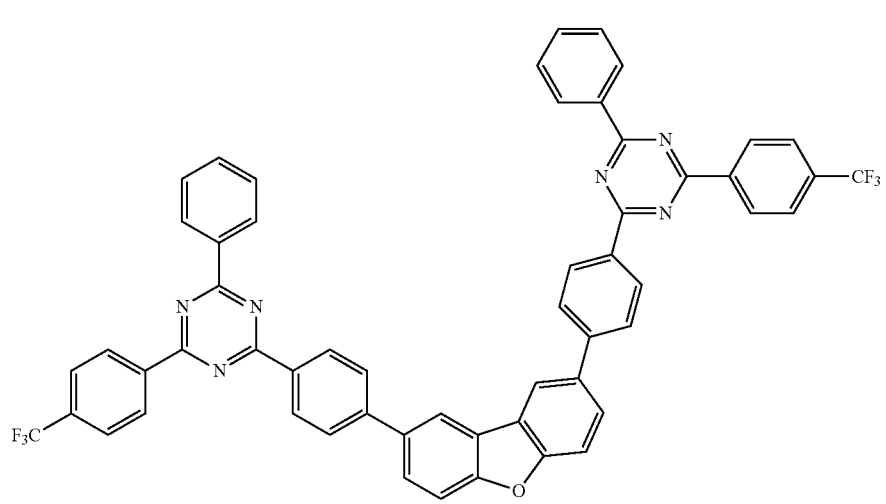

Compound 1-b-7
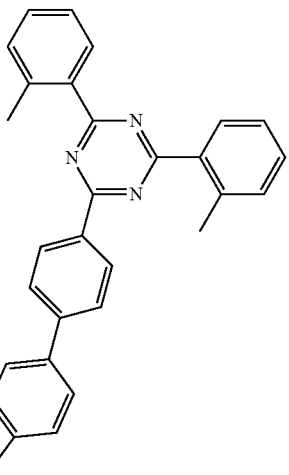
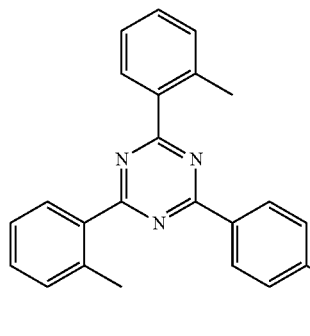
Compound 1-b-8
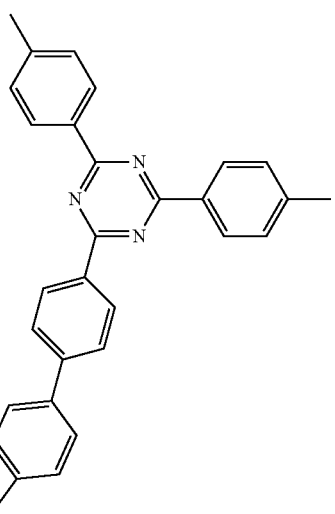
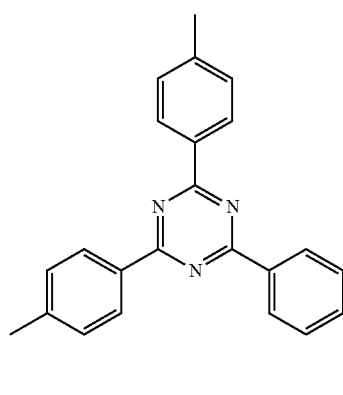
Compound 1-b-9
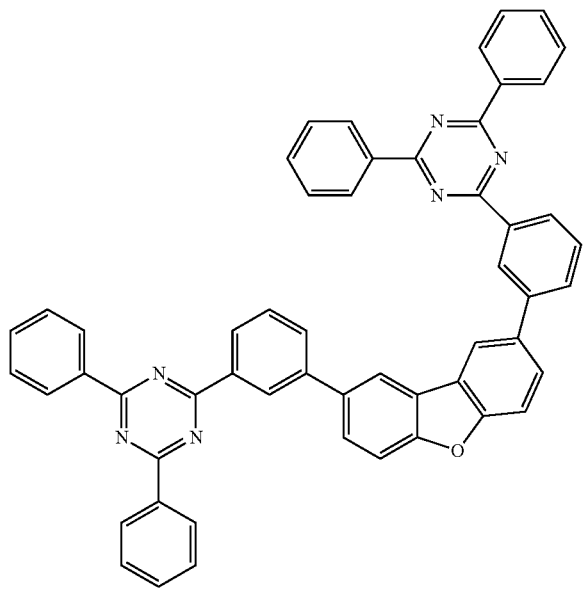

Compound 1-b-10
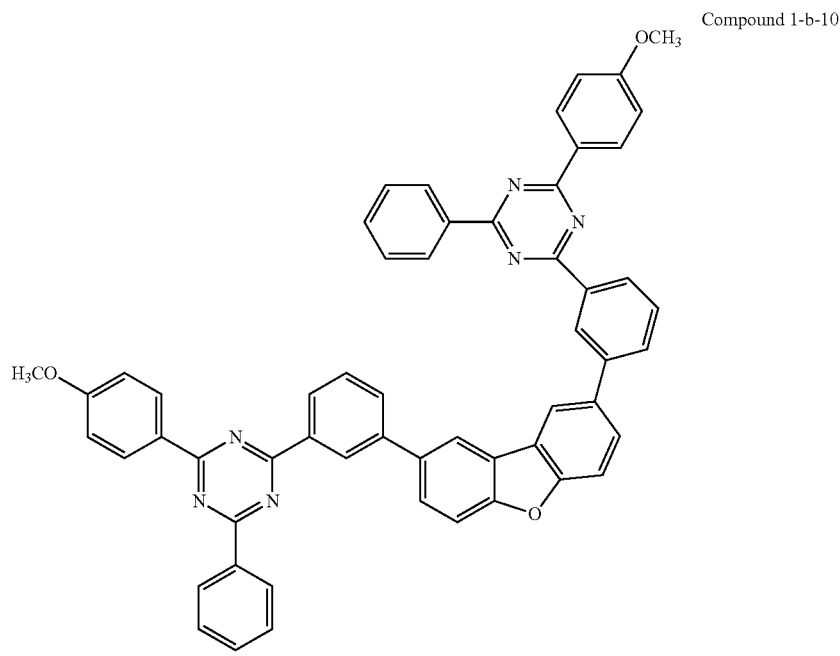
Compound 1-b-11
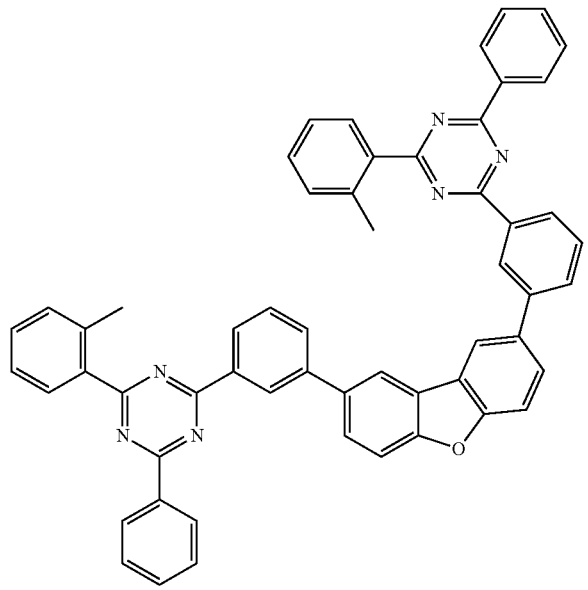

Compound 1-b-12
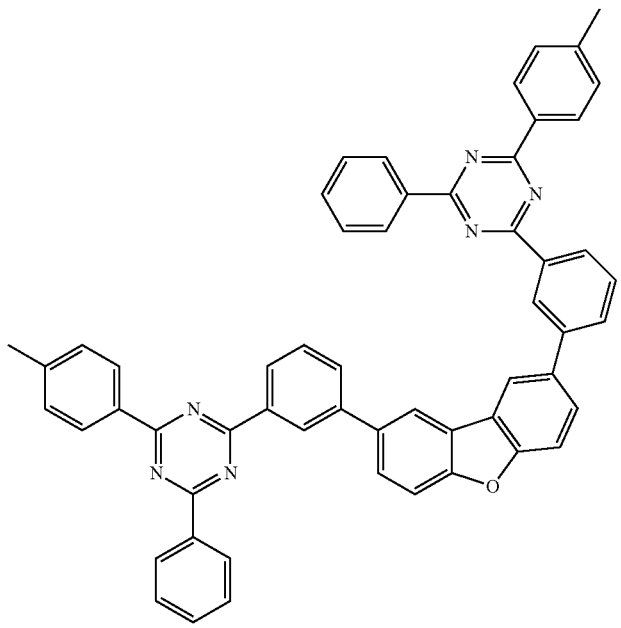
Compound 1-b-13
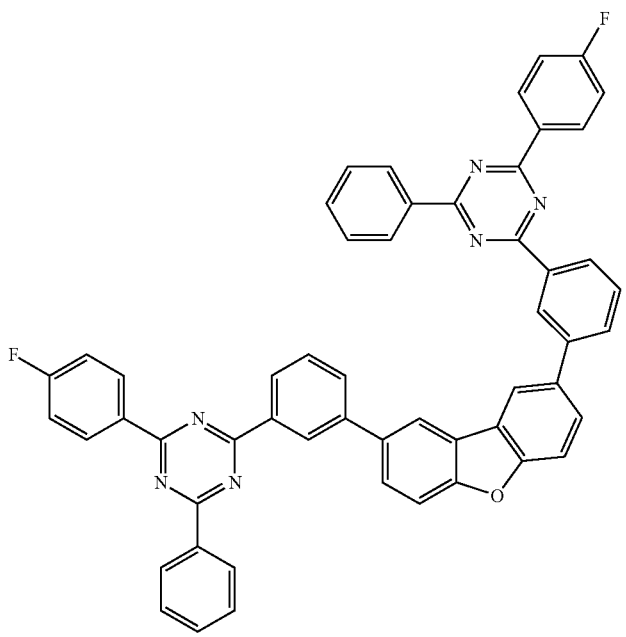

-continued
Compound 1-b-14
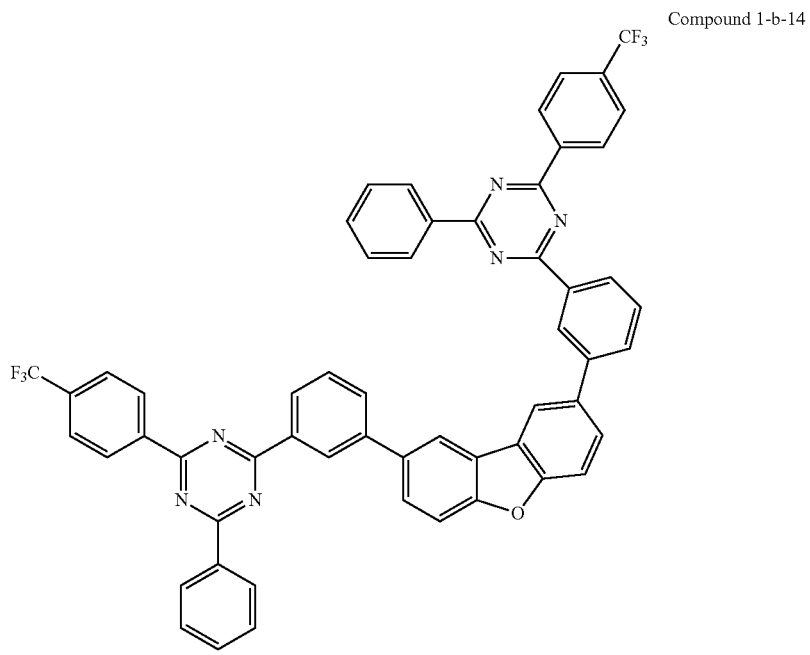
Compound 1-b-15
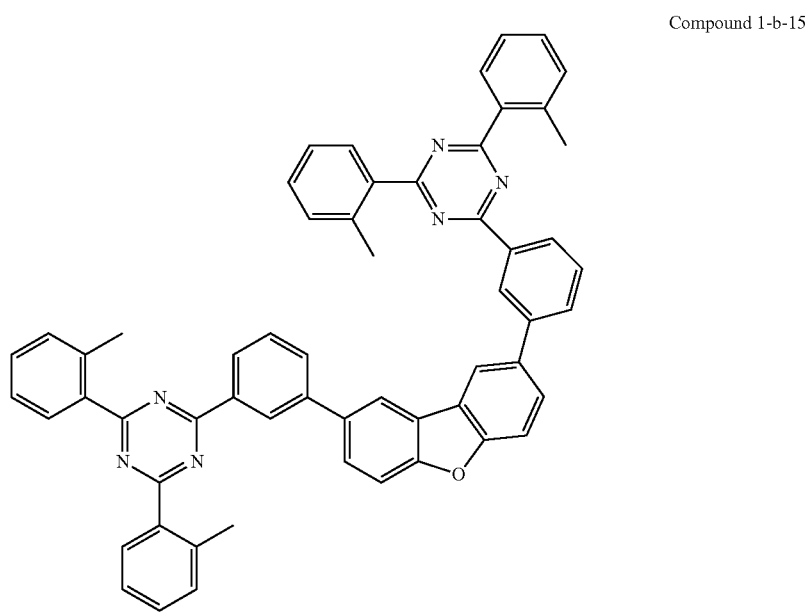

Compound 1-b-16
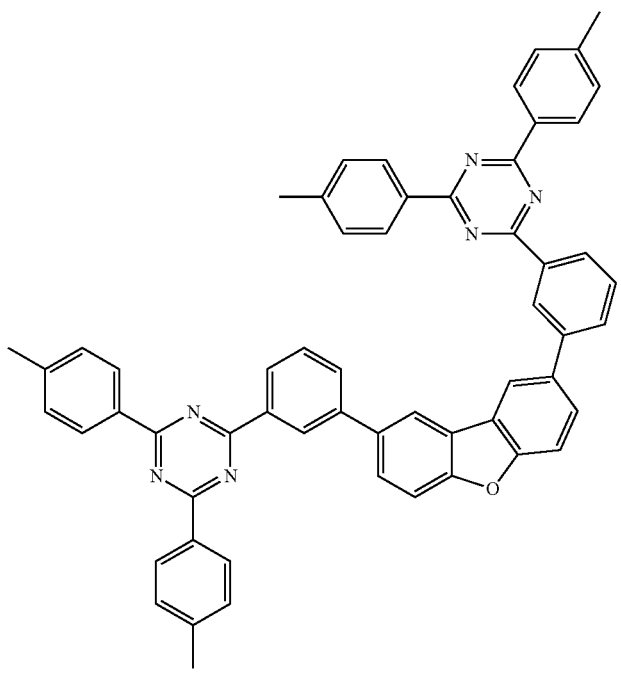
Compound 2-b-1
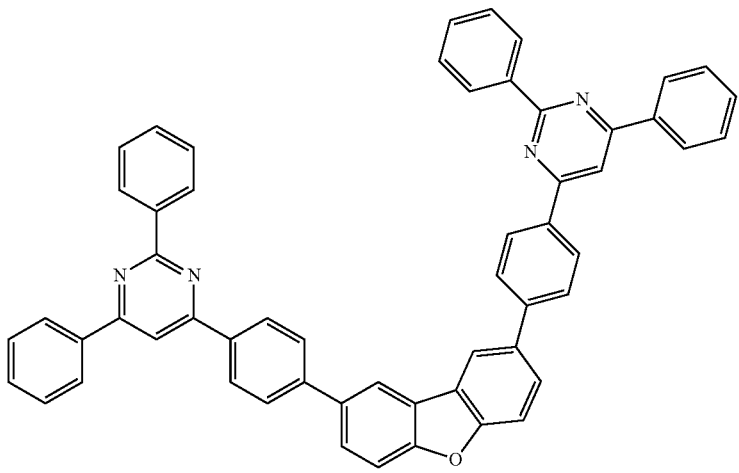
Compound 2-b-2
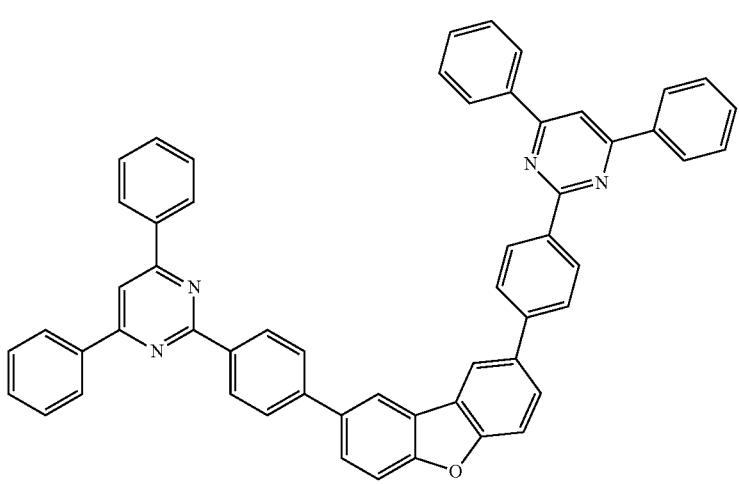

Compound 2-b-3
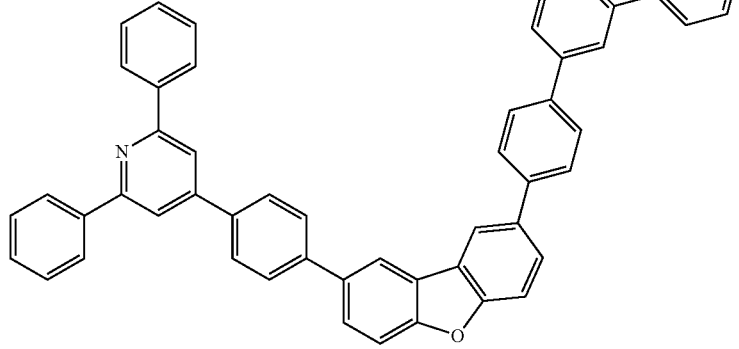
Compound 2-b-4
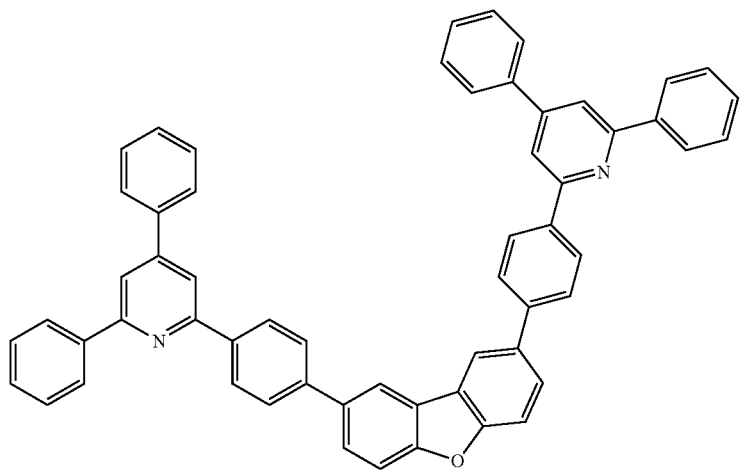
Compound 2-b-5
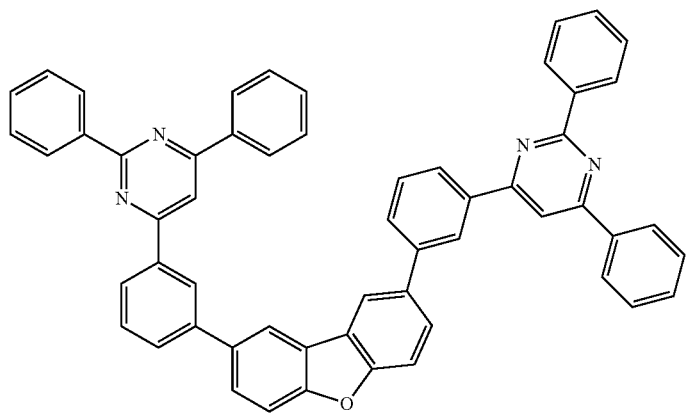

-continued
Compound 2-b-6
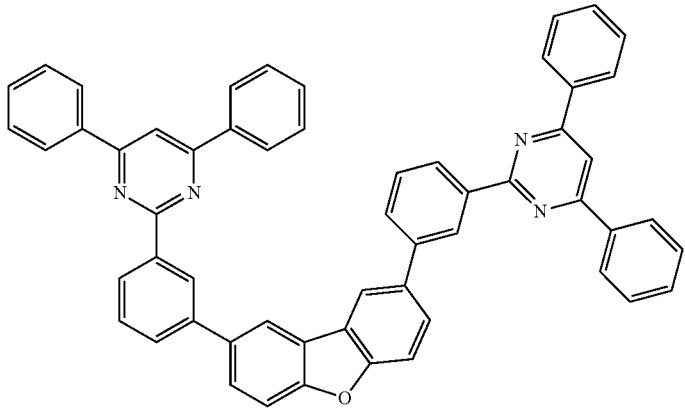
Compound 2-b-7
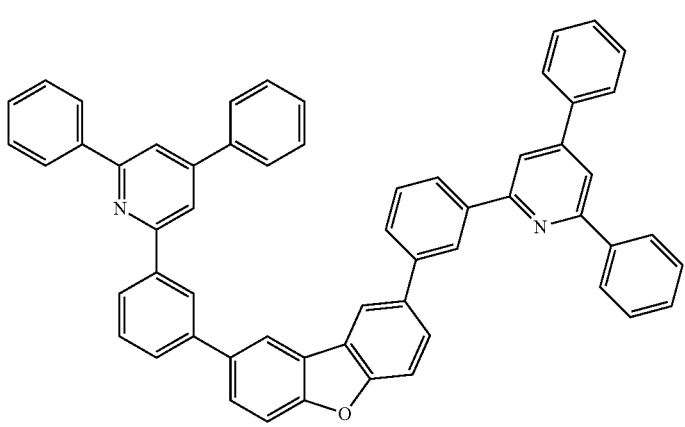
Compound 2-b-8
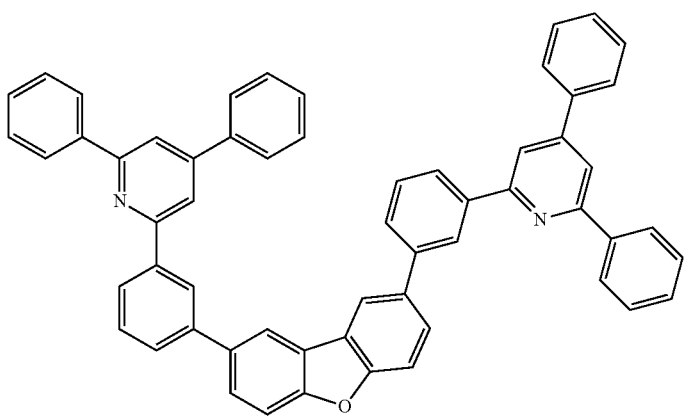

In an embodiment of the present disclosure, the compound represented by formula 1-c is any one of the following compounds 1-c-1 to 1-c-12 and 2-c-1 to 2-c-8:
Compound 1-c-1
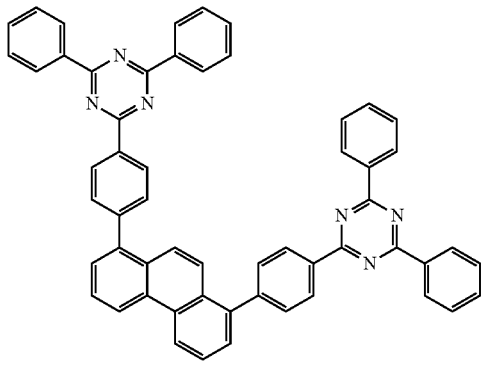
Compound 1-c-2
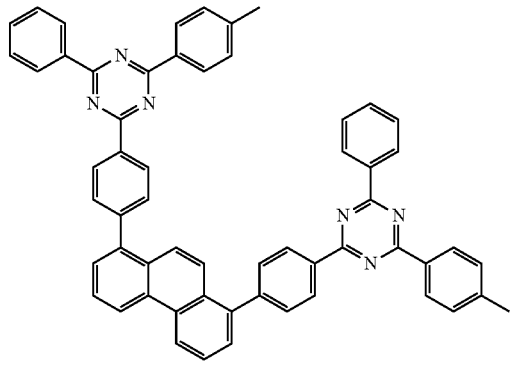
Compound 1-c-3
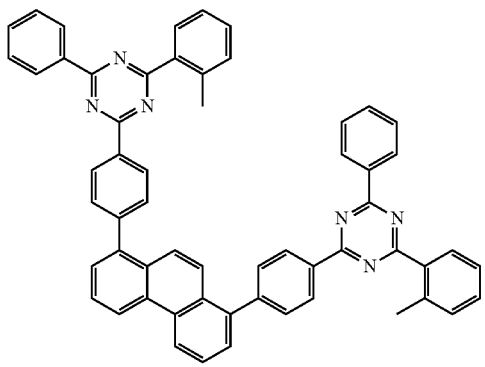
Compound 1-c-4
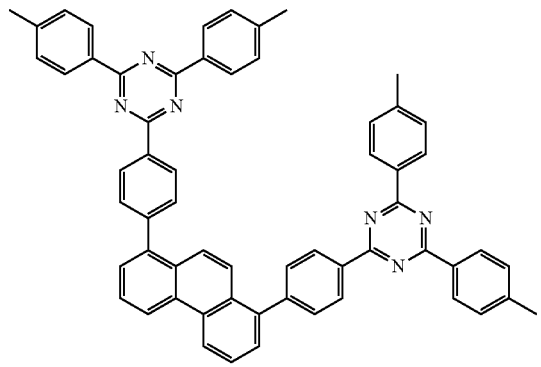
Compound 1-c-5
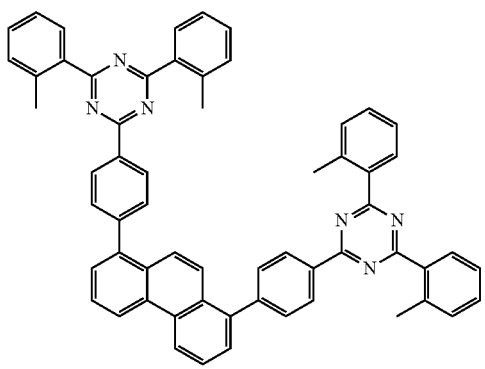
Compound 1-c-6
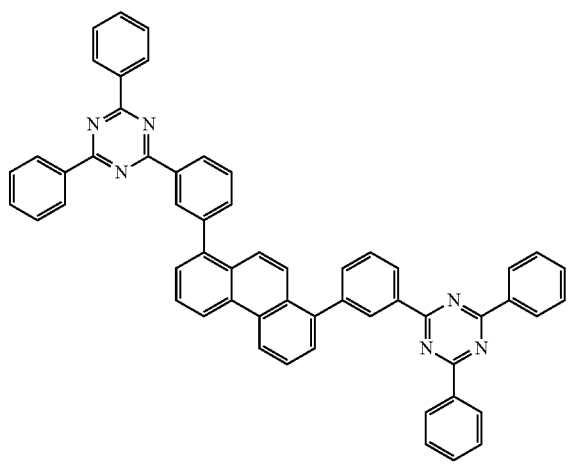

-continued
Compound 1-c-7
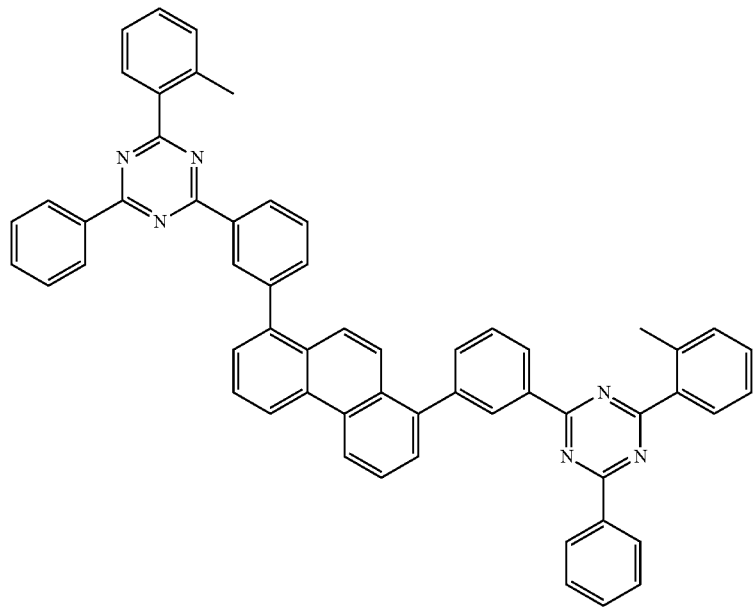
Compound 1-c-8
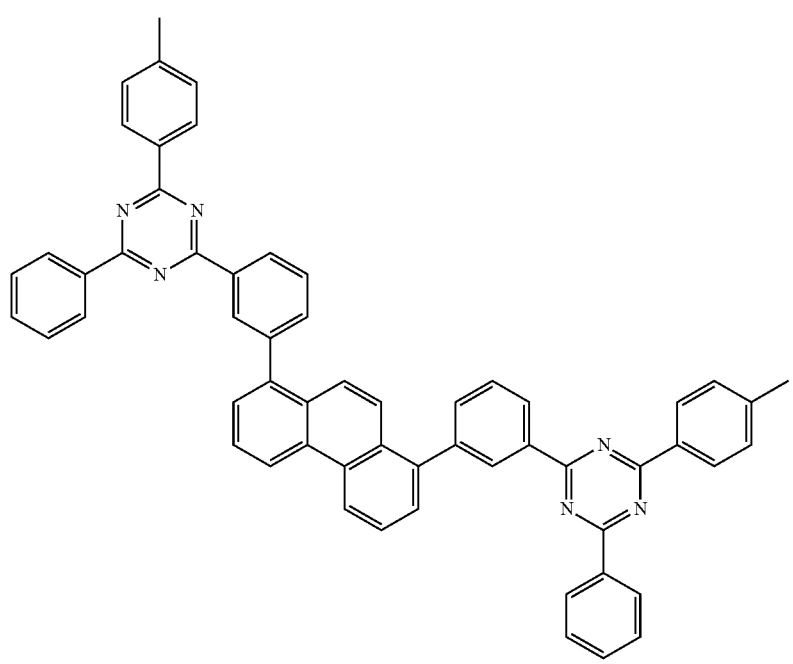

Compound 1-c-9
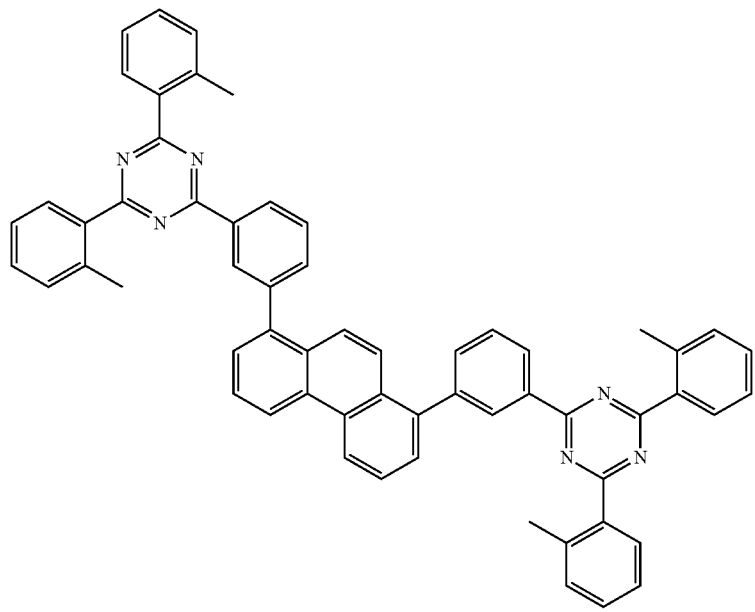
Compound 1-c-10
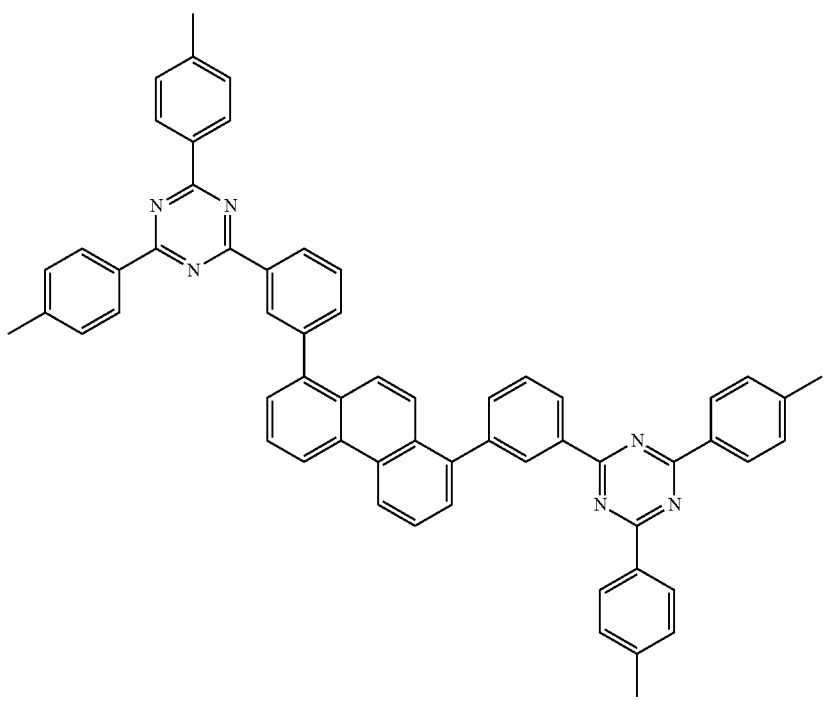

Compound 1-c-11
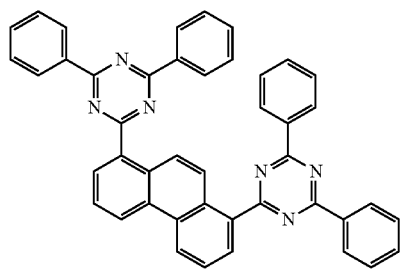
Compound 1-c-12
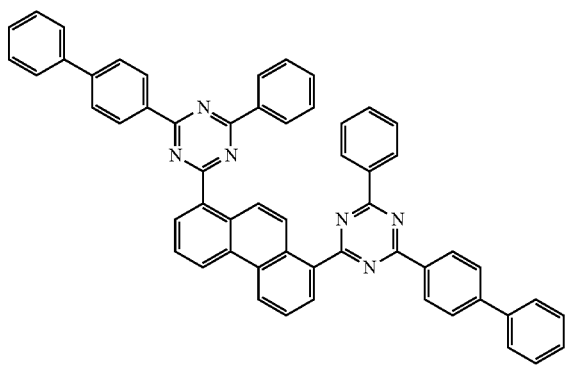
Compound 2-c-1
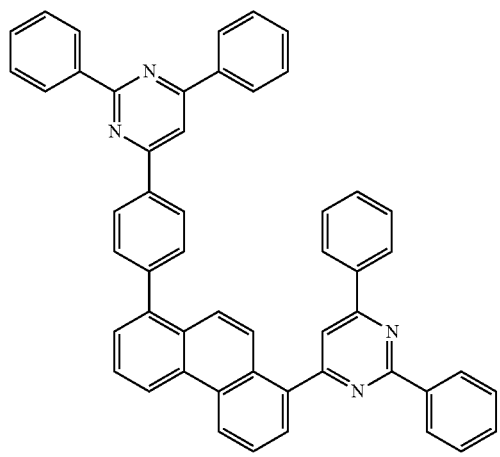
Compound 2-c-2
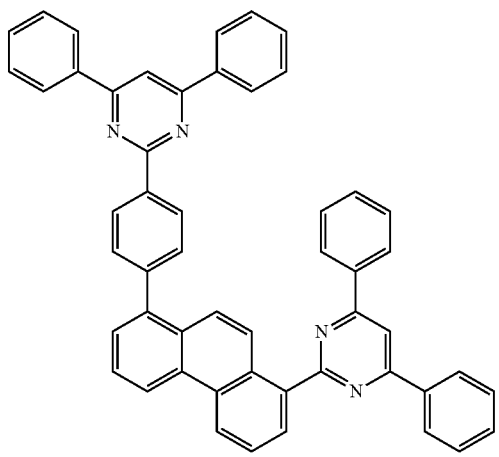
Compound 2-c-3
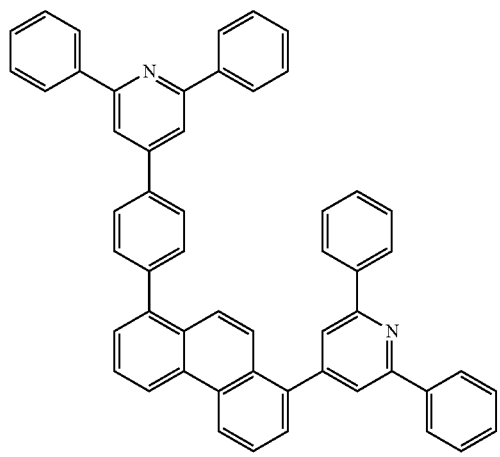
Compound 2-c-4
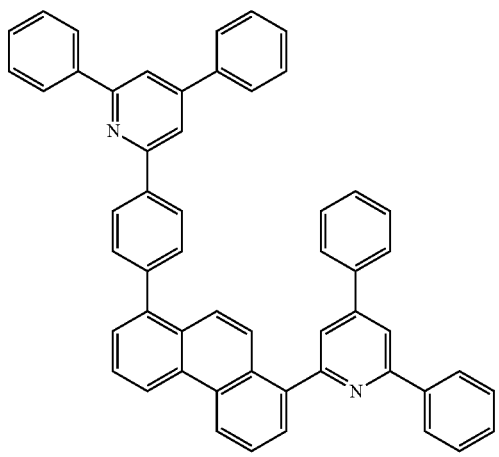

Compound 2-c-5
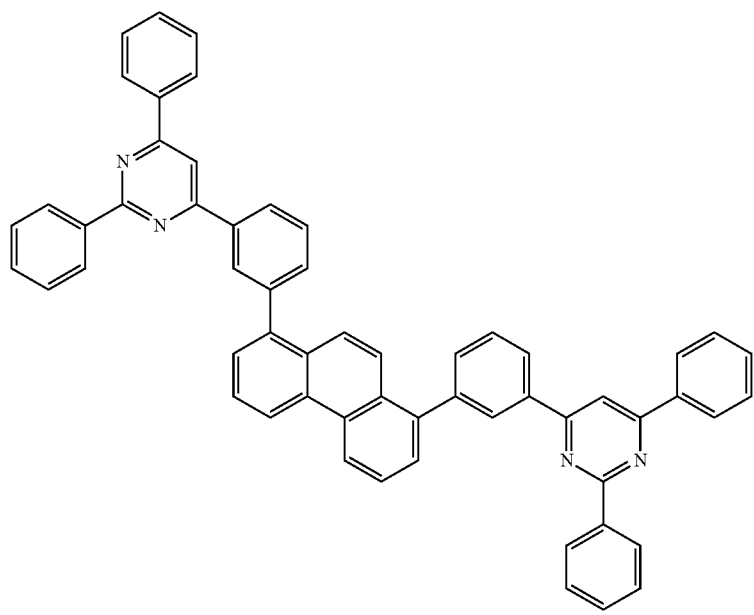
Compound 2-c-6
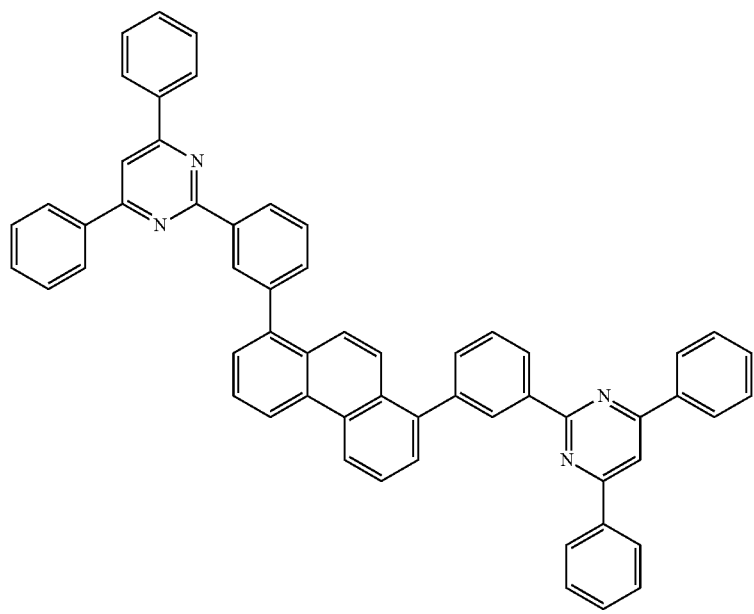

Compound 2-c-7
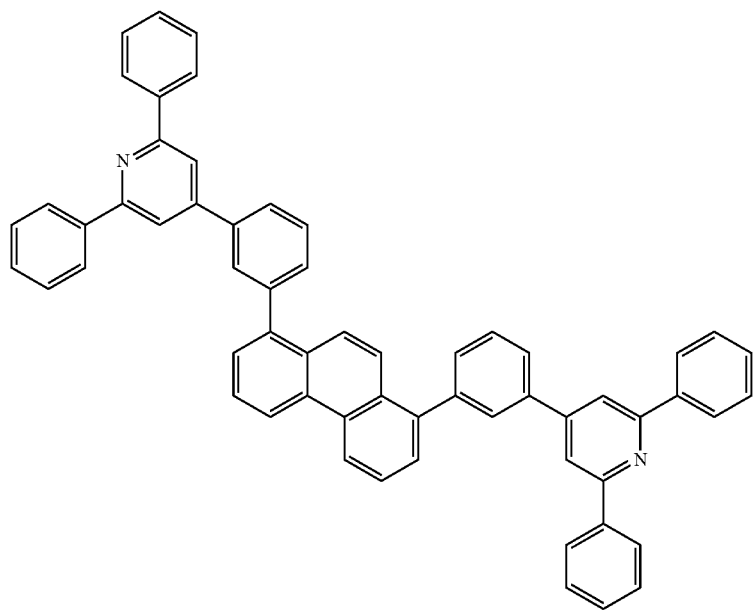
Compound 2-c-8
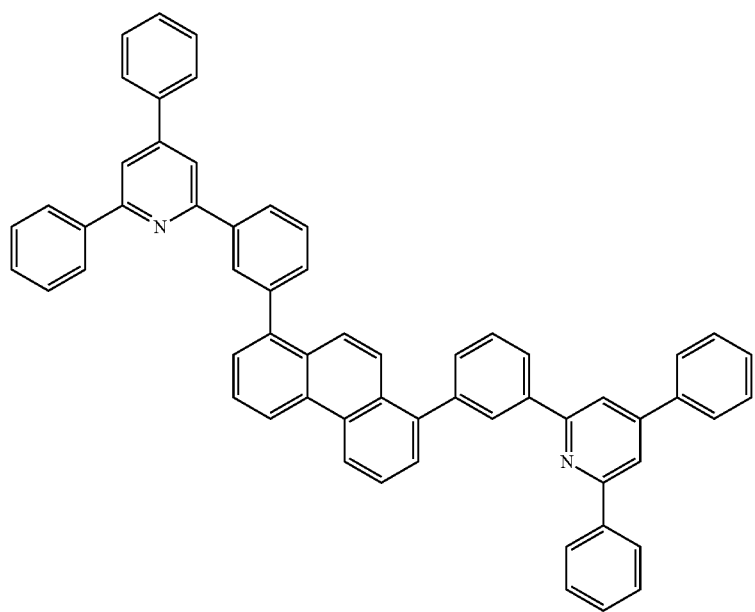

In an embodiment of the present disclosure, the compound represented by formula 1-d is any one of the following compounds 1-d-1 to 1-d-10 and 2-d-1 to 2-d-8:
Compound 1-d-1
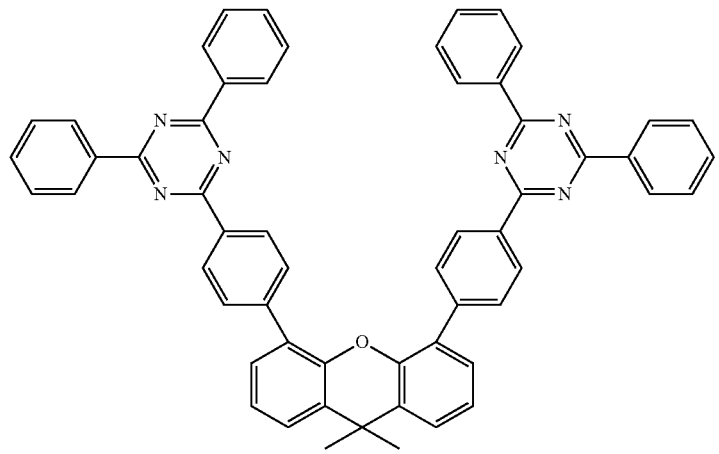
Compound 1-d-2
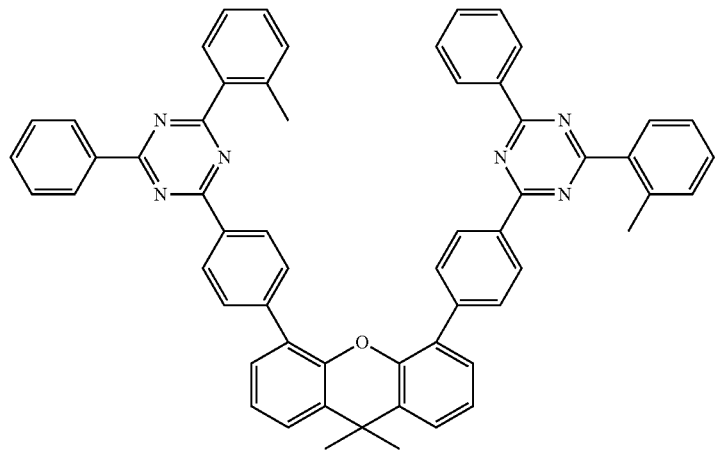
Compound 1-d-3
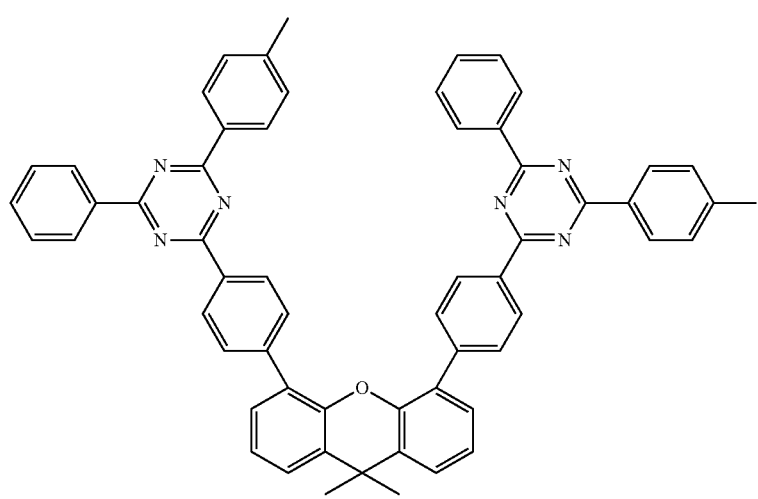

Compound 1-d-4
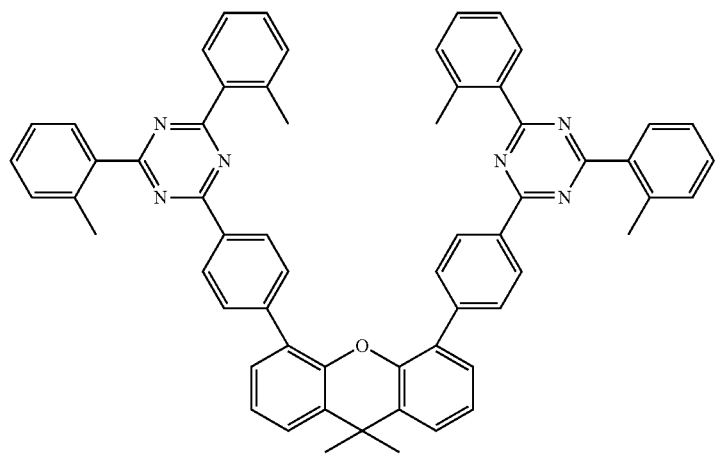
Compound 1-d-5
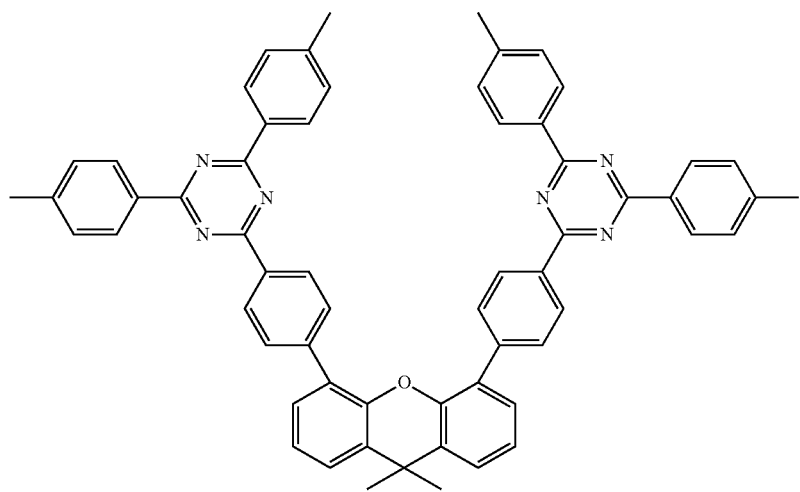
Compound 1-d-6
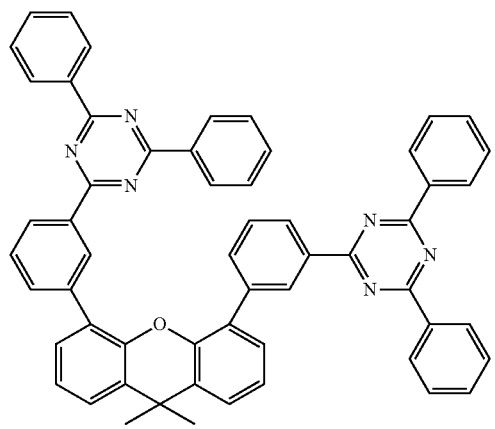
Compound 1-d-7
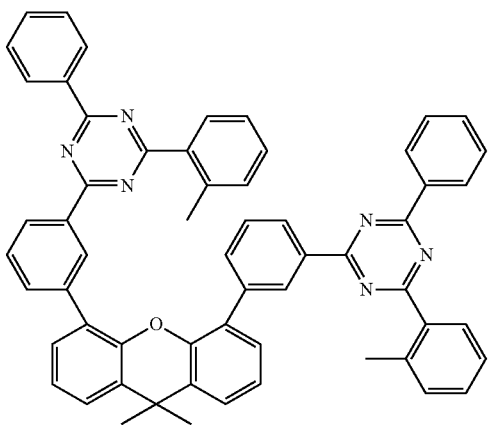

Compound 1-d-8
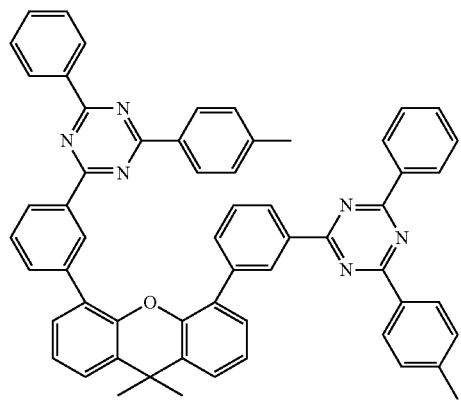
Compound 1-d-9
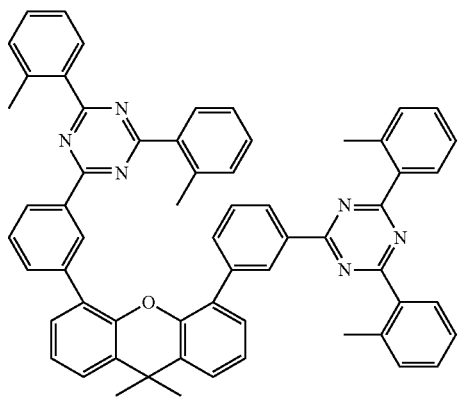
Compound 1-d-10
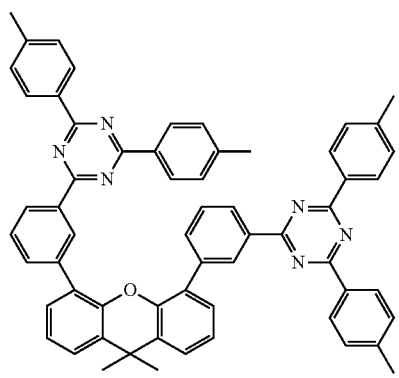
Compound 2-d-1
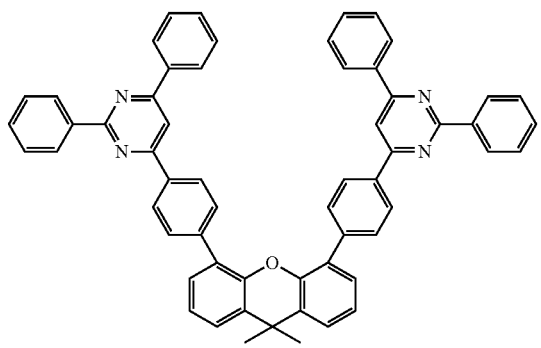
Compound 2-d-2
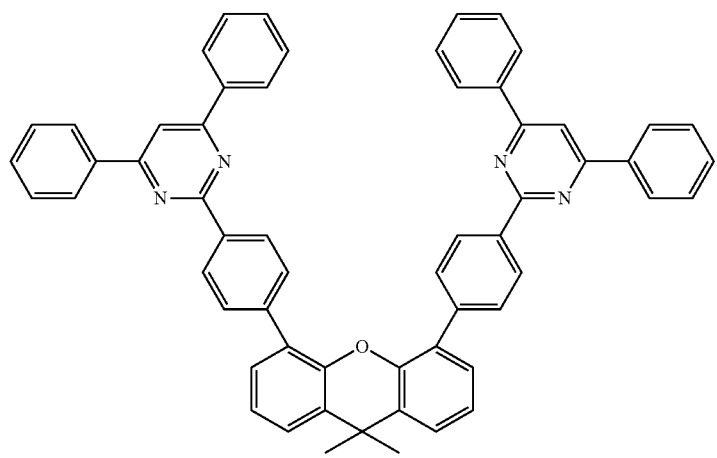

Compound 2-d-3
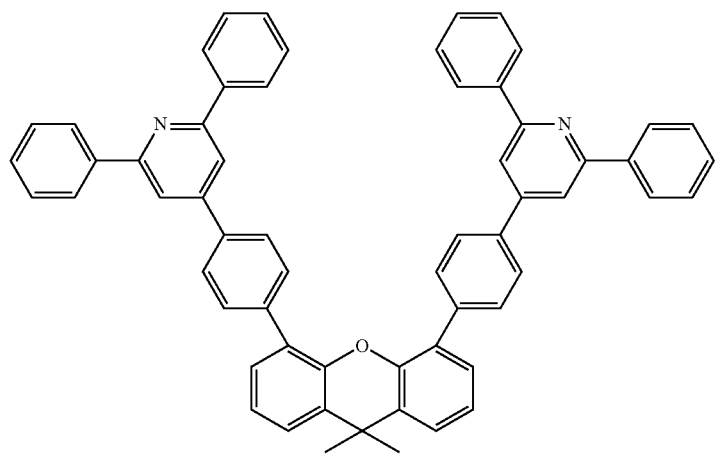
Compound 2-d-4
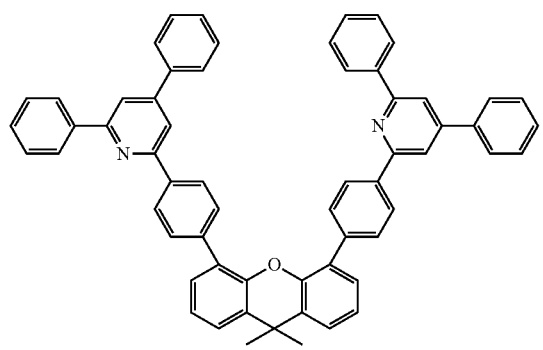
Compound 2-d-5
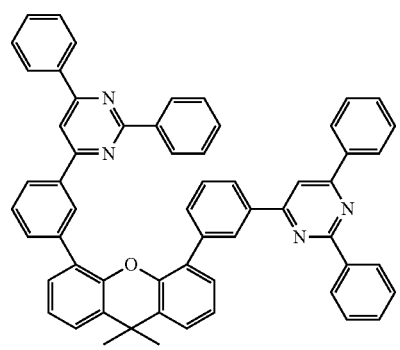
Compound 2-d-6
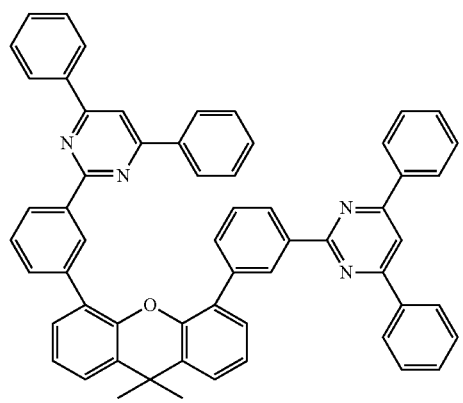
Compound 2-d-7
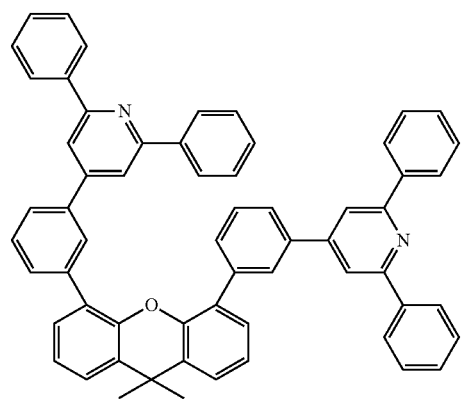

Compound 2-d-8
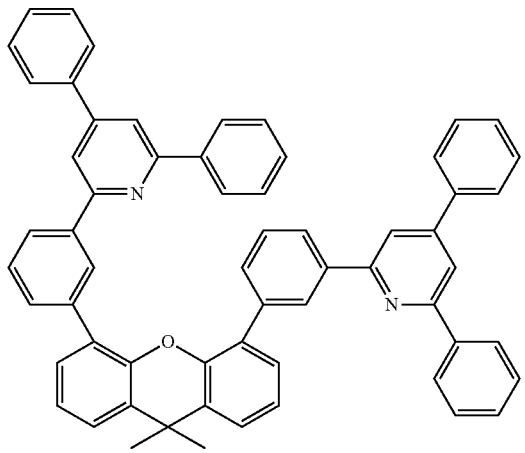
In an embodiment of the present disclosure, the compound represented by formula 1-e is any one of the following compounds 1-e-1 to 1-e-10 and 2-e-1 to 2-e-8:
Compound 1-e-1
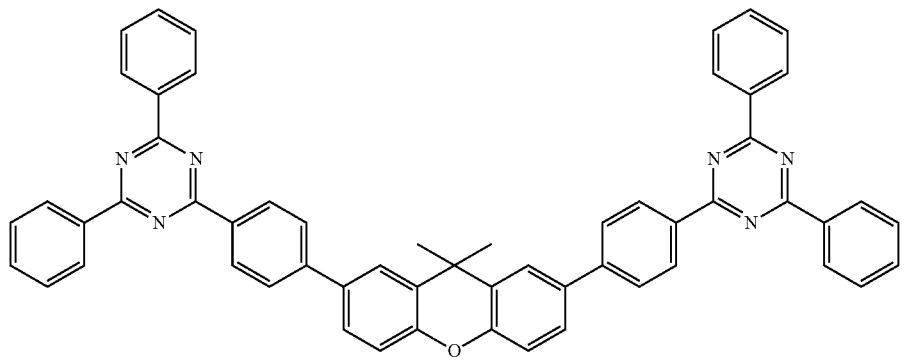
Compound 1-e-2
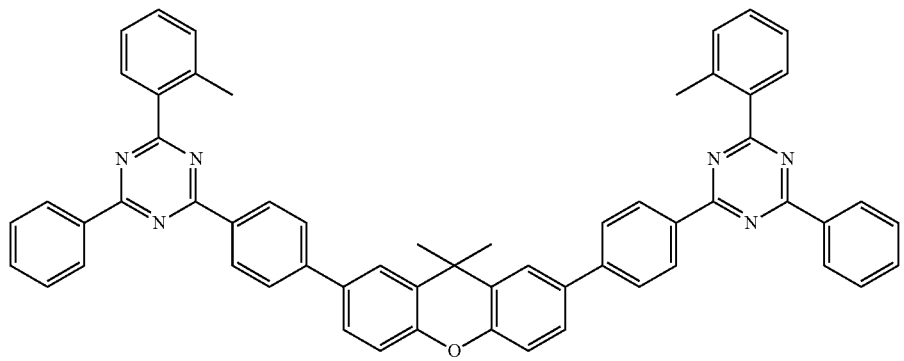

Compound 1-e-3
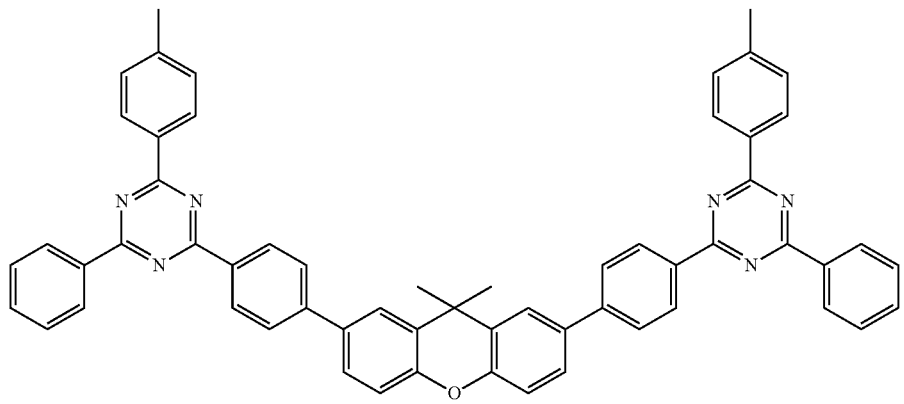
Compound 1-e-4
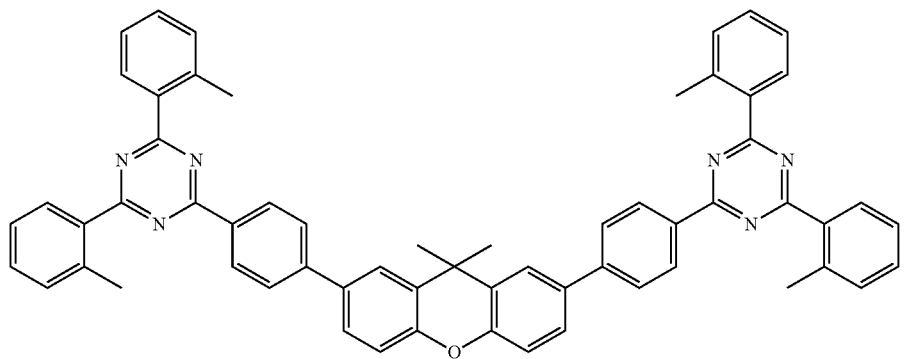
Compound 1-e-5
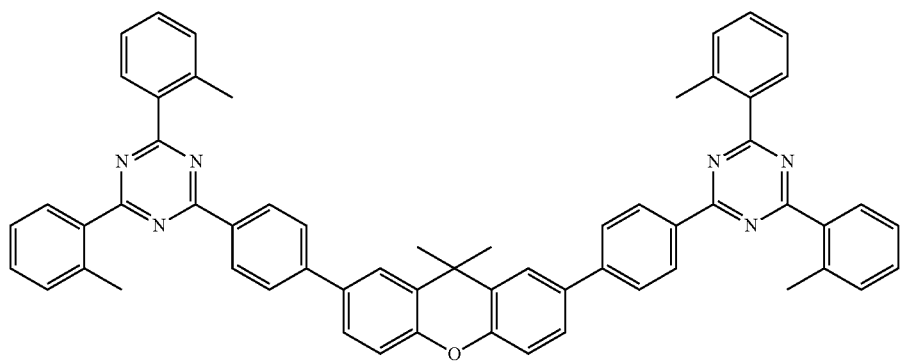
Compound 1-e-6
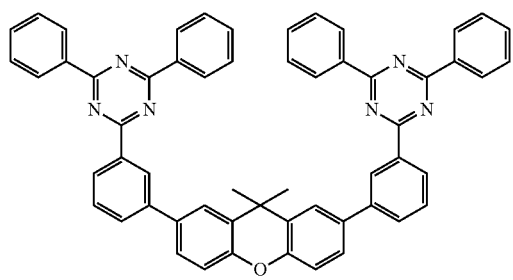
Compound 1-e-7
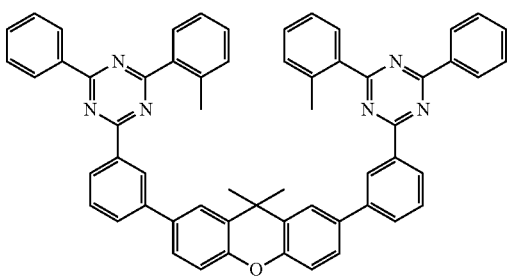

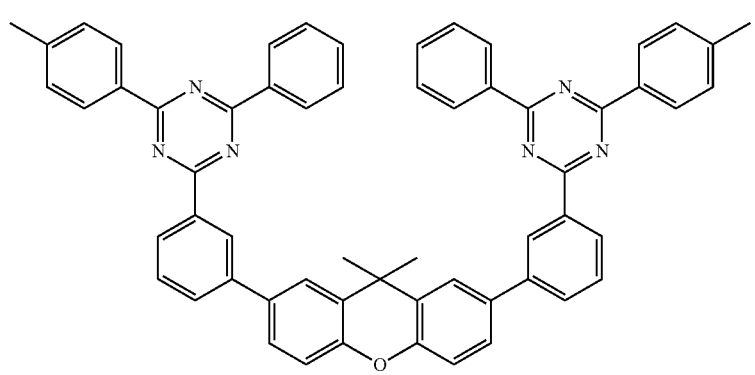
Compound 1-e-8
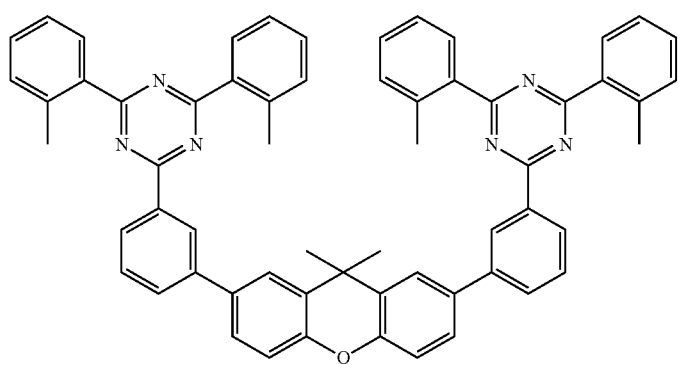
Compound 1-e-9
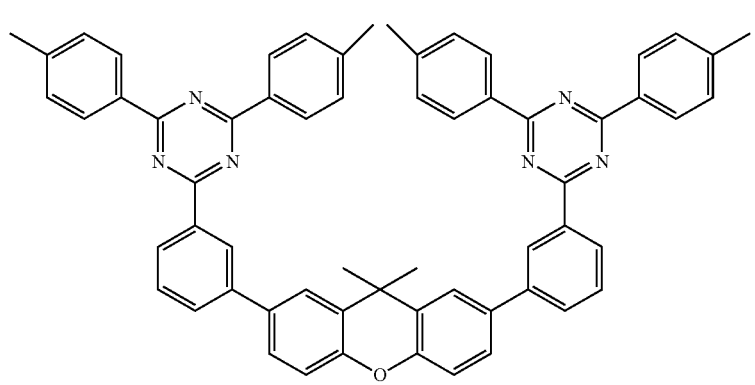
Compound 1-e-10
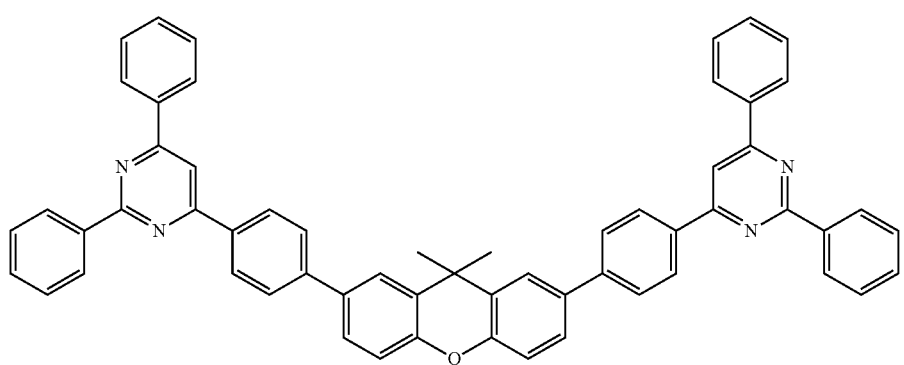
Compound 2-e-1

Compound 2-e-2
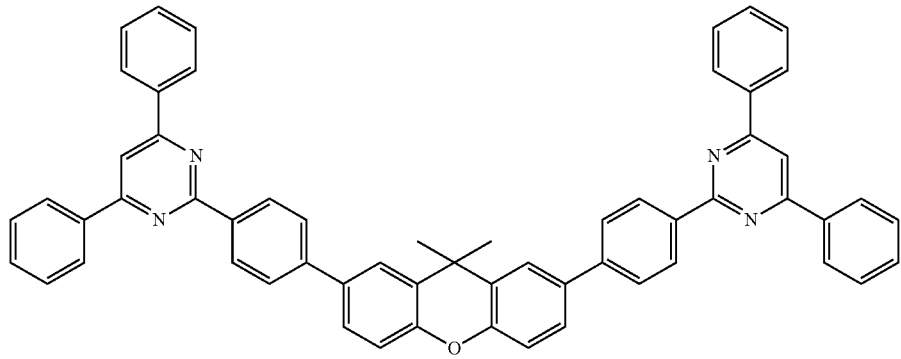
Compound 2-e-3
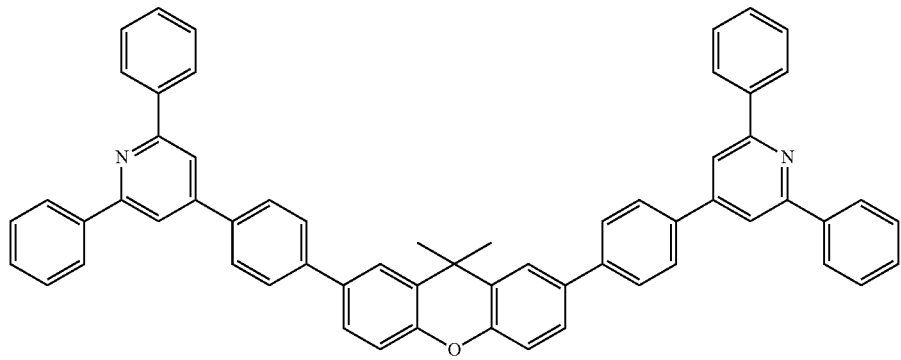
Compound 2-e-4
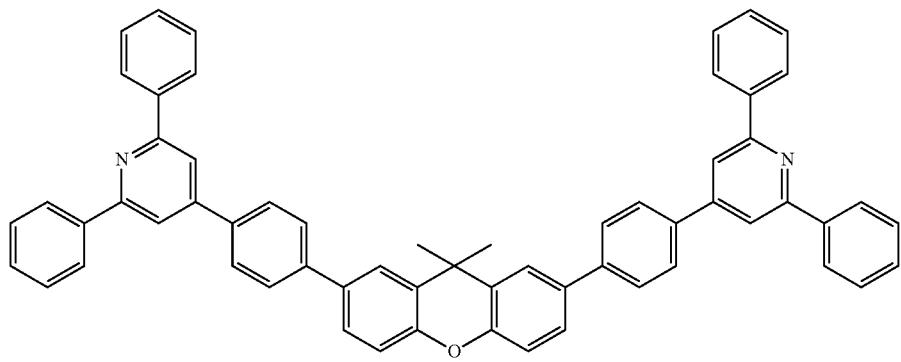
Compound 2-e-5
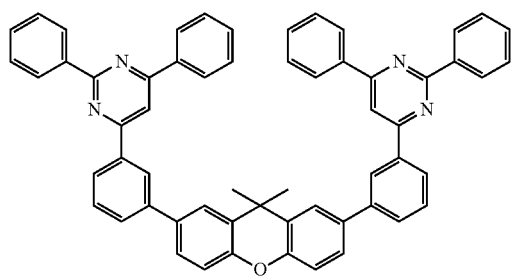
Compound 2-e-6
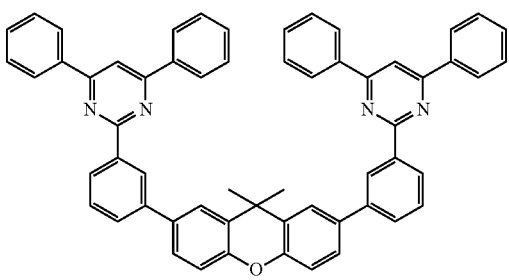

Compound 2-e-7
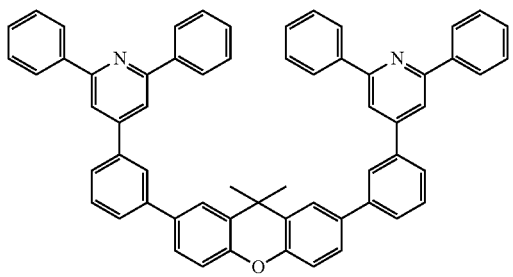
Compound 2-e-8
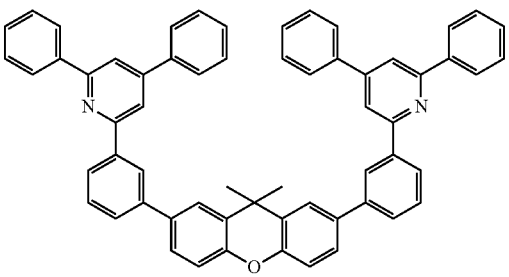
In an embodiment of the present disclosure, the compound represented by formula 1-f is any one of the following compounds 1-f-1 to 1-f-12 and 2-f-1 to 2-f-8:
Compound 1-f-1
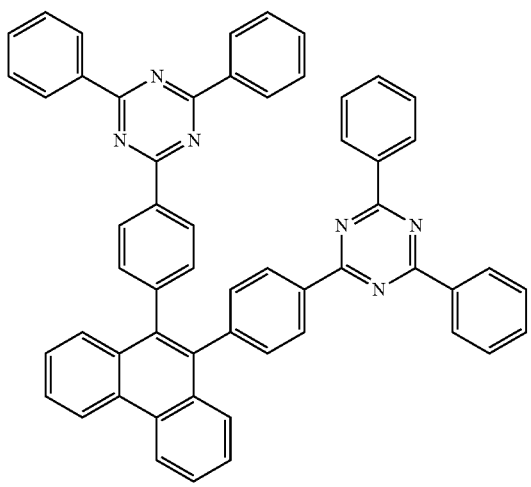
Compound 1-f-3
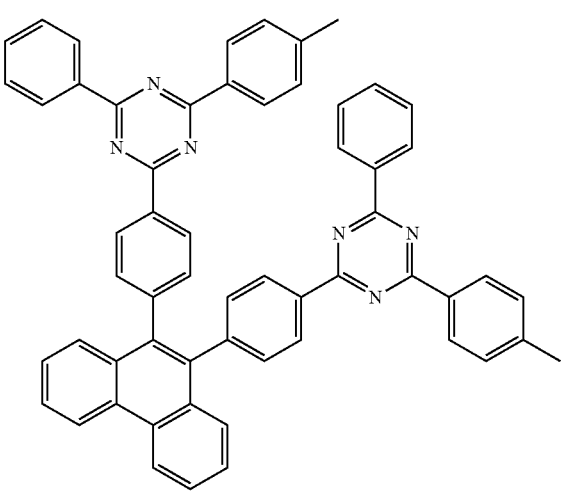
Compound 1-f-2
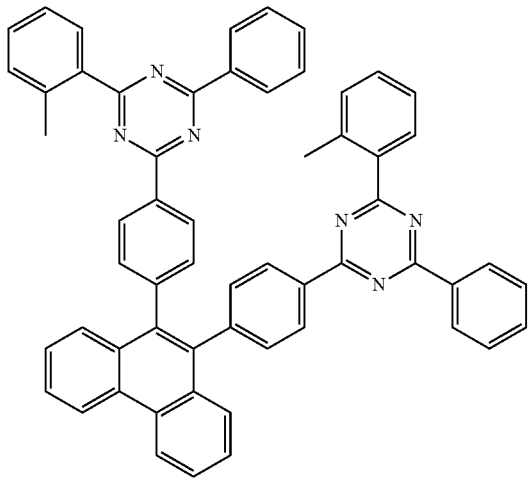
Compound 1-f-4
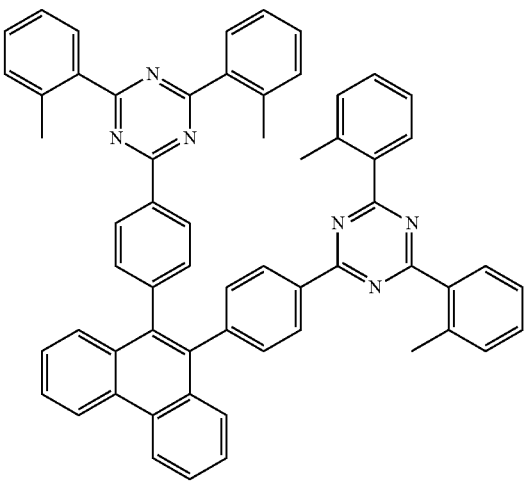

-continued
Compound 1-f-5
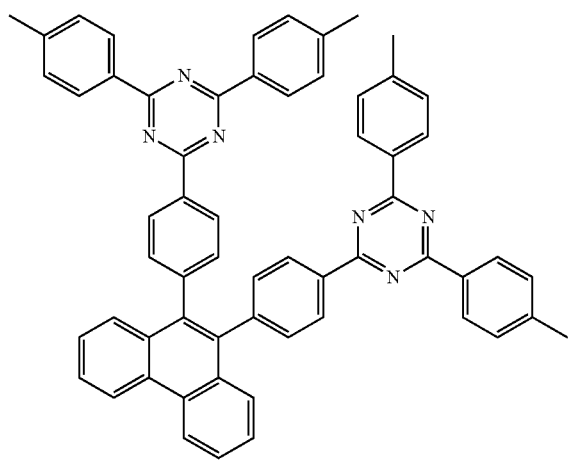
Compound 1-f-8
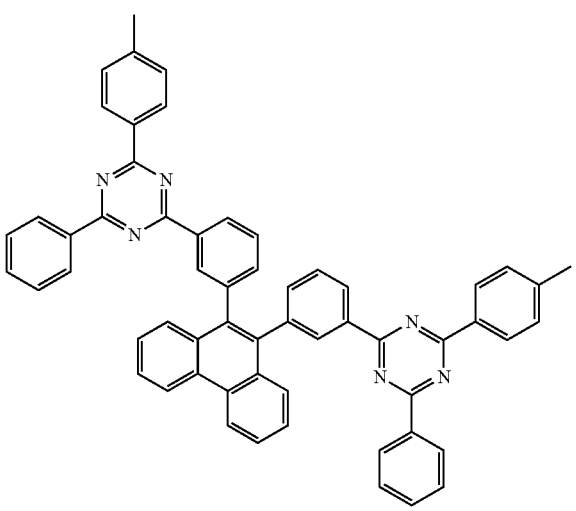
Compound 1-f-6
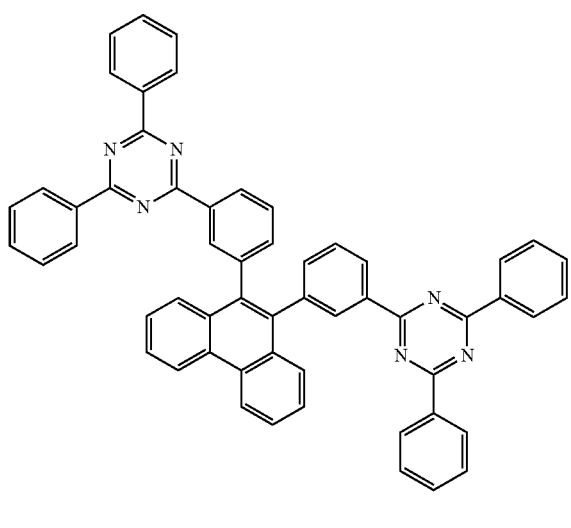
Compound 1-f-9
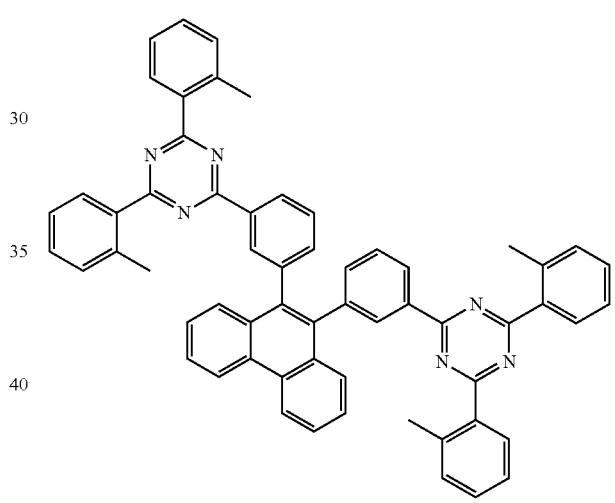
Compound 1-f-7
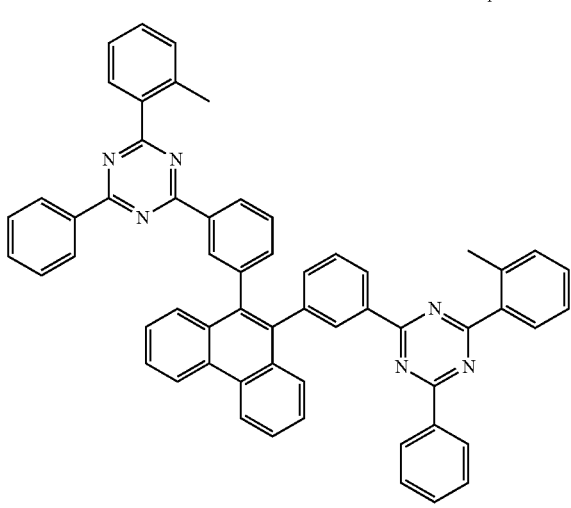
Compound 1-f-10
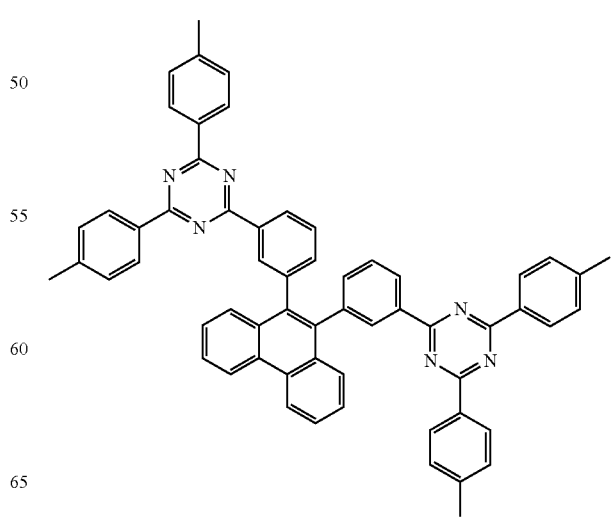

Compound 1-f-11
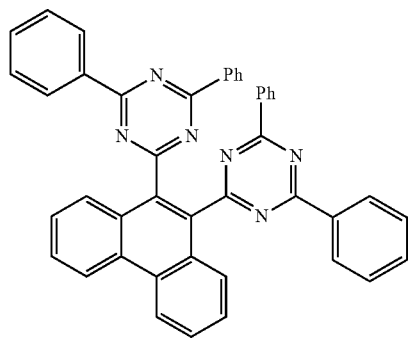
Compound 2-f-2
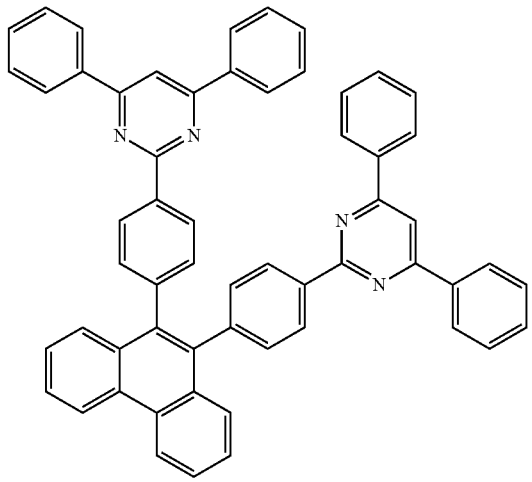
Compound 1-f-12
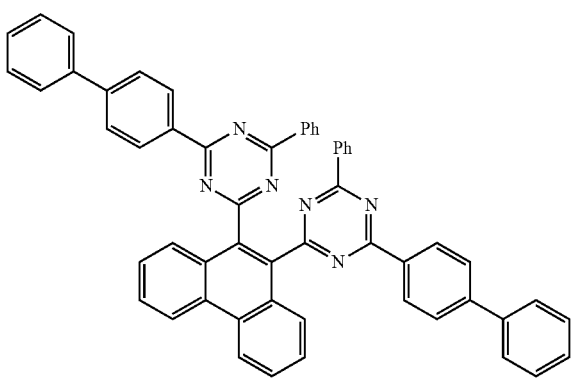
Compound 2-f-3
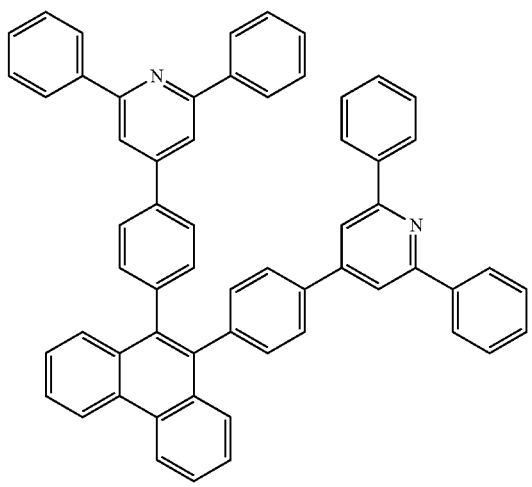
Compound 2-f-1
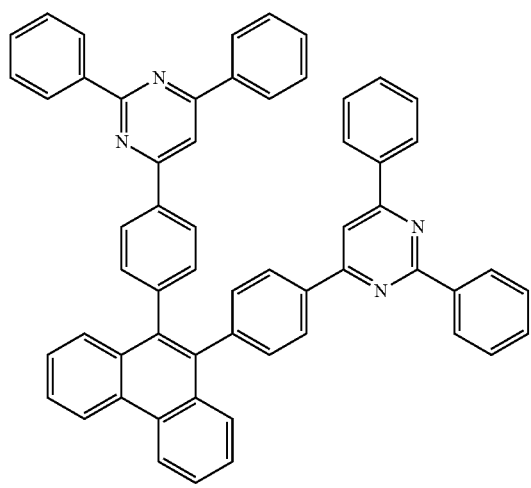
Compound 2-f-4
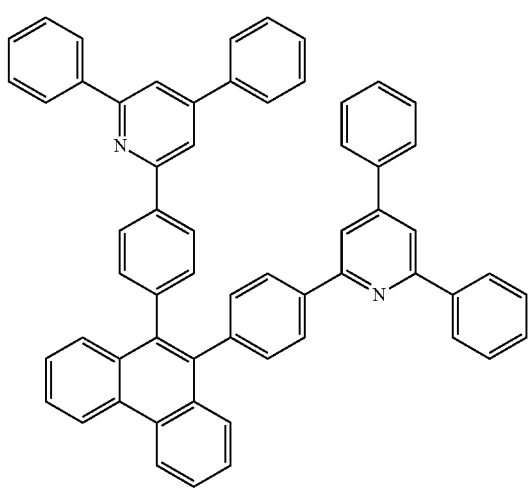

Compound 2-f-5

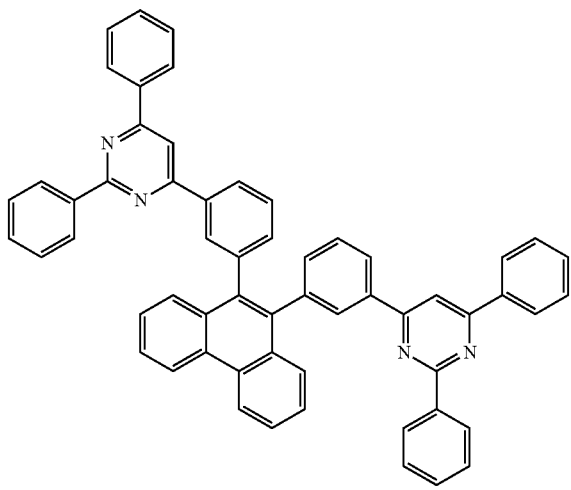

Compound 2-f-6

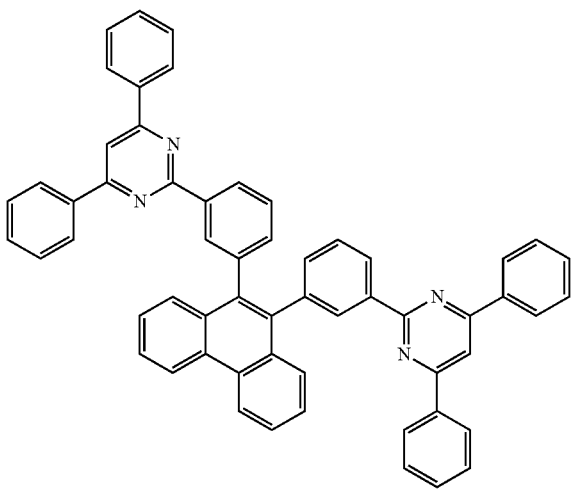

Compound 2-f-7

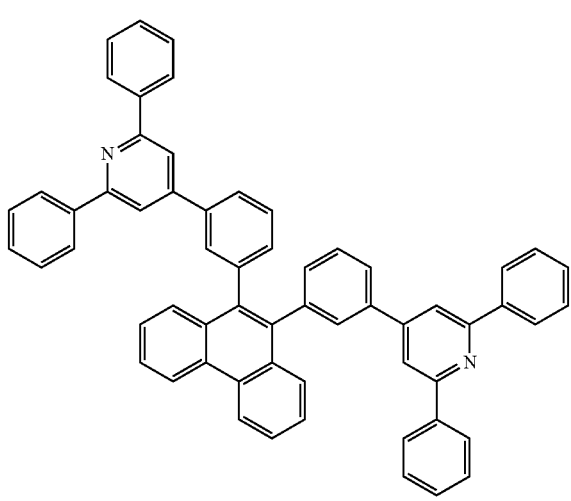

Compound 2-f-8

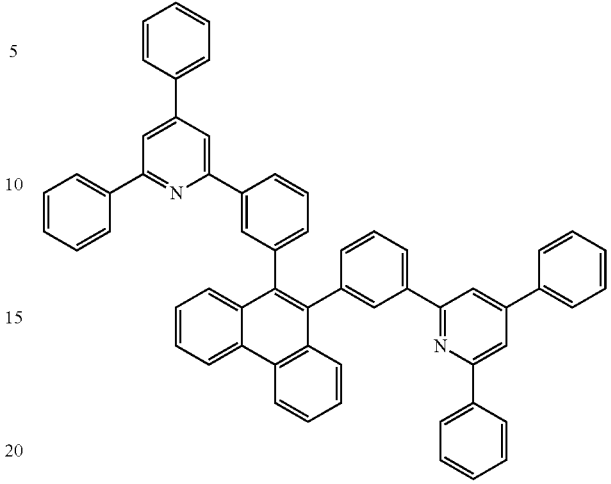

The compound of formula 1 may have suitable characteristics for use as an organic material layer in an organic electronic device as a result of introducing various substituents into the heterocyclic structure, which is the core structure shown in formula 1.

The conjugation length and energy band gap of a compound have a close relationship with each other. Specifically, as the conjugation length of a compound increases, the energy band gap decreases. As described above, the core structure of the compound of formula 1 has a limited conjugation length, and thus has a high energy band gap.

In the present disclosure, compounds having various energy band gaps can be synthesized by introducing various substituents into the positions $Ar_1$ to $Ar_3$ and $R_1$ to $R_9$ of the core structure having a high energy band gap as described above. It is generally easy to control the energy band gap by introducing the substituents of a core structure having a high energy band gap. However, when a core structure has a low energy band gap, it is difficult to control the energy band gap so as to have a high level by introducing substituents into the core structure. In addition, in the present disclosure, the HOMO and LUMO energy levels of the compound can also be controlled by introducing various substituents into the positions of $Ar_1$ to $Ar_3$ and $R_1$ to $R_9$ of the above-described core structure.

Moreover, when various substituents are introduced into the above-described core structure, a compound having the inherent characteristics of the introduced substituents can be synthesized. For example, when substituents which are mainly used in materials for the hole-injecting layer, hole-transporting layer, light-emitting layer and electron-transporting layer of an organic electronic device are introduced into the above-described core structure, a material that satisfies the conditions required for each of the organic material layers can be synthesized.

Because the compound of formula 1 includes the heterocyclic structure in the core structure, it may have a suitable energy level for use as a hole-injecting material and/or a hole-transporting material in an organic light-emitting device. In the present disclosure, when a compound having a suitable energy level, attributable to the substituents introduced therein, is selected from among the compounds of formula 1 and used in an organic light-emitting device, the device may have a low driving voltage and a high optical efficiency.

In addition, when various substituents, particularly hydrogen or deuterium, are introduced into the core structure, the energy band gap can be finely controlled, while the characteristics of the interface between organic materials in an organic electronic device can be improved and the compound of formula 1 may be used in various applications.

Meanwhile the compound of formula 1 has excellent thermal stability due to its high glass transition temperature ($T_g$). This increase in the thermal stability is an important factor that provides driving stability to a device.

The compound of formula 1 can be prepared based on Preparation Examples which will be described below.

The heterocyclic compound of formula 1 can be prepared by substituting the heterocyclic ring of formula 1, which includes $X_1$ to $X_3$, with $Ar_1$, $Ar_2$ and L, and then bonding the two substituted heterocyclic rings, which include $X_1$ to $X_3$, to $Ar_3$.

In addition to compounds 1-a-1 to 1-a-16, 2-a-1 to 2-a-8, 1-b-1 to 1-b-16, 2-b-1 to 2-b-8,1-c-1 to 1-c-12, 2-c-1 to 2-c-8,1-d-1 to 1-d-10, 2-d-1 to 2-d-8,1-e-1 to 1-e-10, 2-e-1 to 2-e-8,1-f-1 to 1-f-12 and 2-f-1 to 2-f-8, other compounds represented by formula 1 can be prepared by changing the number of heteroatoms of $X_1$ to $X_3$ and the substituent groups of $Ar_1$ to $Ar_3$ and L.

The present disclosure also provides an organic electronic device comprising the compound of formula 1.

In an embodiment of the present disclosure, the organic electronic device may have a structure comprising a first electrode, a second electrode and one or more organic material layers interposed between the first and second electrodes.

The organic electronic device may be selected from the group consisting of an organic light-emitting device, an organic solar cell and an organic transistor.

In an embodiment of the present disclosure, the organic electronic device may be an organic light-emitting device.

In an embodiment of the present disclosure, there is provided an organic light-emitting device comprising a first electrode, a second electrode and one or more organic material layers interposed between the first and second electrodes, wherein one or more of the organic material layers comprise the heterocyclic compound represented by formula 1.

The organic material layers of the organic light-emitting device according to the present disclosure may have a single-layer structure or a multilayer structure consisting of two or more organic material layers. For example, the organic light-emitting device according to the present disclosure may have a structure comprising organic material layers, including a hole-injecting layer, a hole-transporting layer, a light-emitting layer, an electron-transporting layer and an electron-injecting layer. However, the structure of the organic light-emitting device is not limited thereto and may comprise a smaller number of organic layers.

Thus, in another embodiment of the present disclosure, the organic material layers of the organic light-emitting device may include one or more of a hole-injecting layer, a hole-transporting layer and a layer that performs both hole injection and hole transport, and one or more of the layers may comprise the compound represented by formula 1.

Specifically, the organic material layers of the organic light-emitting device may include a hole-injecting layer, in which the hole-injecting layer may comprise the compound represented by formula 1. In another embodiment, the organic material layers of the organic light-emitting device may include a hole-transporting layer, in which the hole-transporting layer may comprise the compound represented by formula 1. In still another embodiment, the organic material layers of the organic light-emitting device may include a hole-transporting layer and a hole-injecting layer, wherein the hole-transporting layer and the hole-injecting layer may comprise the compound represented by formula 1.

In addition, the organic material layers may include a light-emitting layer, in which the light-emitting layer may comprise the compound represented by formula 1. In an embodiment, the compound represented by formula 1 may be included as a host in the light-emitting layer. In another embodiment, the organic material layer comprising the compound represented by formula 1 may include the compound of formula 1 as a host and may include another organic compound, a metal or a metal compound as a dopant.

In addition, the organic material layers may include one or more of an electron-transporting layer, an electron-injecting layer or a layer that performs both electron transport and electron injection, wherein one or more of the layers may comprise the compound represented by formula 1.

Specifically, the organic material layers of the organic light-emitting device may include an electron-injecting layer, wherein the electron-injecting layer may comprise the compound represented by formula 1. In another embodiment, the organic material layers of the organic light-emitting device may include an electron-transporting layer, wherein the electron-transporting layer may comprise the compound represented by formula 1. In still another embodiment, the organic material layers of the organic light-emitting device may include an electron-transporting layer and an electron-injecting layer, wherein the electron-transporting layer and the electron-injecting layer may comprise the compound represented by formula 1.

In this multilayer organic layer structure, the compound represented by formula 1 may be included in the light-emitting layer, the layer that performs all hole injection, hole transport and light emission, the layer that performs both hole transport and light emission, or the layer that performs both electron transport and light emission.

In another embodiment, the organic material layers of the organic light-emitting device may include, in addition to the organic material layer comprising the heterocyclic composition represented by formula 1, a hole-injecting layer or a hole-transporting layer, which comprises a compound containing an arylamino group, a carbazole group or a benzcarbazole group.

In an embodiment of the present disclosure, the organic electronic device may be an organic solar cell.

In an embodiment of the present disclosure, there is provided an organic solar cell comprising a first electrode, a second electrode and one or more organic material layers, including a photoactive layer, interposed between the first electrode and the second electrode, wherein one or more of the organic layers comprise the heterocyclic compound represented by formula 1.

In an embodiment of the present disclosure, the organic solar cell may include an electron-transporting layer, wherein the electron-transporting layer may comprise the compound represented by formula 1.

In another embodiment, the photoactive layer may comprise the compound represented by formula 1.

In still another embodiment, the organic solar cell may include a photoactive layer, an electron donor and an electron acceptor, wherein the photoactive layer, the electron donor and the electron acceptor may comprise the compound represented by formula 1.

In an embodiment of the present disclosure, when the organic solar cell receives a photon from an external light source, an electron and a hole are generated between the electron donor and the electron acceptor. The generated hole is transported to the anode through the electron donor layer.

In an embodiment of the present disclosure, the organic solar cell may further include an additional organic material layer. The organic solar cell may comprise a material having various functions in order to reduce the number of organic material layers therein.

In an embodiment of the present disclosure, the organic electronic device may be an organic transistor.

In an embodiment of the present disclosure, there is provided an organic transistor comprising a source, a drain, a gate and one or more organic material layers.

In an embodiment of the present disclosure, the organic transistor may include a charge-generating layer, wherein the charge-generating layer may comprise the compound represented by formula 1.

In another embodiment of the present disclosure, the organic transistor may include an insulating layer, wherein the insulating layer may be located on a substrate and the gate.

When the organic electronic device includes a plurality of organic material layers, the organic material layers may be formed of the same or different materials.

Figure 2:
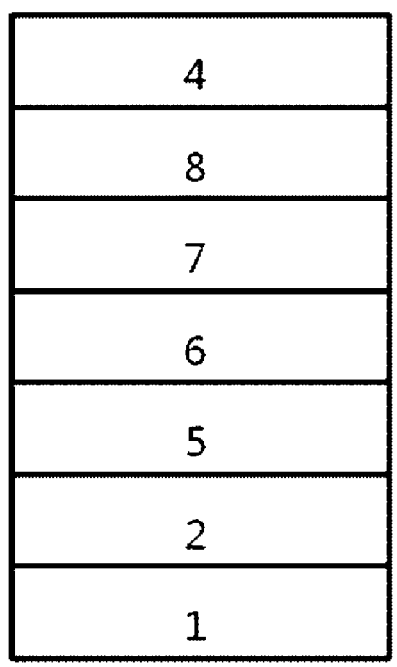
FIG. 2 shows an example of an organic light-emitting device consisting of a substrate 1, an anode 2, a hole-injecting layer 5, a hole-transporting layer 6, a light-emitting layer 7, an electron-transporting layer 8 and a cathode 4.

In an embodiment of the present disclosure, the organic electronic device may have the structures shown in FIGS. 1 and 2, but is not limited thereto.

FIG. 1 illustrates an organic electronic device having a structure in which a substrate 1, an anode 2, a light-emitting layer 3 and a cathode 4 are sequentially deposited. In this structure, the compound of formula 1 may be included in the light-emitting layer 3.

FIG. 2 illustrates an organic electronic device having a structure in which a substrate 1, an anode 2, a hole-injecting layer 5, a hole-transporting layer 6, a light-emitting layer 7, an electron-transporting layer 8 and a cathode 4 are sequentially deposited. In this structure, the compound represented by formula 1 may be included in one or more of the hole-injecting layer 5, the hole-transporting layer 6, the light-emitting layer 7 and the electron-transporting layer 8.

The organic electronic device according to the present disclosure can be fabricated using the same materials and methods as known in the art, except that one or more of the organic material layers may comprise the compound of the present disclosure, that is, the compound of formula 1.

For example, the organic electronic device according to the present disclosure can be fabricated by sequentially depositing a first electrode, one or more organic material layers and a second electrode on a substrate. Specifically, the organic electronic device can be fabricated by depositing a metal, a conductive metal oxide or an alloy thereof on a substrate using a physical vapor deposition (PVD) method such as sputtering or e-beam evaporation to form an anode, forming organic material layers, including a hole-injecting layer, a hole-transporting layer, a light-emitting layer and an electron-transporting layer, on the anode, and then depositing thereon a material that may be used to form a cathode. In addition, the organic electronic device may also be fabricated by sequentially depositing a cathode material, one or more organic material layers and an anode material on the substrate.

In addition, during the fabrication of the organic electronic device, the compound of formula 1 can be formed into an organic material layer using a solution application method in addition to the physical vacuum deposition method. As used herein, the term "solution application method" refers to spin coating, dip coating, doctor blading, inkjet printing, screen printing, spraying, roll coating or the like, but is not limited thereto.

In addition, the organic electronic device can also be fabricated by sequentially depositing a cathode material, organic material layers and an anode material on a substrate (International Patent Application Publication No. WO 2003/012890). However, the fabrication method is not limited to the above methods.

The anode material is preferably a material having a high work function, so that holes can be easily injected into the organic layers. Specific examples of an anode material that may be used in the present invention include, but are not limited to, metals such as vanadium, chromium, copper, zinc or gold, or alloys thereof; metal oxides such as zinc oxide, indium oxide, indium tin oxide (ITO) or indium zinc oxide (IZO); metal/oxide combinations such as $ZnO:Al$ or $SnO_2:Sb$; and conductive polymers such as poly(3-methylthiophene), poly[3,4-(ethylene-1,2-dioxy)thiophene] (PEDOT), polypyrrole and polyaniline.

The cathode material is preferably a material having a low work function, so that electrons are easily injected into the organic layers. Specific examples of the cathode material include, but are not limited to, metals such as magnesium, calcium, sodium, potassium, titanium, indium, yttrium, lithium, gadolinium, aluminum, silver, tin and lead, or alloys thereof; and multilayer materials such as LiF/Al or $LiO_2$/Al.

The hole-injecting material is a material that can easily receive holes from the anode at a low voltage, and the HOMO (highest occupied molecular orbital) of the hole-injecting material is preferably between the work function of the anode material and the HOMO of the surrounding organic material layers. Specific examples of the hole-injecting material include, but are not limited to, metal porphyrin, oligothiophene, and arylamine-based organic materials, hexanitrile hexaazatriphenylene and quinacridone-based organic materials, perylene-based organic materials, anthraquinone, polyaniline-based or polythiophene-based conductive polymers and the like.

The hole-transporting material is preferably a material having high hole mobility, which is capable of transferring holes from the anode or the hole-injecting layer to the light-emitting layer. Specific examples of the hole-transporting material include, but are not limited to, arylamine-based organic materials, conductive polymers, and block copolymers having both conjugated portions and non-conjugated portions.

The light-emitting material is a material capable of emitting visible light by receiving holes and electrons from the hole-transporting layer and from the electron-transporting layer and combining the received holes and electrons and is preferably a material having high quantum efficiency for fluorescence and phosphorescence. Specific examples of the light emitting material include, but are not limited to, a 8-hydroxyquinoline aluminum, complex ($Alq_3$); carbazole-based compounds; dimerized styryl compounds; BAlq; 10-hydroxybenzoquinoline-metal compounds; benzoxazole-, benzthiazole- and benzimidazole-based compounds; poly(p-phenylenevinylene) (PPV)-based polymers; spiro compounds; and compounds such as polyfluorene and rubrene.

The electron-transporting material is a material that can easily receive electrons from the cathode and transfer the received electrons to the light-emitting layer. It is preferably a material having high electron mobility. Specific examples of the electron-transporting material include, but are not limited to, an 8-hydroxyquinoline aluminum, complex; complexes including $Alq_3$; organic radical compounds; and hydroxyflavone-metal complexes.

The organic electronic device according to the present disclosure may be a front side light-emitting type, a rear side light-emitting type or a both-side light-emitting type, depending on the material used

EXAMPLES

Hereinafter, the present disclosure will be described in further detail with reference to Preparation Examples and Experimental Examples, but the scope of the present disclosure is not limited by these Preparation Examples and Experimental Examples.

Preparation Examples

Preparation Example 1

Preparation of Compound 1-a-1

1) Synthesis of Compound 1-A

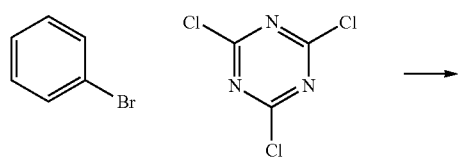

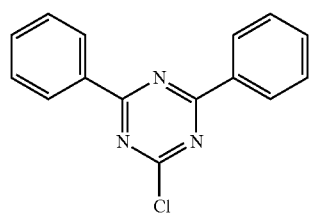

[Compound 1-A]

Magnesium (9.7 g, 0.40 mol) and iodine (1.02 g, 8 mmol) were suspended in 80 ml of an anhydrous tetrahydrofuran solvent in a nitrogen atmosphere to prepare a suspension, and a solution of bromobenzene (62.8 g, 0.4 mol) in 150 ml of anhydrous tetrahydrofuran was slowly added dropwise to the suspension over 1 hour. The mixture was heated under reflux for 3 hours. The mixture was cooled to room temperature, and then a solution of 1,3,5-trichlorotriazine (27.6 g, 0.15 mol) in 150 ml of anhydrous tetrahydrofuran was slowly added dropwise to the mixture, which was then stirred under reflux for about 5 hours. After completion of the reaction, the organic solvent in the reaction solution was removed by distillation under reduced pressure, and the residue was recrystallized from ethanol, thereby obtaining compound 1-A (39 g, yield: 73.5%).

MS [M+H]$^+$=268

2) Synthesis of Compound 1-B

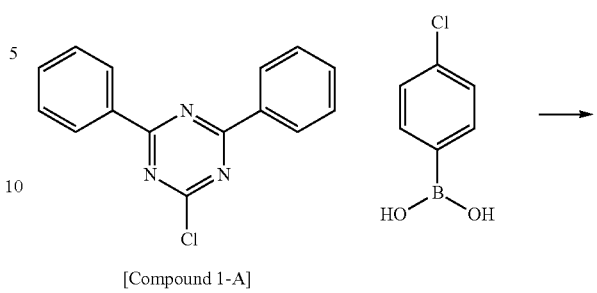

[Compound 1-A]

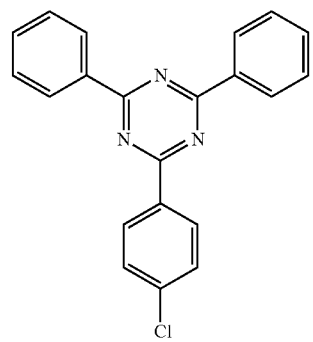

[Compound 1-B]

Compound 1-A (37.1 g, 0.14 mol) and 4-chlorophenylboronic acid (23.8 g, 0.15 mol) were completely dissolved in 150 ml of tetrahydrofuran in a nitrogen atmosphere, and then 80 ml of a 2M aqueous solution of potassium carbonate was added thereto and tetrakis-(triphenylphosphine)palladium (3.2 g, 2.7 mmol) was added thereto. Then, the mixture was heated with stirring for 5 hours. The temperature of the mixture was lowered to room temperature, and the aqueous layer was removed. The residue was dried with anhydrous magnesium sulfate, concentrated under reduced pressure, and purified by column chromatography using tetrahydrofuran: hexane=1:6, thereby obtaining compound 1-B (34 g, yield: 72%).

MS [M+H]$^+$=344

3) Synthesis of Compound 1-C

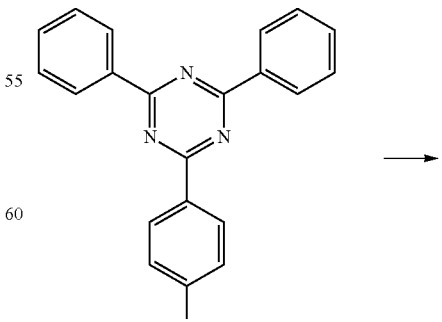

[Compound 1-B]

-continued

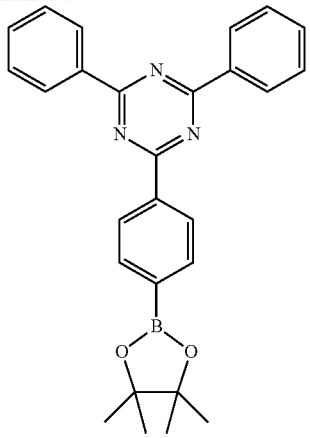

[Compound 1-C]

Compound 1-B (34 g, 98.9 mmol), bis(pinacolate)diboron (27.6 g, 108 mmol) and potassium acetate (29.1 g, 296 mmol) were mixed with each other in a nitrogen atmosphere, and the mixture was added to 100 ml of dioxane and heated with stirring. Bis(dibenzylideneacetone)palladium (1.7 g, 2.94 mmol) and tricyclohexylphosphine (1.6 g, 5.9 mmol) were added to the mixture under reflux and heated with stirring for 10 hours. After completion of the reaction, the reaction solution was cooled to room temperature and filtered. The filtrate was added to water and extracted with chloroform, and the organic layer was dried with anhydrous magnesium sulfate. The resulting material was distilled under reduced pressure and recrystallized from ethanol, thereby obtaining compound 1-C (35 g, yield: 81%).

MS [M+H]$^+$=436

4) Synthesis of Compound 1-a-1

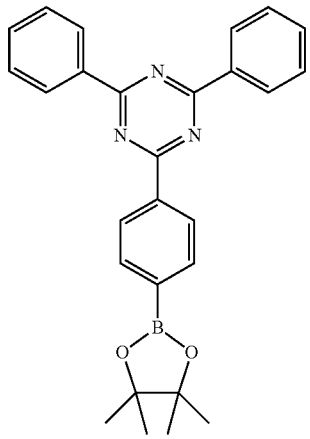 

[Compound 1-C]

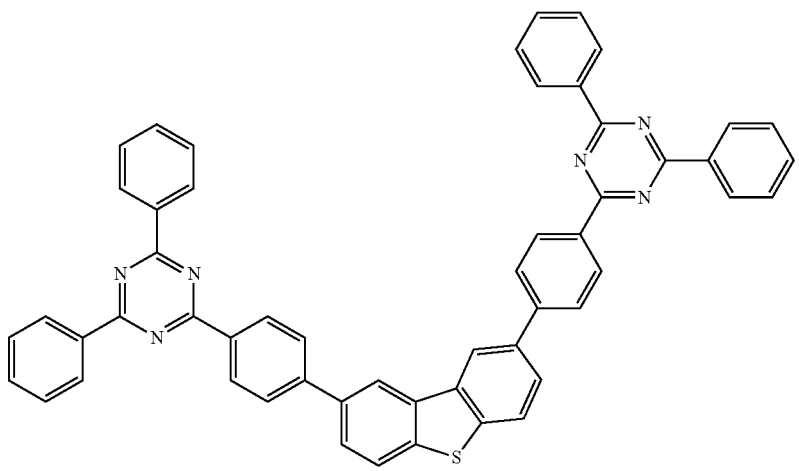

[Compound 1-a-1]

Compound 1-C (16.4 g, 37.7 mmol) and 3,6-dibromodibenzothiophene (12.8 g, 37.7 mmol) were completely dissolved in tetrahydrofuran (50 ml), and a 2M potassium carbonate aqueous solution (30 ml) and tetrakistriphenylphosphine palladium (400 mg, 0.34 mmol) were added thereto. The mixture was heated with stirring for 2 hours. Then, the mixture was cooled to room temperature to complete the reaction, after which the potassium carbonate solution was removed and the white solid was filtered. The white solid was washed once with each of tetrahydrofuran and ethanol, thereby obtaining compound 1-a-1 (19.8 g, yield: 65%).

MS [M+H]$^+$=799

Preparation Example 2

Preparation of Compound 1-b-1

1) Synthesis of Compound 1-b-1

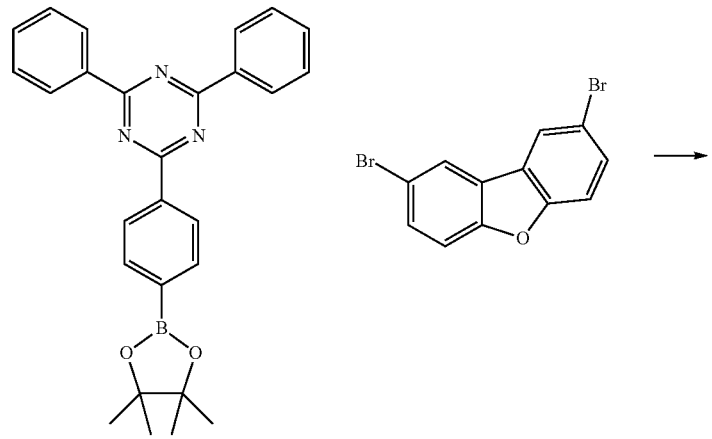

[Compound 1-B]

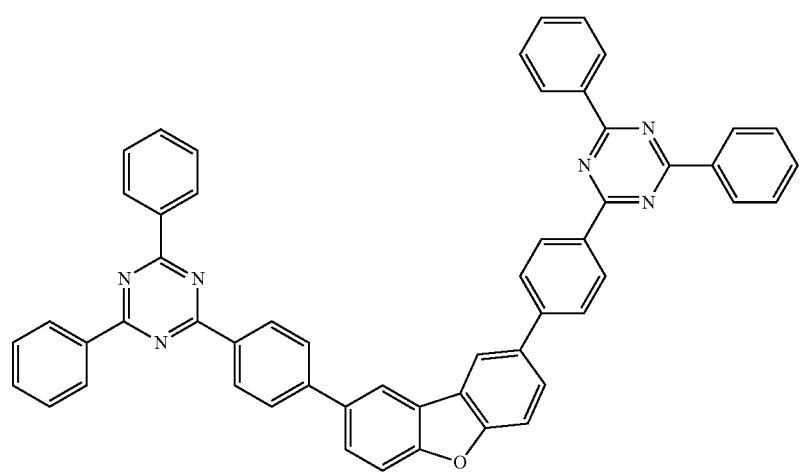

[Compound 1-b-1]

Compound 1-b-1 was prepared in the same manner as compound I-a-1, except that 3,6-dibromodibenzofuran was used instead of 3,6-dibromodibenzothiophene.

MS [M+H]$^+$=783

Preparation Example 3

Preparation of Compound 1-c-1

1) Synthesis of Compound 1-c-1

[Compound 1-C]

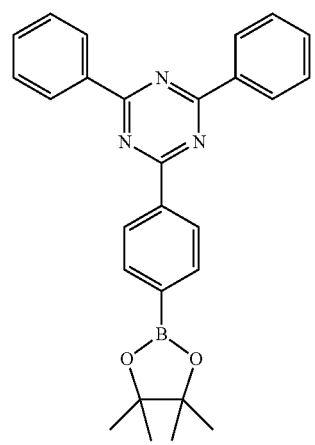

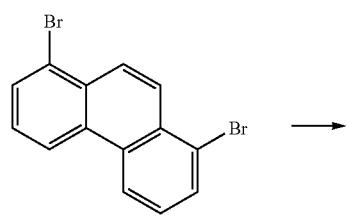

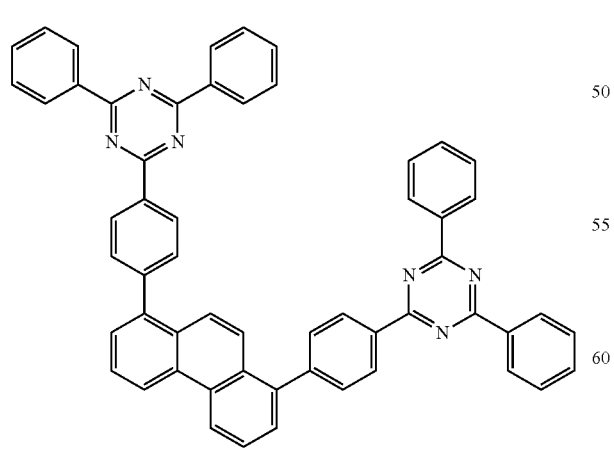

[Compound 1-c-1]

Compound 1-c-1 was prepared in the same manner as compound 1-a-1, except that 1,8-dibromophenanthrene was used instead of 3,6-dibromodibenzothiophene.

MS [M+H]$^+$=793

Preparation Example 4

Preparation of Compound 1-d-1

1) Synthesis of Compound 1-d-1

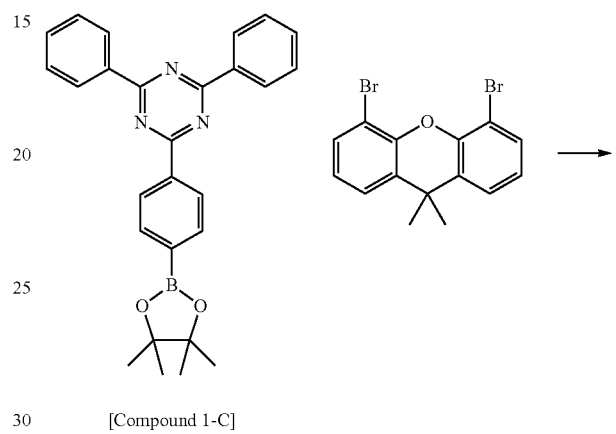

[Compound 1-C]

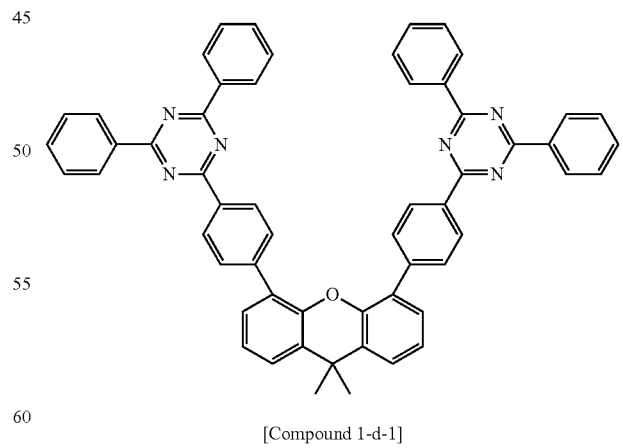

[Compound 1-d-1]

Compound 1-d-1 was prepared in the same manner as compound 1-a-1, except that 4,5-dibromo-9,9-dimethyl-9H-xanthene was used instead of 3,6-dibromodibenzothiophene.

MS [M+H]$^+$=825

Preparation Example 5
Preparation of Compound 1-e-1
1) Synthesis of Compound 1-e-1
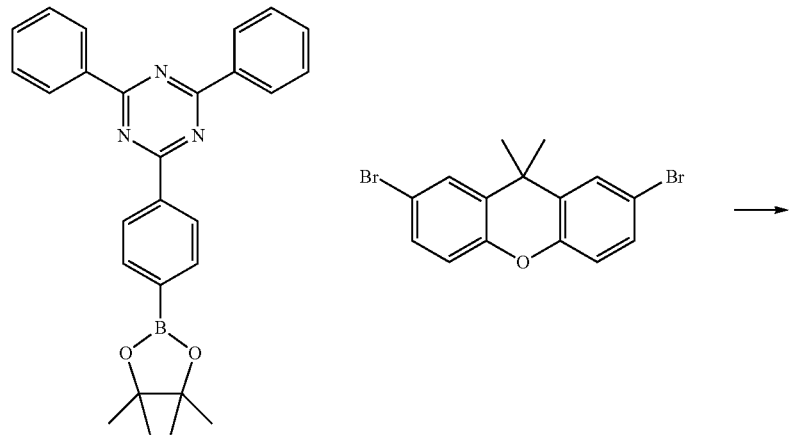
[Compound 1-C]
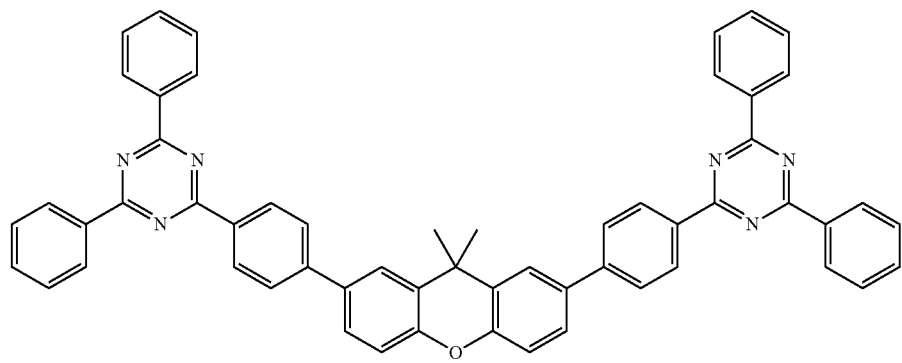
[Compound 1-e-1]

Compound 1-e-1 was prepared in the same manner as compound 1-a-1, except that 2,7-dibromo-9,9-dimethyl-9H-xanthene was used instead of 3,6-dibromodibenzothiophene.
MS [M+H]$^+$=825

Preparation Example 6

Preparation of Compound 1-f-1

1) Synthesis of Compound 1-f-1

[Compound 1-C]

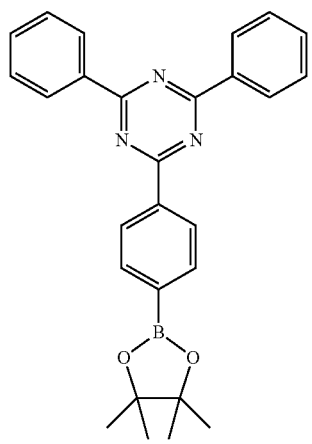

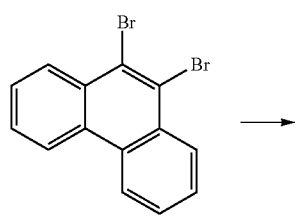

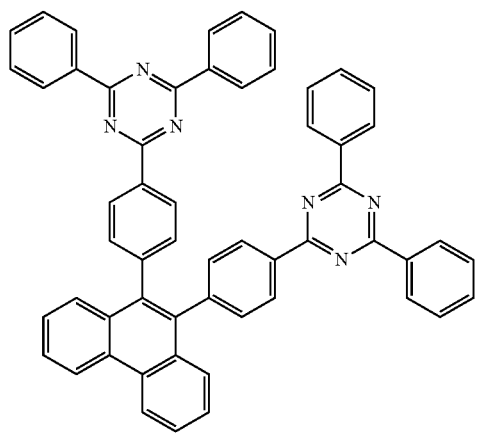

[Compound 1-f-1]

Compound 1-f-1 was prepared in the same manner as compound 1-a-1, except that 9,10-dibromophenanthrene was used instead of 3,6-dibromodibenzothiophene.
MS [M+H]$^+$=793

Experimental Example 1

A glass substrate having ITO (indium tin oxide) coated thereon to a thickness of 1,000 Å was placed in distilled water containing a detergent dissolved therein and was ultrasonically washed. Herein, the detergent was a product manufactured by Fischer Co., and the distilled water was distilled water filtered twice through a filter (Millipore Co.). After the ITO has been washed for 30 minutes, it was ultrasonically washed twice with distilled water for 10 minutes. After the completion of washing with distilled water, the substrate was ultrasonically washed with a solvent such as isopropyl alcohol, acetone, methanol or the like, and was dried, after which it was transported to a plasma cleaner. Then, the substrate was cleaned with oxygen plasma for 5 minutes, and then transferred to a vacuum evaporator.

On the transparent ITO electrode fabricated as described above, hexaazatriphenylene (HAT) having the following formula was deposited to a thickness of 500 Å by a thermal vacuum deposition method to form a hole-injecting layer:

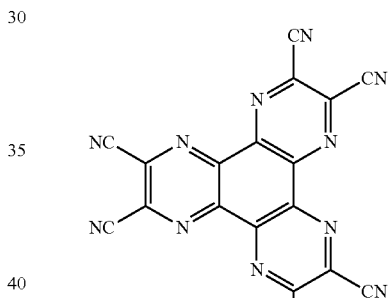

[HAT]

On the hole-injecting layer, 4-4'-bis[N-(1-naphthyl)-N-phenylamino]biphenyl (NPB) of the following formula, which is a hole-transporting material, was vacuum-deposited to a thickness of 400 Å to form a hole-transporting layer:

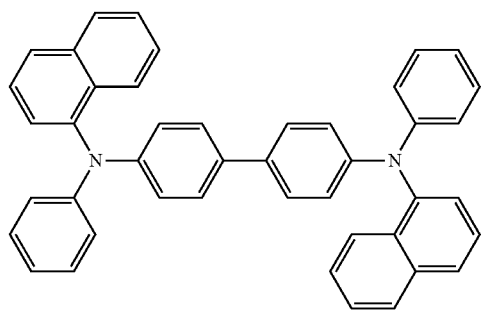

[NPB]

On the hole-transporting layer, a 25:1 (w/w) mixture of BH and BD, which have the following formulas, was vacuum-deposited to a thickness of 300 Å to form a light-emitting layer:

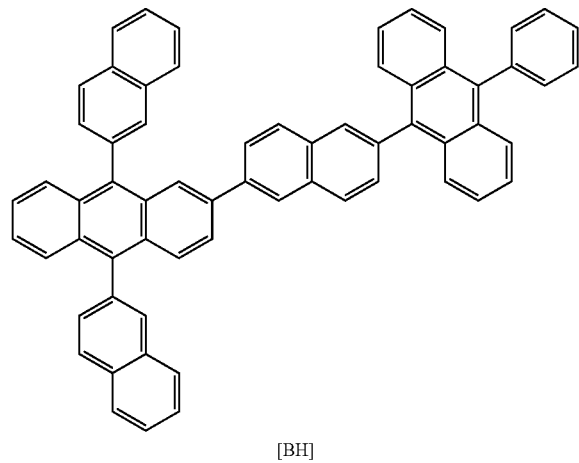

[BH]

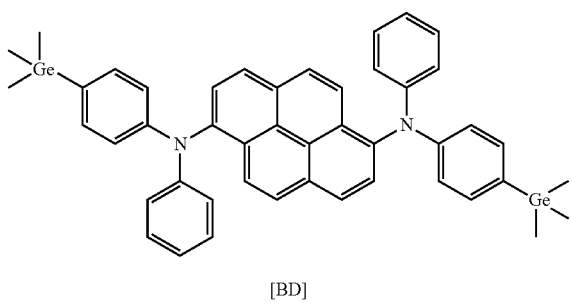

[BD]

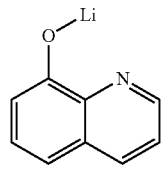

[LiQ]

On the light-emitting layer, a 1:1 (w/w) mixture of compound 1-a-1, prepared in Preparation Example 1 as shown above, and lithium quinolate (LiQ), was vacuum-deposited to a thickness of 300 Å to form an electron-injecting and electron-transporting layer. On the electron-injecting and electron-transporting layer, lithium fluoride (LiF) and aluminum were sequentially deposited to thicknesses of 12 Å and 2,000 Å, respectively, to form a cathode.

In the above process for fabricating the organic light-emitting device, the deposition rate of the organic materials was maintained at 0.4-0.7 Å/sec, the deposition rates of lithium fluoride and aluminum for the cathode were maintained at 0.3 Å/sec and 2 Å/sec, respectively, and the strength of vacuum during the deposition was maintained at $2 \times 10^{-7}$ to $5 \times 10^{-6}$ torr.

Experimental Example 2

An organic light-emitting device was fabricated in the same manner as described in Experimental Example 1, except that compound 1-b-1 was used instead of compound 1-a-1.

Experimental Example 3

An organic light-emitting device was fabricated in the same manner as described in Experimental Example 1, except that compound 1-c-1 was used instead of compound 1-a-1.

Experimental Example 4

An organic light-emitting device was fabricated in the same manner as described in Experimental Example 1, except that compound 1-d-1 was used instead of compound 1-a-1.

Experimental Example 5

An organic light-emitting device was fabricated in the same manner as described in Experimental Example 1, except that compound 1-e-1 was used instead of compound 1-a-1.

Experimental Example 6

An organic light-emitting device was fabricated in the same manner as described in Experimental Example 1, except that compound 1-f-1 was used instead of compound 1-a-1.

Comparative Example 1

An organic light-emitting device was fabricated in the same manner as described in Experimental Example 1, except that the following compound ET1 was used instead of compound 1-a-1:

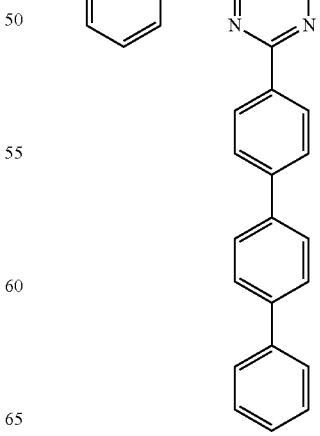

[ET1]

Comparative Example 2

An organic light-emitting device was fabricated in the same manner as described in Experimental Example 1, except that the following compound ET2 was used instead of compound 1-a-1:

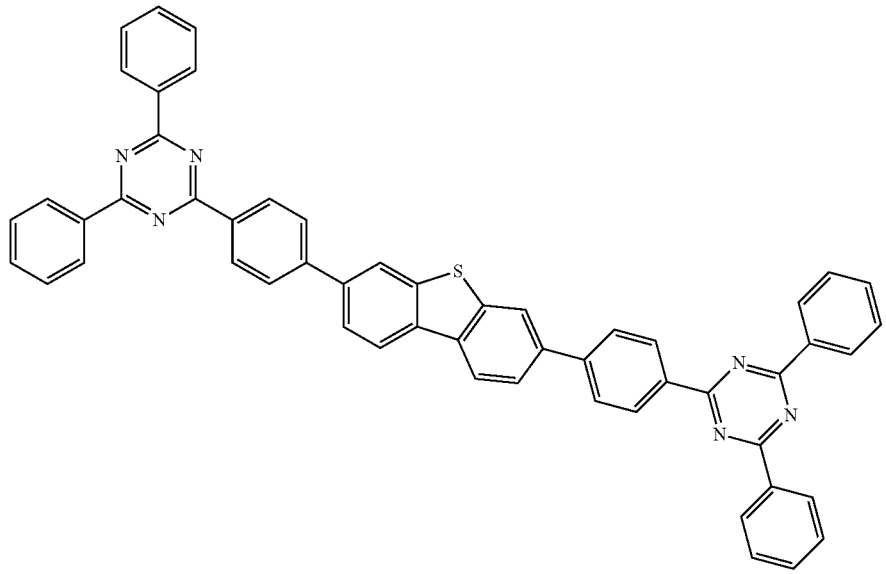

[ET2]

Comparative Example 3

An organic light-emitting device was fabricated in the same manner as described in Experimental Example 1, except that the following compound ET3 was used instead of compound 1-a-1:

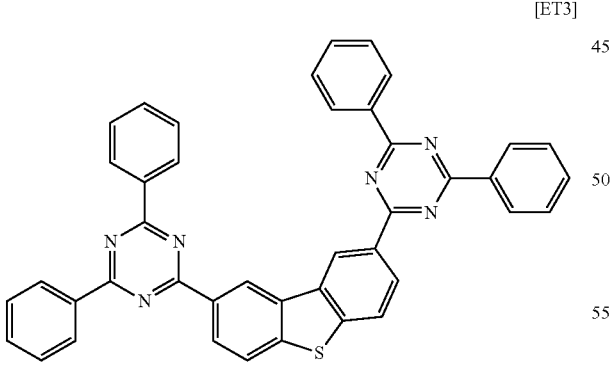

[ET3]

Comparative Example 4

An organic light-emitting device was fabricated in the same manner as described in Experimental Example 1, except that the following compound ET4 was used instead of compound 1-a-1:

[ET4]

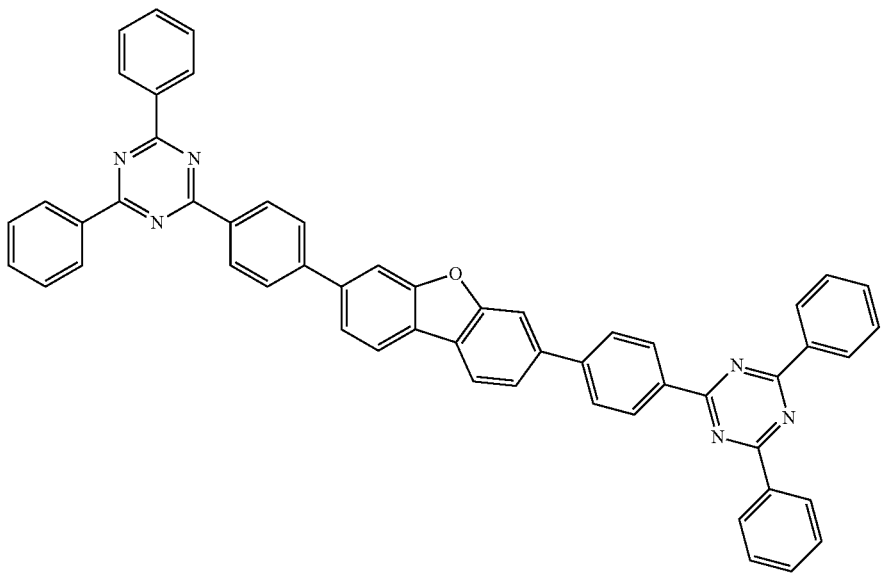

When an electric current was applied to each of the organic light-emitting devices fabricated in Experimental Examples 1 to 4 and Comparative Examples 1 to 4, the results shown in Table 1 below were obtained.

TABLE 1

| | Compound | Voltage (V @ 10 mA/cm$^2$) | Efficiency (cd/A @ 10 mA/cm$^2$) | Color coordinates (x, y) |
|---|---|---|---|---|
| Experimental Example 1 | Compound 1-a-1 | 3.74 | 5.11 | (0.139, 0.121) |
| Experimental Example 2 | Compound 1-b-1 | 3.93 | 5.28 | (0.138, 0.126) |
| Experimental Example 3 | Compound 1-c-1 | 3.64 | 5.13 | (0.138, 0.128) |
| Experimental Example 4 | Compound 1-d-1 | 3.71 | 5.09 | (0.132, 0.131) |
| Experimental Example 5 | Compound 1-e-1 | 3.83 | 4.72 | (0.136, 0.133) |
| Experimental Example 6 | Compound 1-f-1 | 3.99 | 5.01 | (0.137, 0.128) |
| Comparative Example 1 | ET1 | 4.02 | 3.95 | (0.136, 0.130) |
| Comparative Example 2 | ET2 | 4.21 | 3.72 | (0.133, 0.126) |
| Comparative Example 3 | ET3 | 4.16 | 4.05 | (0.136, 0.133) |
| Comparative Example 4 | ET4 | 4.25 | 3.67 | (0.133, 0.125) |

As can be seen in Table 1 above, the comparison between Experimental Example 1 and Comparative Example 2 indicated that the ability of 3,6-dibenzothiophene to transport and inject electrons is excellent compared to that of 2,7-dibenzothiophene.

As can be seen in Table 1 above, the comparison between Experimental Example 2 and Comparative Example 4 indicated that the ability of 3,6-dibenzofuran to transport and inject electrons is excellent compared to that of 2,7-dibenzofuran.

As can be seen in Table 1 above, the comparison between Experimental Example 1 and Comparative Example 3 indicated that the ability to transport and inject electrons is excellent when L is an aryl group compared to when L is not a direct bond.

The results in Table 1 above indicate that the compound according to the present disclosure has an excellent ability to transport and inject electrons, suggesting that it can be applied to an organic light-emitting device.

The invention claimed is:

1. A heterocyclic compound represented by the following formula 1:

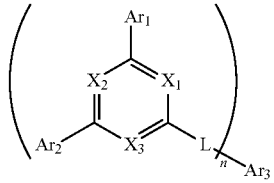

Formula 1 wherein n is 2, $X_1$ to $X_3$ are the same or different, and are each independently N or CH, and at least one of $X_1$ to $X_3$ is N, $Ar_1$ and $Ar_2$ are the same or different, and are each independently selected from the group consisting of a phenyl group unsubstituted or substituted with substituent groups selected from the group consisting of an alkyl group having 1 to 50 carbon atoms unsubstituted or substituted a halogen group, an alkoxy group, an alkenyl group having 1 to 50 carbon atoms, a halogen group and a phenyl group, L is a substituted or unsubstituted arylene group, and $Ar_3$ is selected from the group consisting of a substituted or unsubstituted 9, 10-phenanthryl group, a substituted or unsubstituted 2,7-phenanthryl group, a substituted or unsubstituted 1,8-phenanthryl group, a substituted or unsubstituted 3,6-dibenzothiophene group, a substituted or unsubstituted 3,6-dibenzofuran group, a substituted or unsubstituted 1,8-dibenzothiophene group, a substituted or unsubstituted 1,8-dibenzofuran group, a substituted or unsubstituted tetracenyl group, a substituted or unsubstituted fluoranthene group, a substituted or unsubstituted xanthene group and a substituted or unsubstituted acenaphthyl group; and wherein the substituted or unsubstituted means that it is unsubstituted or substituted with one or more substituents selected from the group consisting of deuterium; a halogen group; an alkyl group; an alkenyl group; an alkoxy group; a cycloalkyl group; a silyl group; an arylalkenyl group; an aryl group; an aryloxy group; an alkylthioxy group; an alkylsulfoxy group; an arylsulfoxy group; a boron group; an alkylamine group; an aralkylamine group; an arylamine group; a heteroaryl group; a carbazole group; a fluorenyl group; a nitrile group; a nitro group; a hydroxyl group; a cyano group; and a heterocyclic group containing at least one heteroatom selected from among N, O, S and P.

2. The heterocyclic compound of claim 1, wherein $Ar_3$ is any one selected from among the following structures:

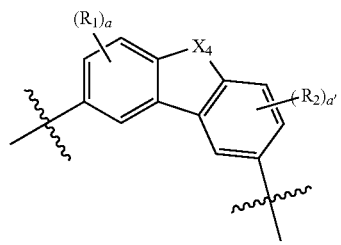

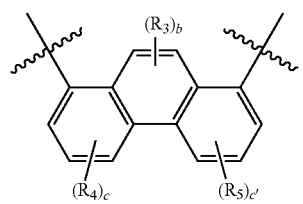

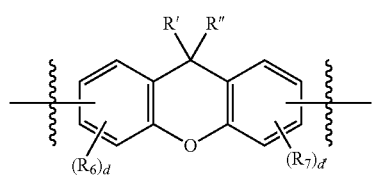

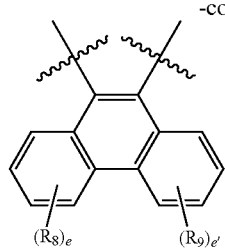

wherein a, a', c, c', d and d' are each an integer ranging from 1 to 3,
b is an integer ranging from 1 to 2,
e and e' are each an integer ranging from 1 to 4,
$X_4$ is S or O,
$R_1$ to $R_9$ are the same or different, and are each independently hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heterocyclic group containing at least one heteroatom selected from among N, O, S and P,
R' and R" are the same or different, and are each independently selected from the group consisting of hydrogen, deuterium, a halogen group, a nitrile group, a nitro group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, and a substituted or unsubstituted heterocyclic group containing at least one heteroatom selected from among N, O, S and P, or may form a condensed ring with an aliphatic, aromatic, aliphatic heterocyclic or aromatic heterocyclic ring, or form a spiro linkage.

3. The heterocyclic compound of claim 1, wherein L is a substituted or unsubstituted phenylene group.

4. The heterocyclic compound of claim 1, wherein the compound represented by formula 1 is any one of the following compounds 1-a-1 to 1-a-16 and 2-a-1 to 2-a-8:

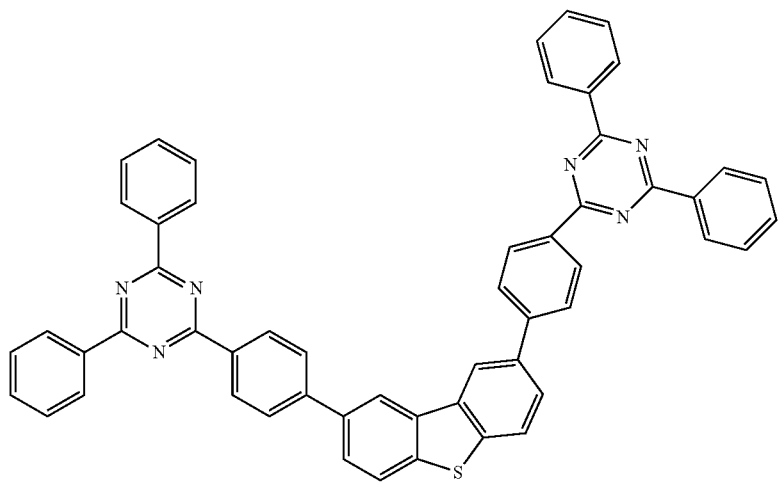
Compound 1-a-1
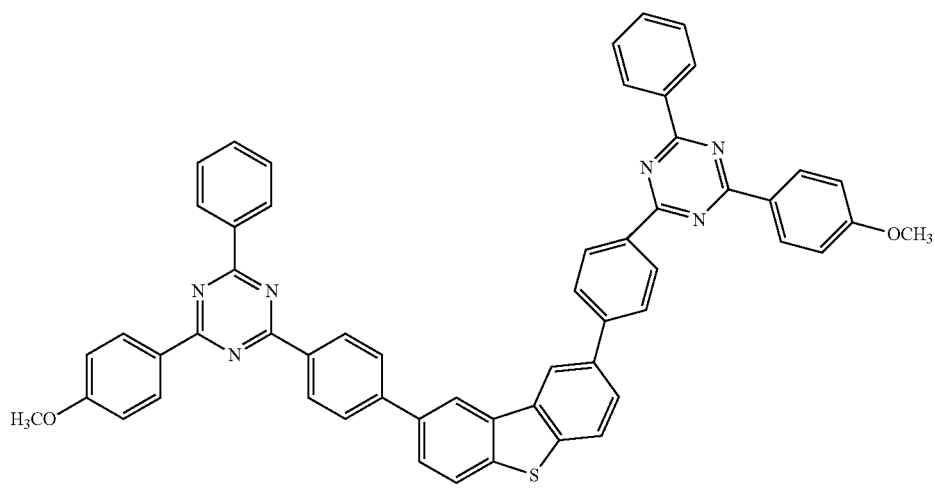
Compound 1-a-2
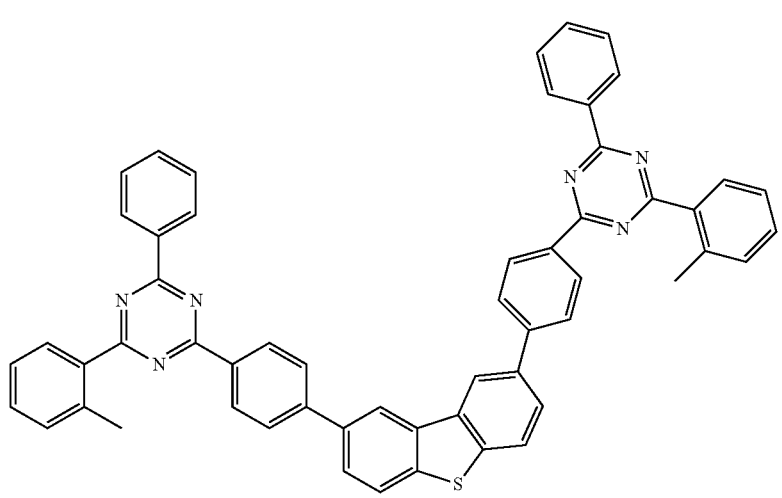
Compound 1-a-3

Compound 1-a-4
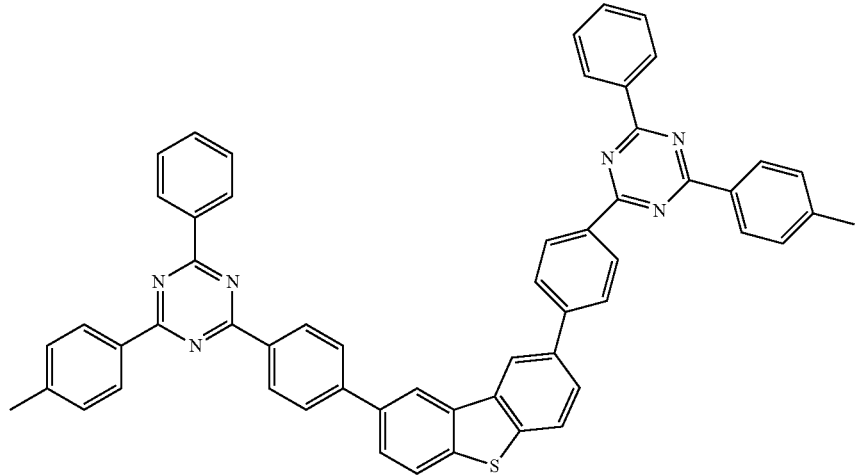
Compound 1-a-5
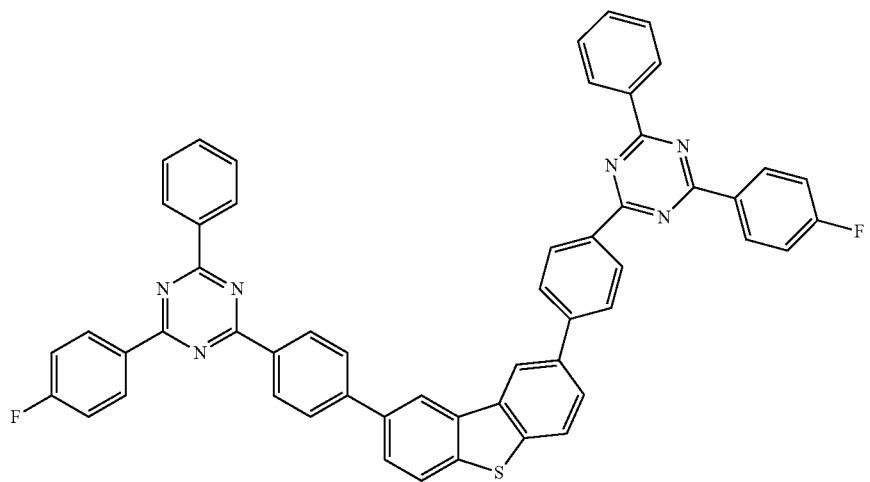
Compound 1-a-6
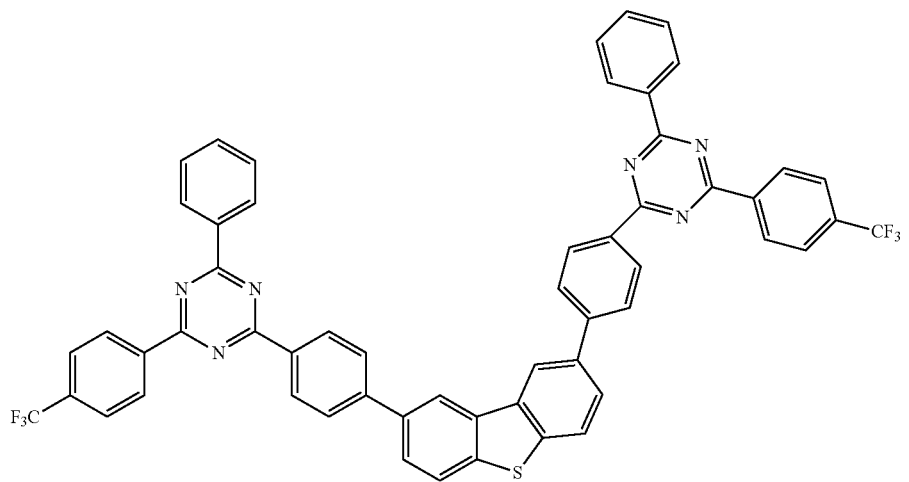

-continued
Compound 1-a-7
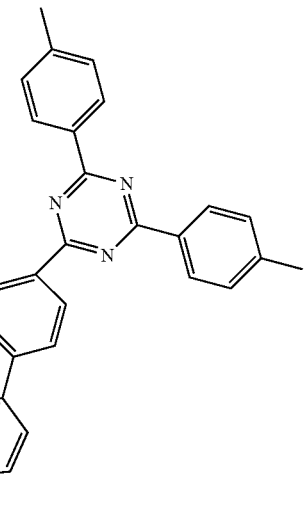
Compound 1-a-8
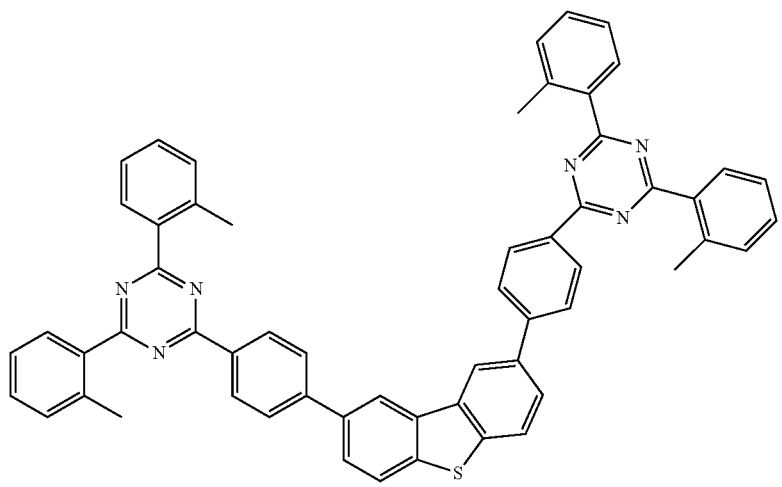
Compound 1-a-9
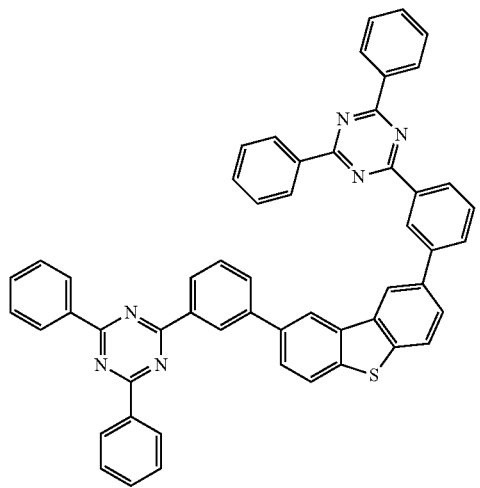
Compound 1-a-10
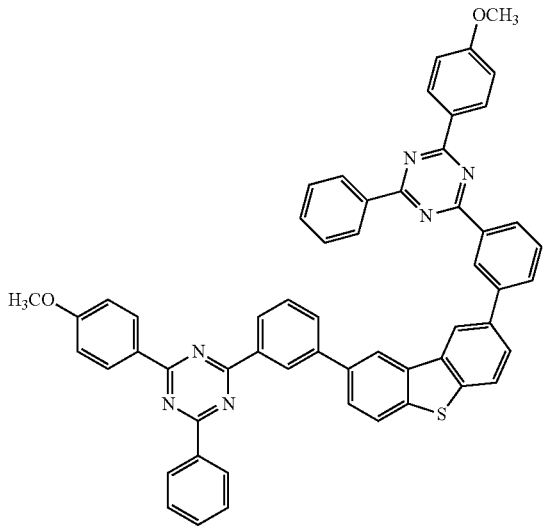

Compound 1-a-11
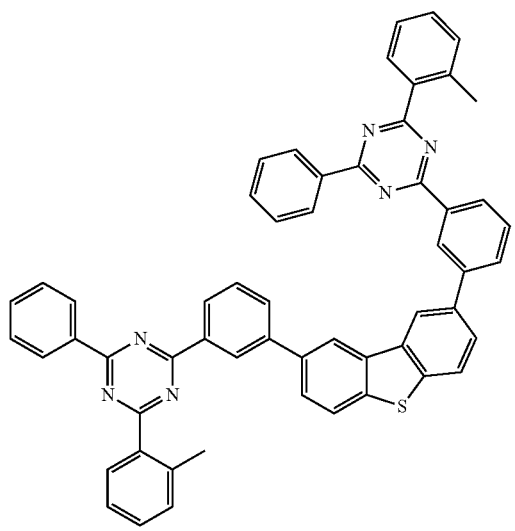
Compound 1-a-12
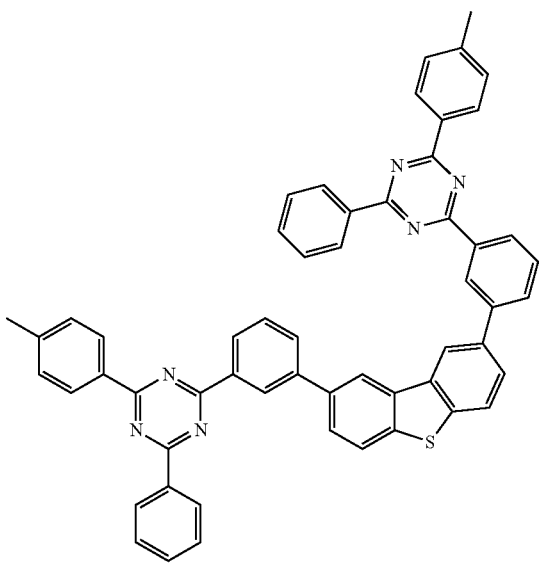
Compound 1-a-13
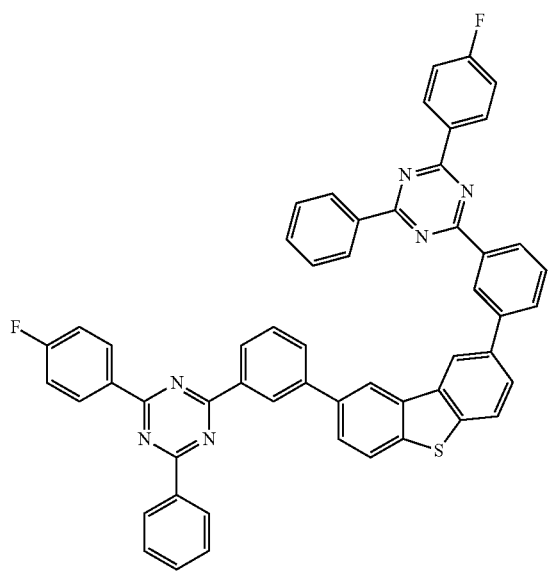
Compound 1-a-14
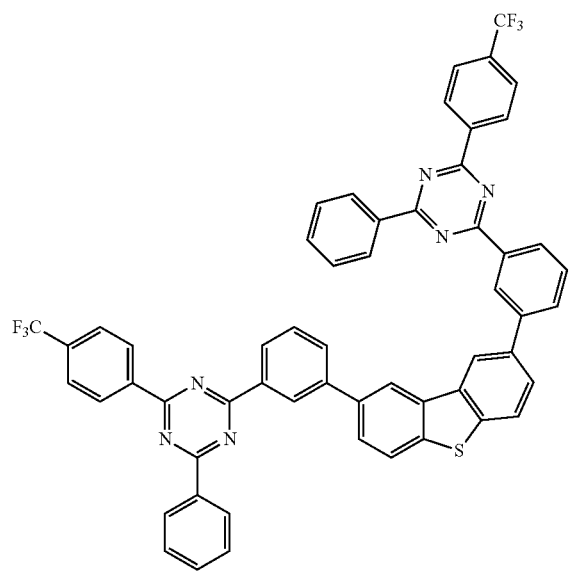

-continued
Compound 1-a-15
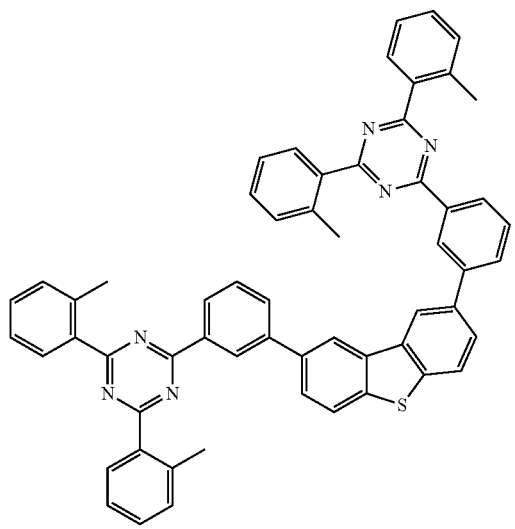
Compound 1-a-16
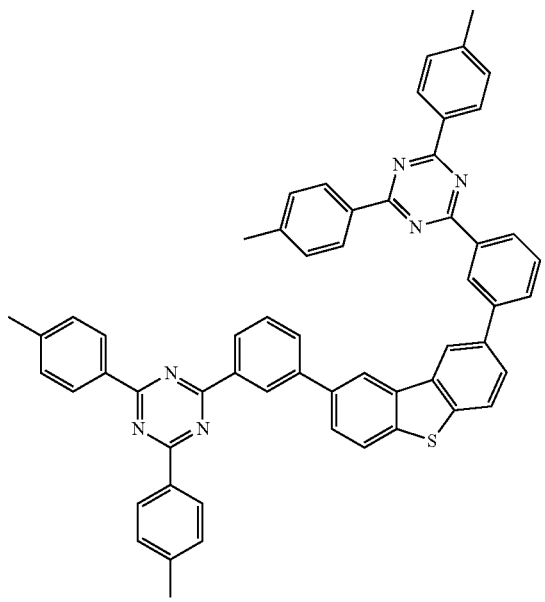
Compound 2-a-1
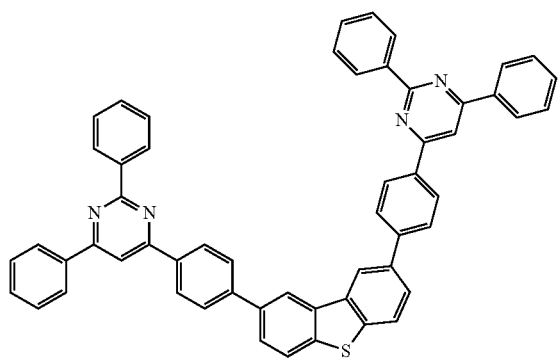
Compound 2-a-2
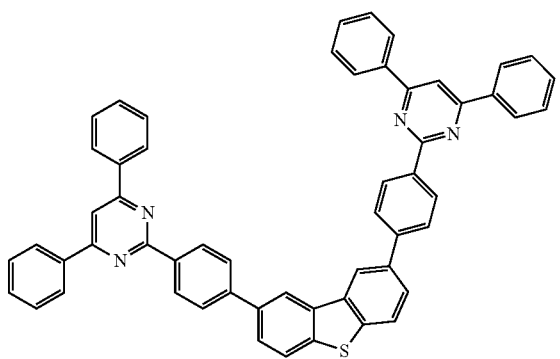
Compound 2-a-3
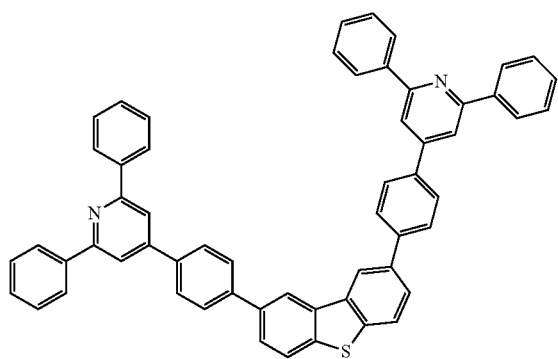
Compound 2-a-4
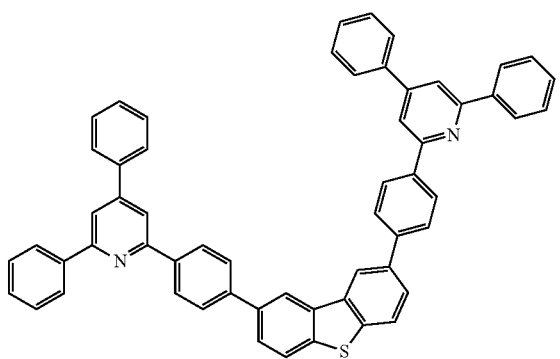

-continued
Compound 2-a-5
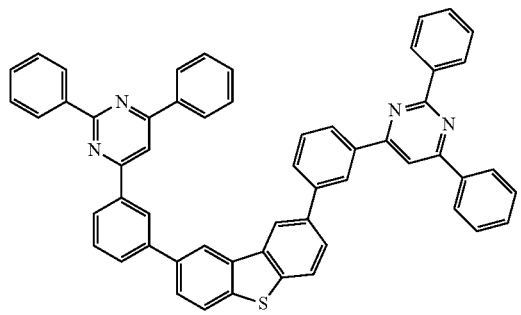
Compound 2-a-6
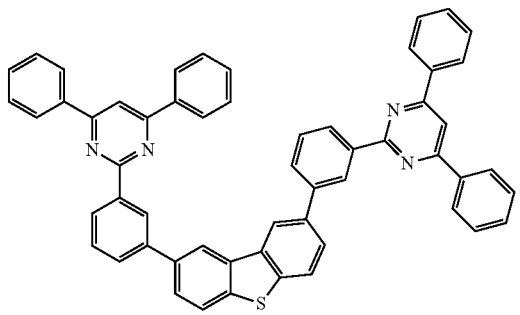
Compound 2-a-7
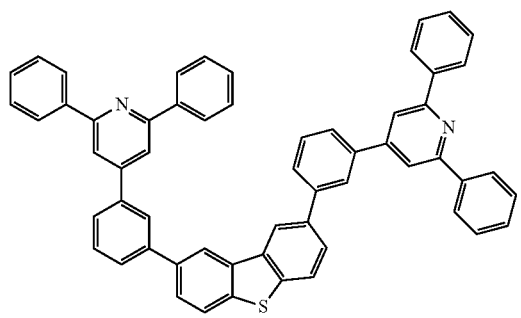
Compound 2-a-8
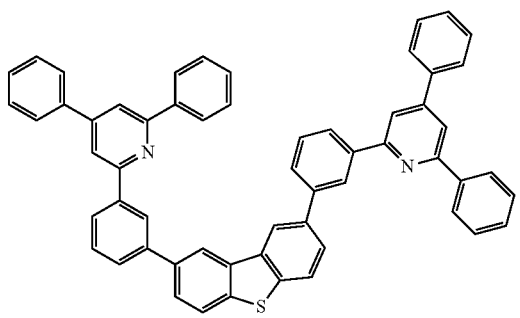
5. The heterocyclic compound of claim 1, wherein the compound represented by formula 1 is any one of the following compounds 1-b-1 to 1-b-16 and 2-b-1 to 2-b-8:
Compound 1-b-1
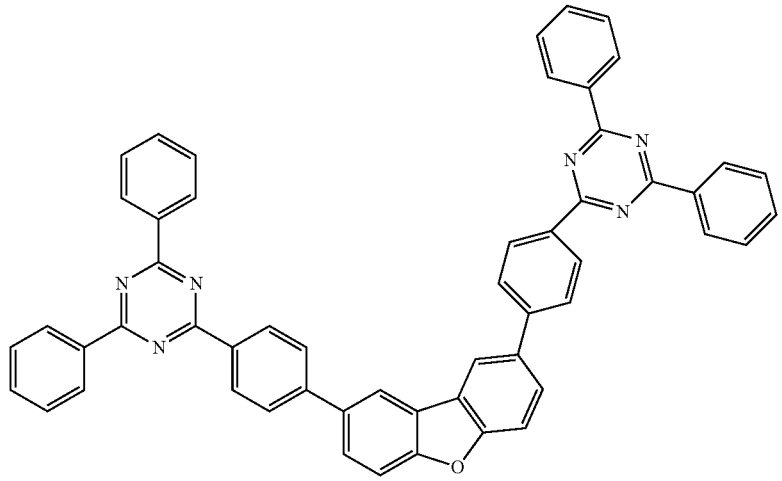

-continued
Compound 1-b-2
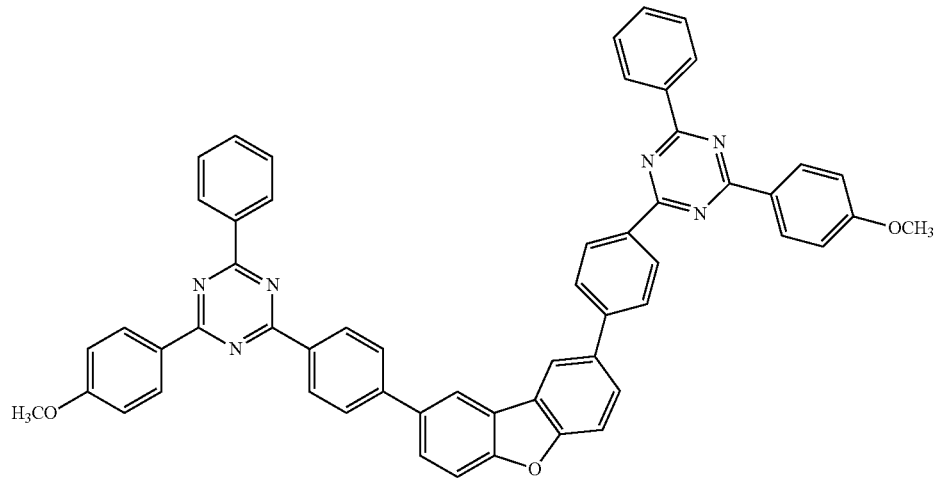
Compound 1-b-3
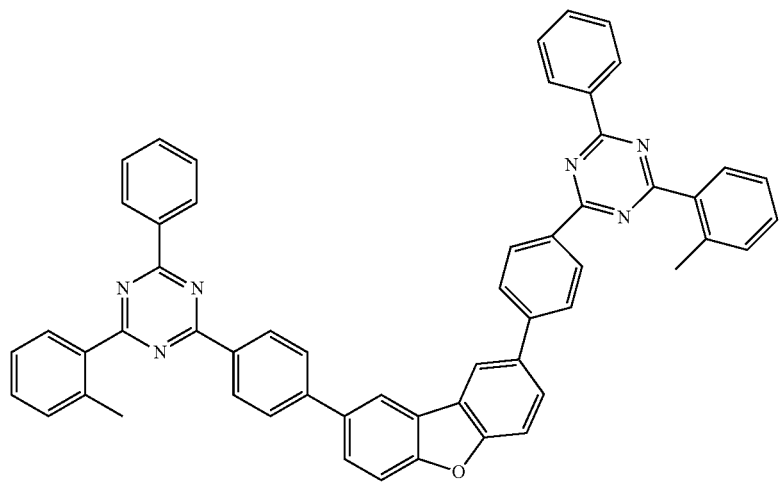
Compound 1-b-4
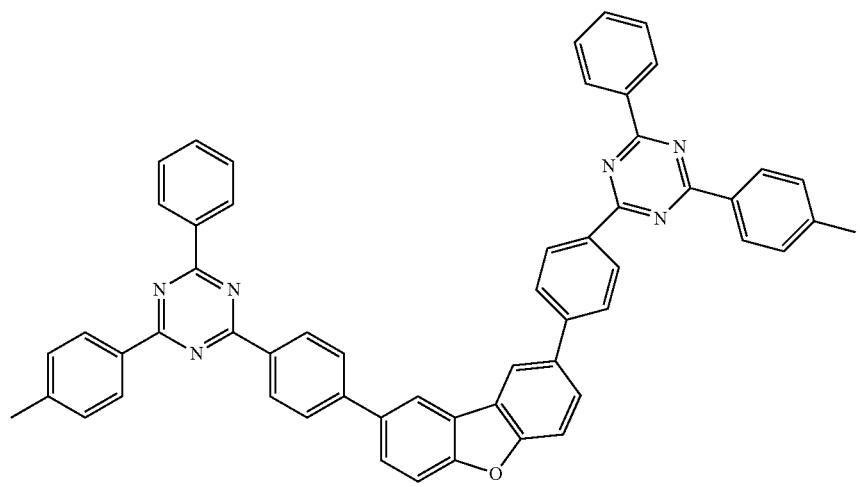

-continued
Compound 1-b-5
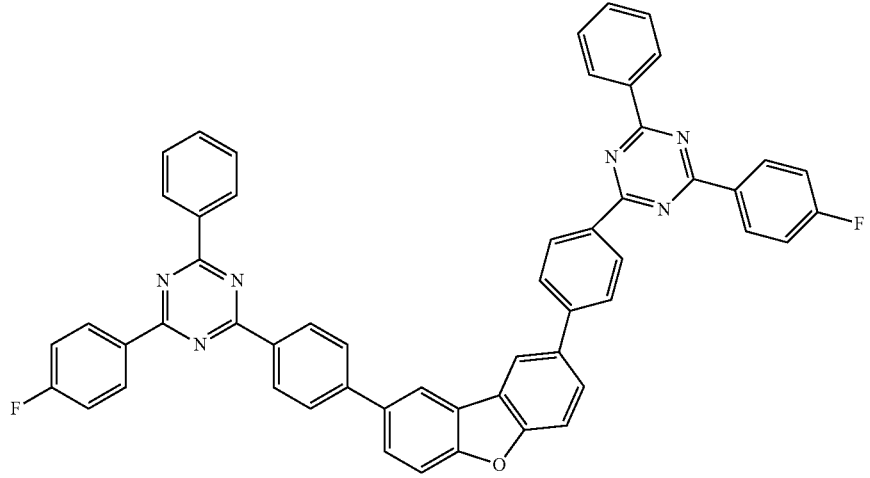
Compound 1-b-6
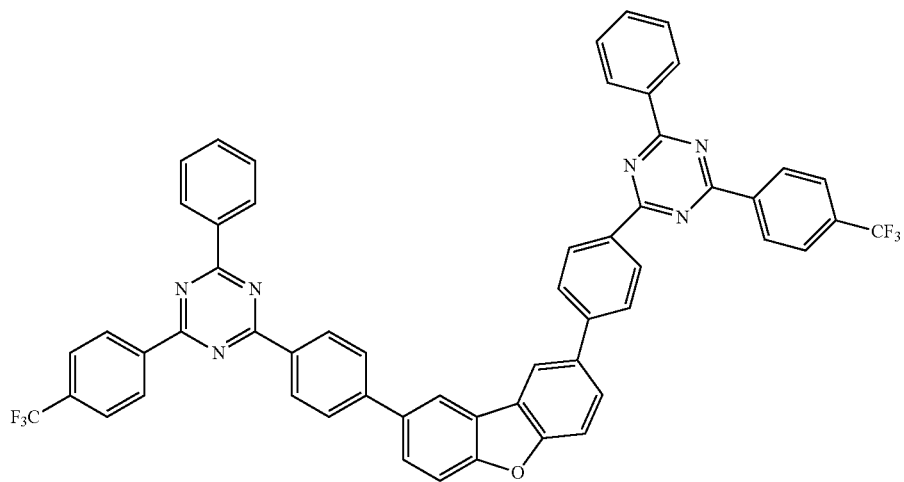
Compound 1-b-7
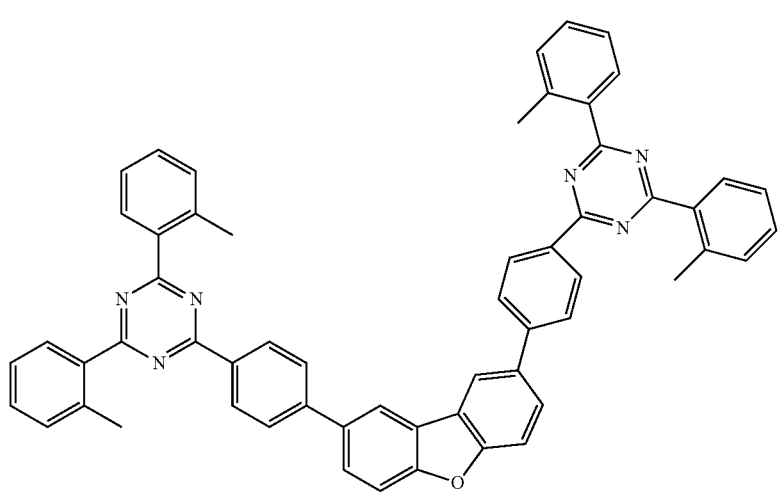

-continued
Compound 1-b-8
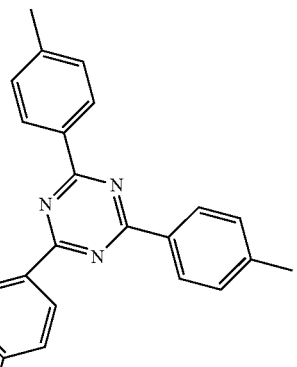
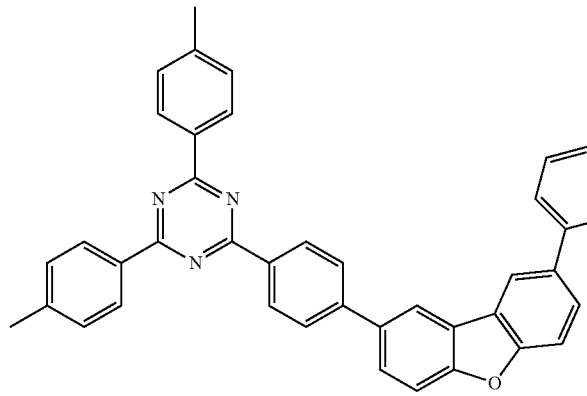
Compound 1-b-9
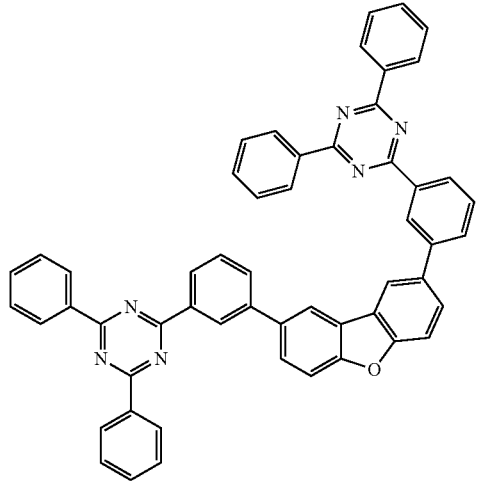
Compound 1-b-10
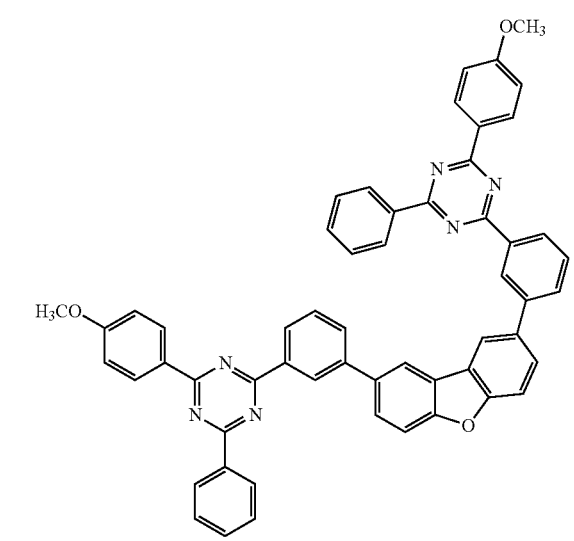
Compound 1-b-11
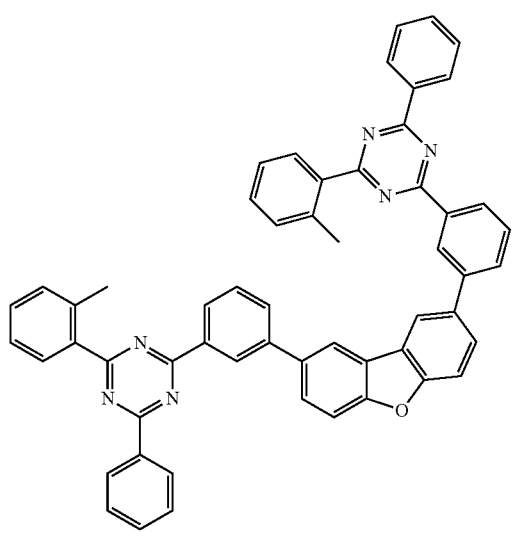
Compound 1-b-12
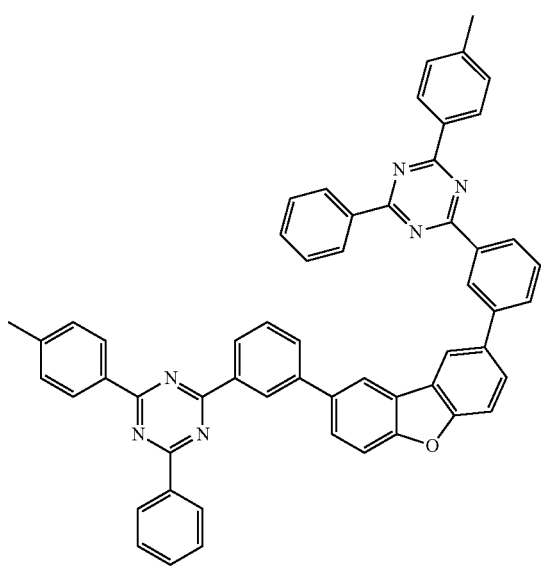

-continued
Compound 1-b-13
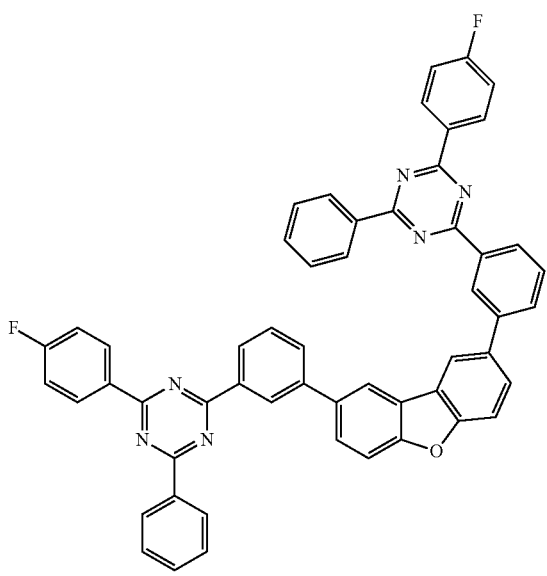
Compound 1-b-14
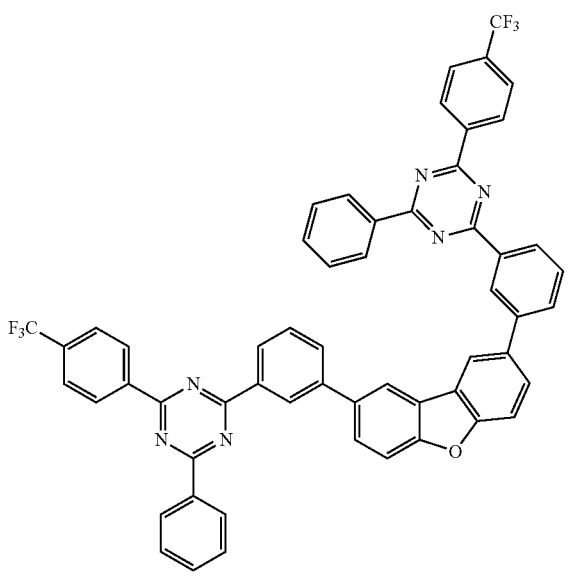
Compound 1-b-15
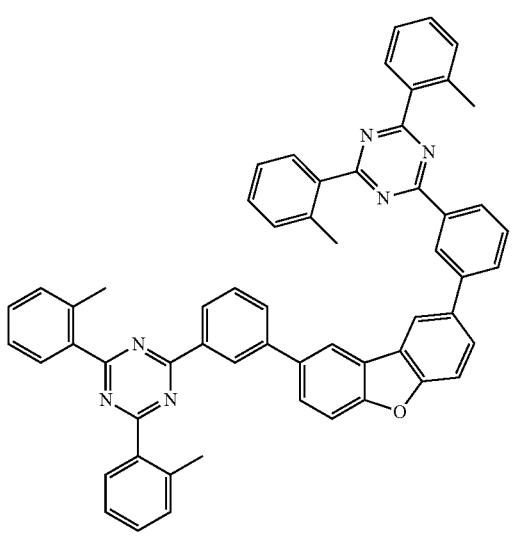
Compound 1-b-16
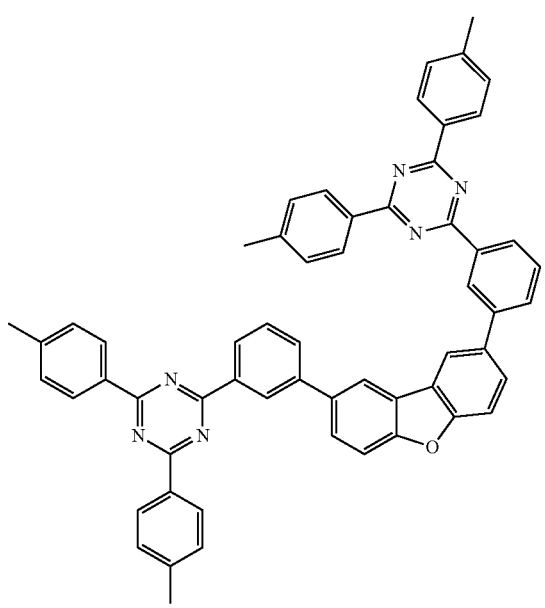
Compound 2-b-1
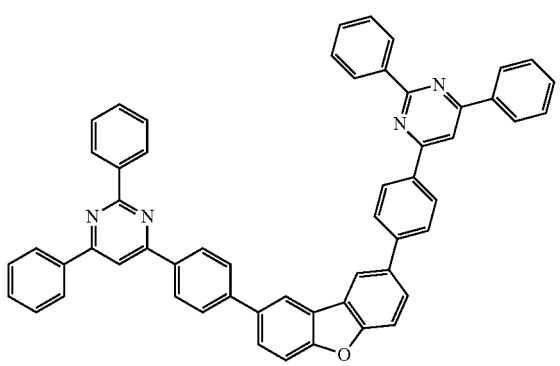
Compound 2-b-2
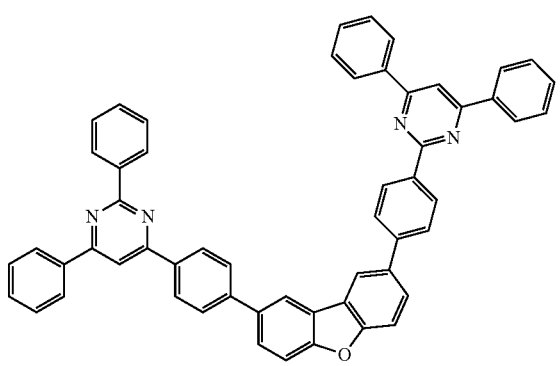

-continued
Compound 2-b-3
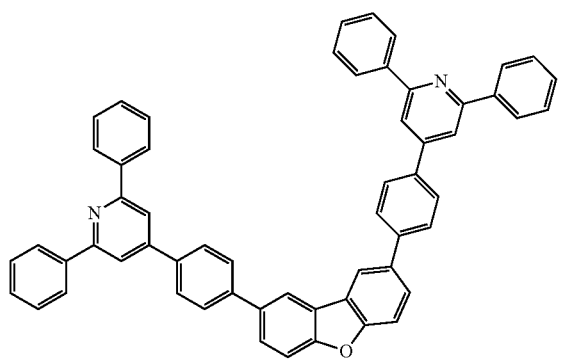
Compound 2-b-4
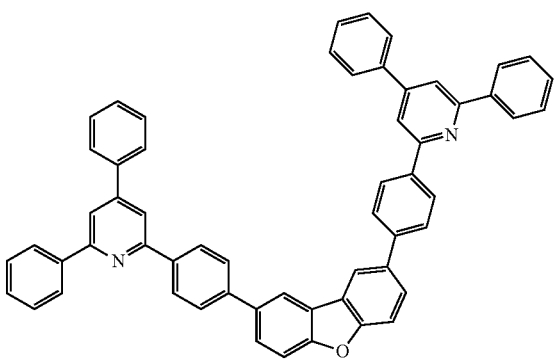
Compound 2-b-5
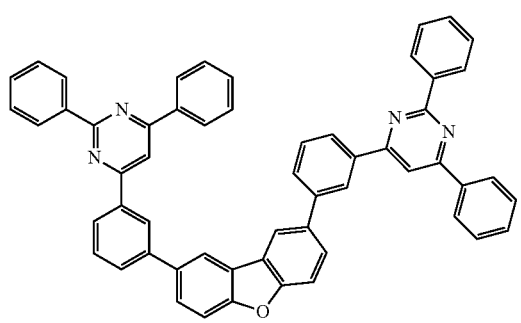
Compound 2-b-6
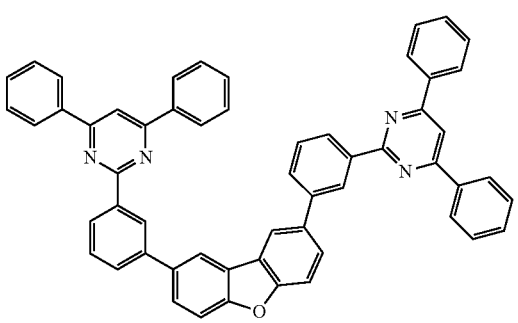
Compound 2-b-7
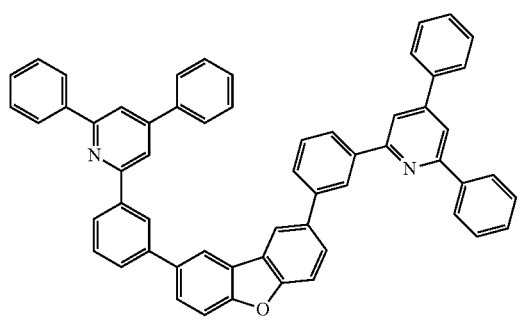
Compound 2-b-8
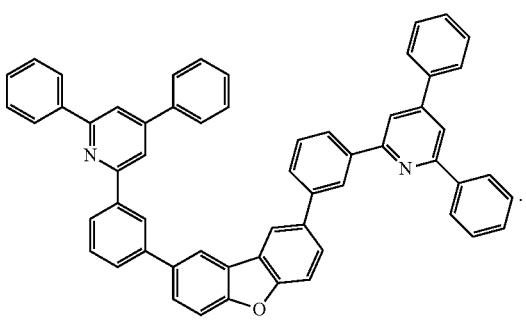
6. The heterocyclic compound of claim 1, wherein the compound represented by formula 1 is any one of the following compounds 1-c-1 to 1-c-10 and 2-c-1 to 2-c-8:
Compound 1-c-1
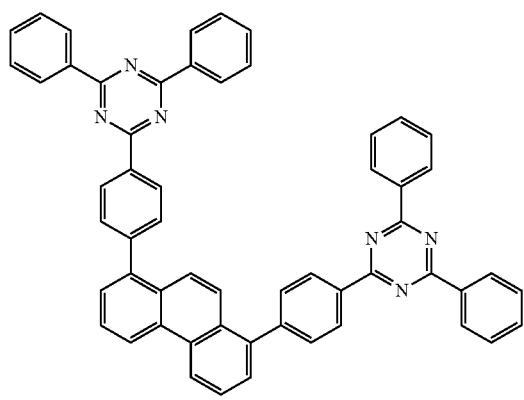
Compound 1-c-2
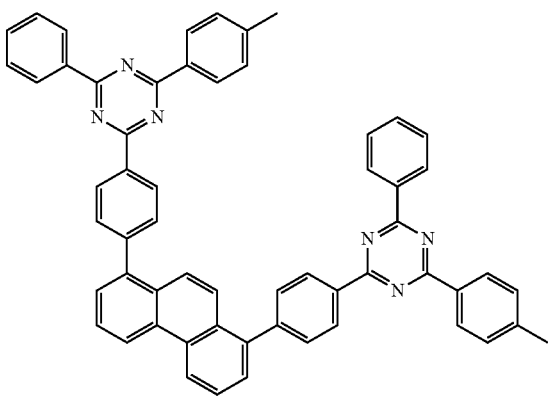

-continued
Compound 1-c-3
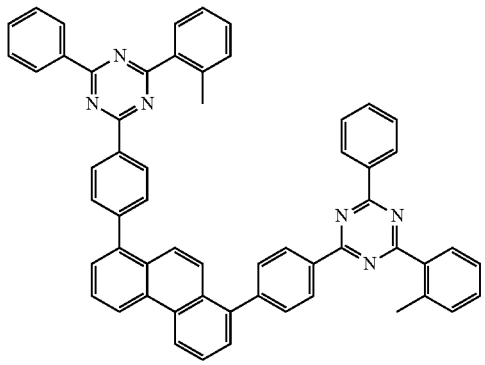
Compound 1-c-4
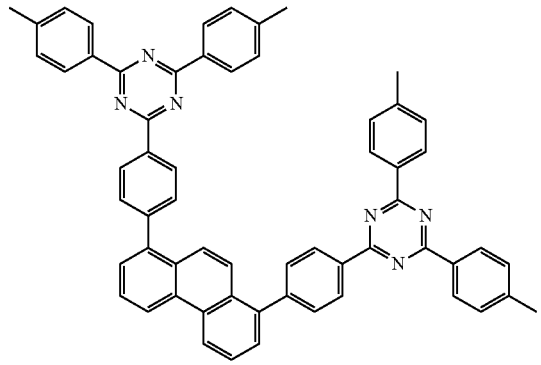
Compound 1-c-5
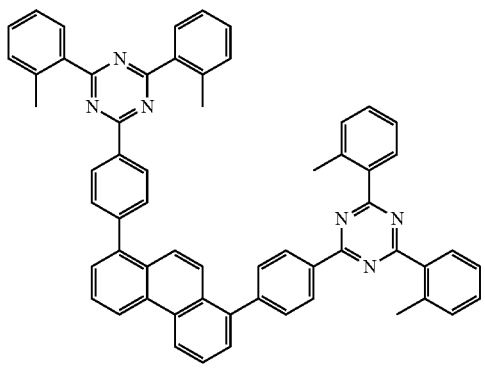
Compound 1-c-6
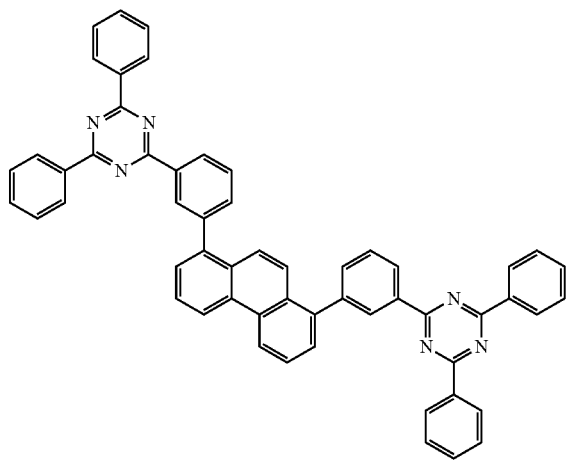
Compound 1-c-7
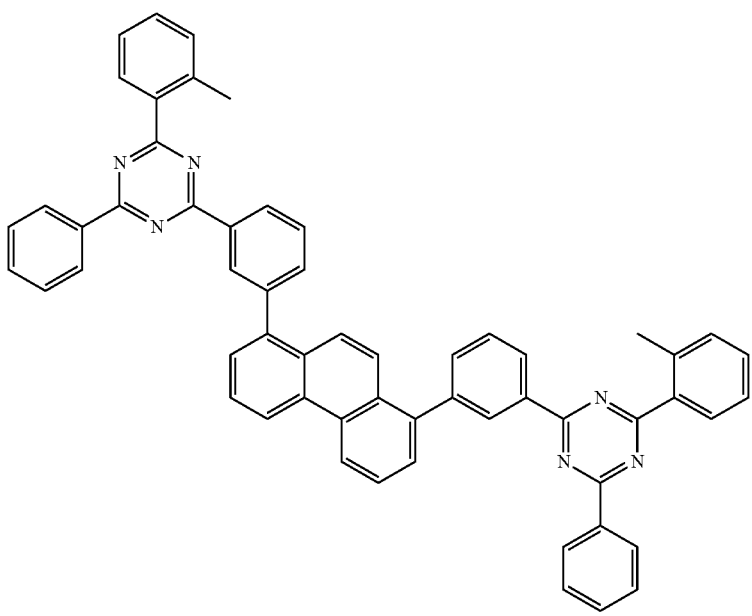

Compound 1-c-8
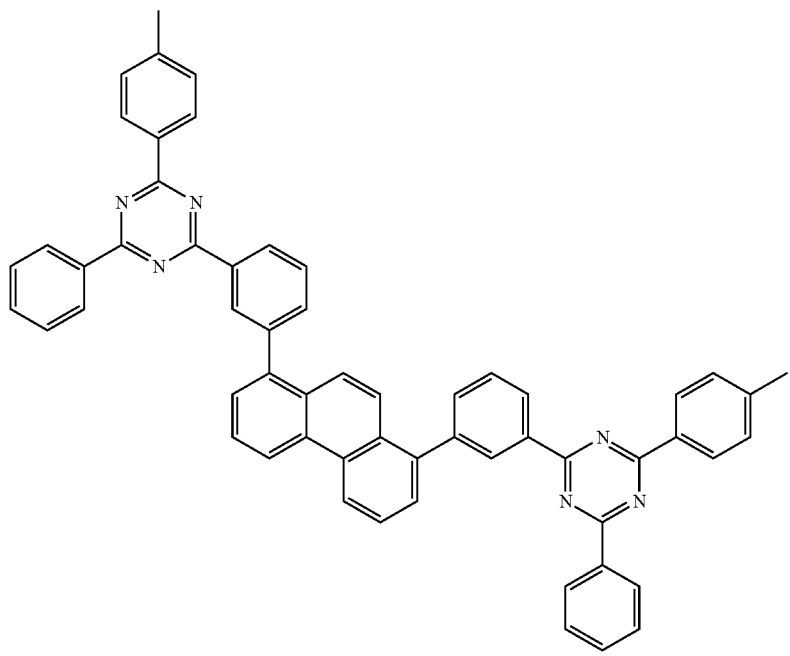
Compound-1-c-9
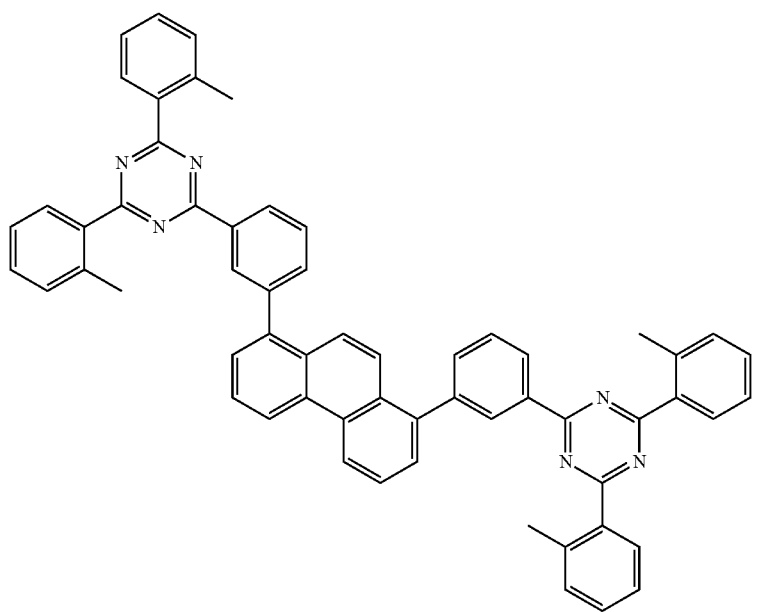

Compound-1-c-10
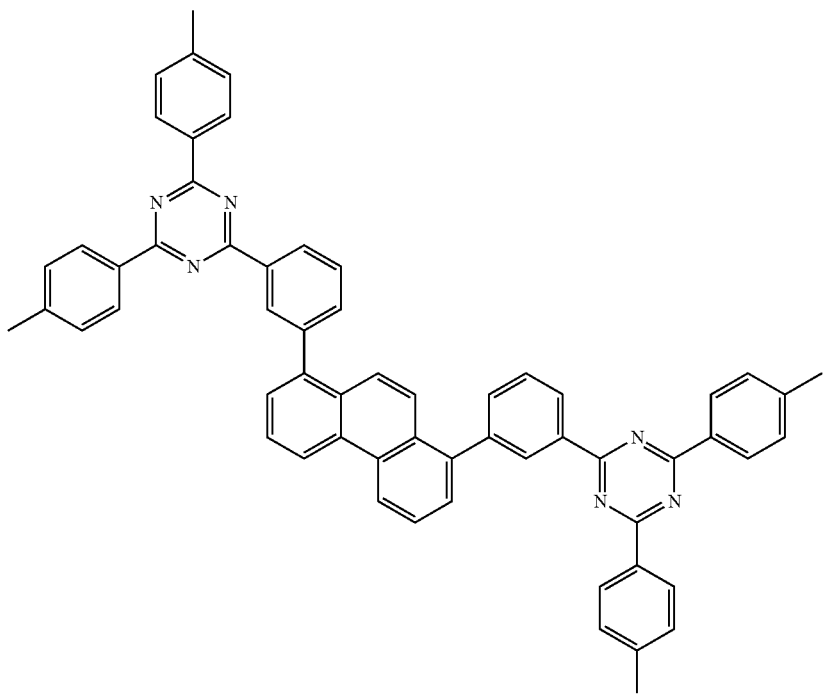
Compound 2-c-1
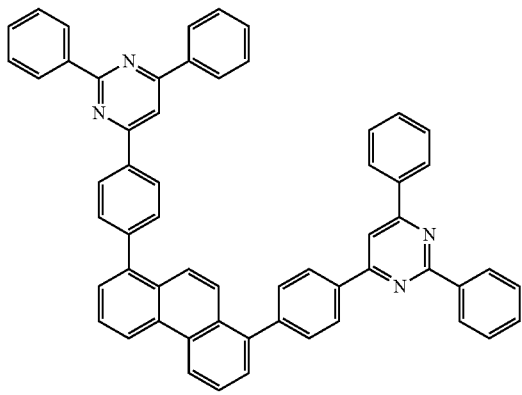
Compound 2-c-2
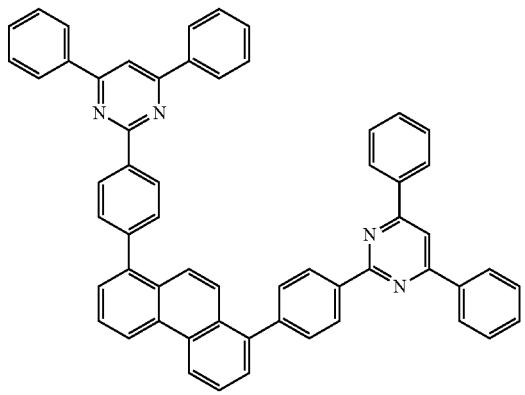
Compound 2-c-3
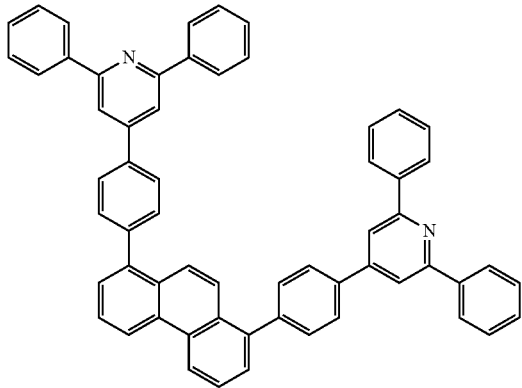
Compound 2-c-4
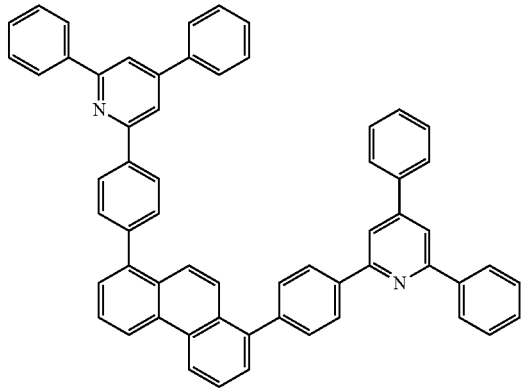

-continued
Compound 2-c-5
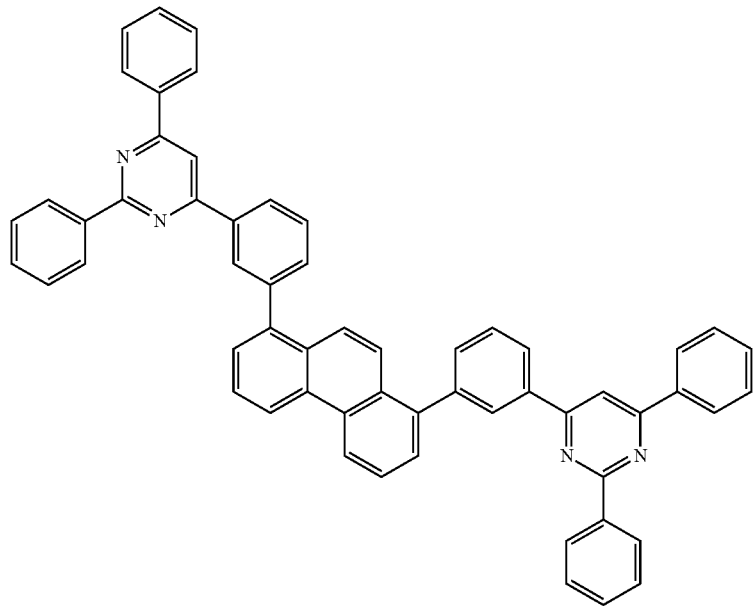
Compound 2-c-6
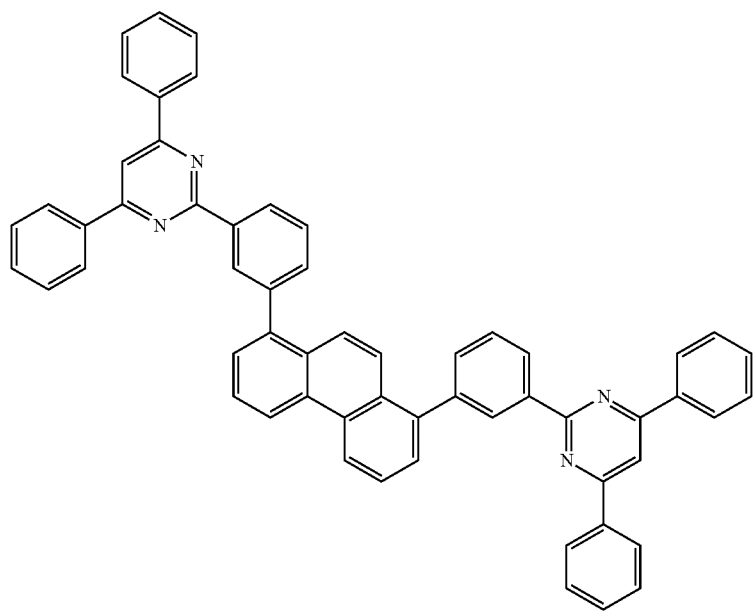

Compound 2-c-7
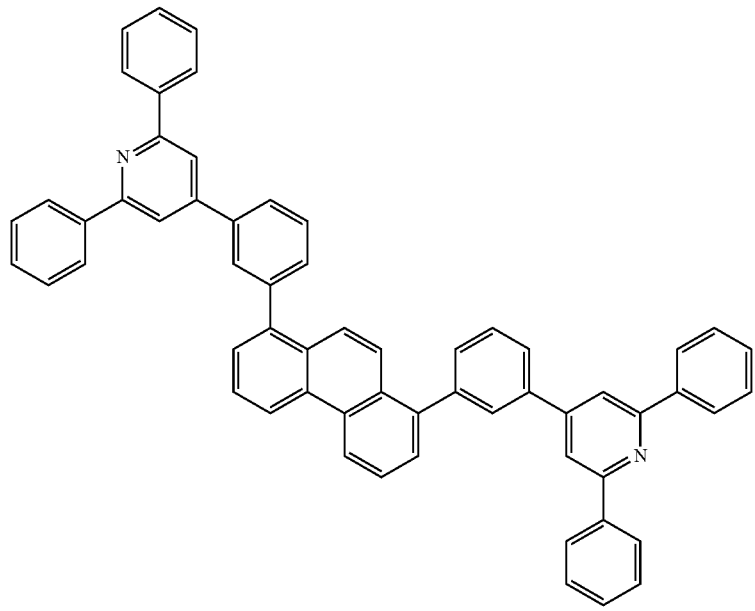
Compound 2-c-8
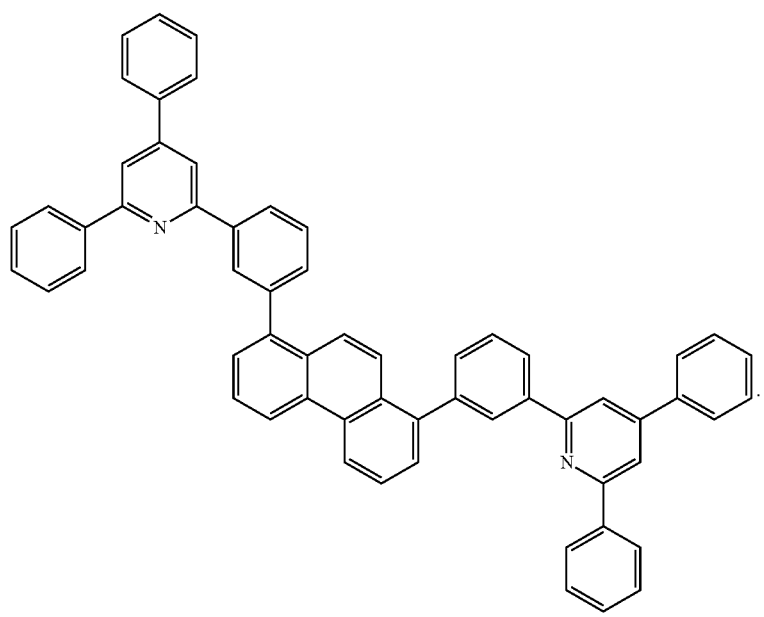

7. The heterocyclic compound of claim 1, wherein the compound represented by formula 1 is any one of the following compounds 1-d-1 to 1-d-10 and 2-d-1 to 2-d-8:
Compound 1-d-1
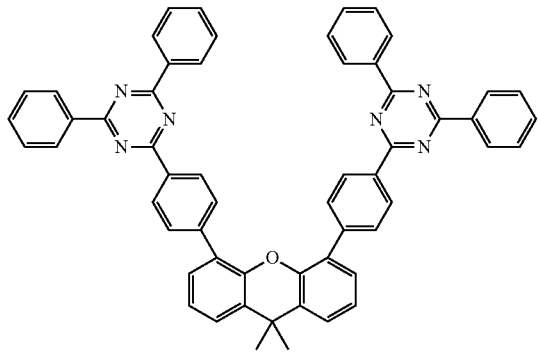
Compound 1-d-2
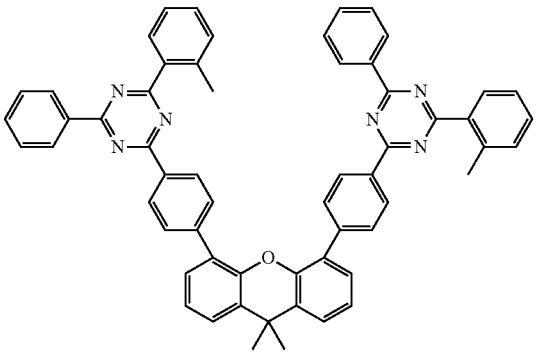
Compound 1-d-3
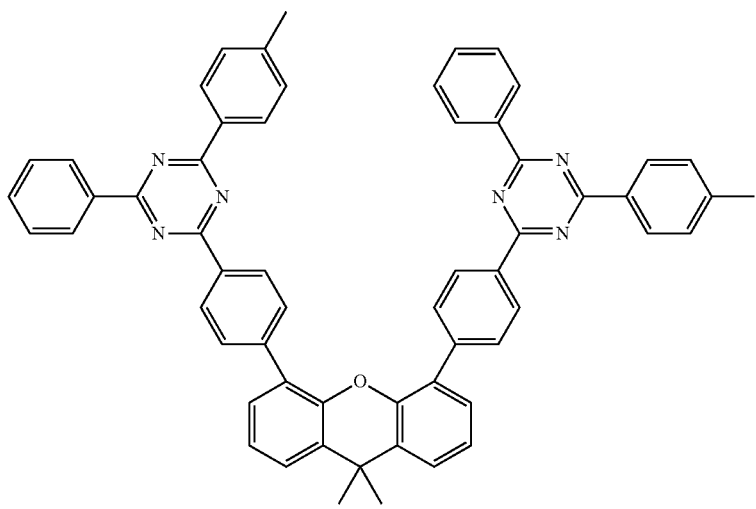
Compound 1-d-4
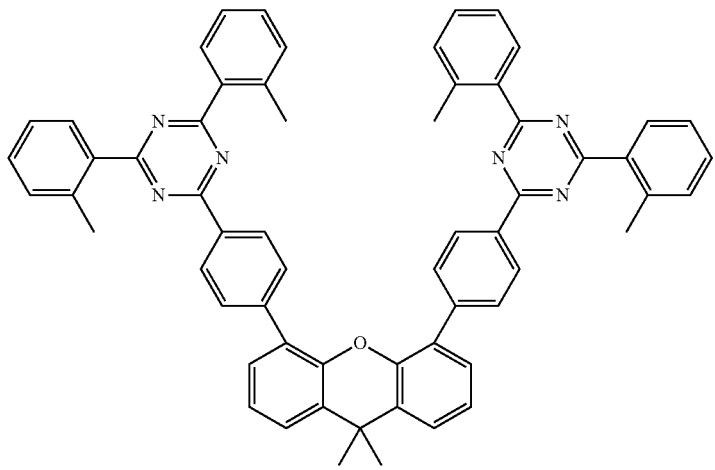

Compound 1-d-5
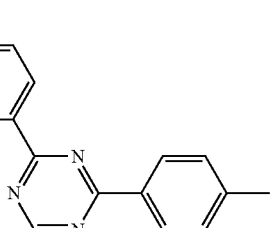
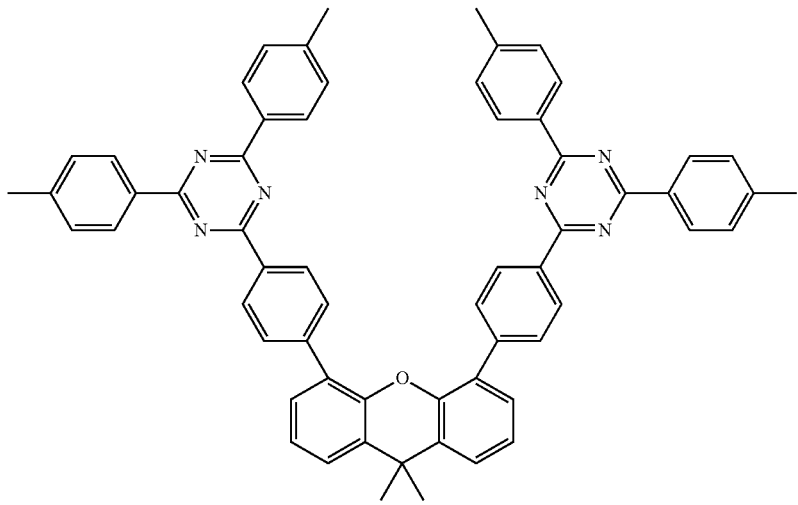
Compound 1-d-6
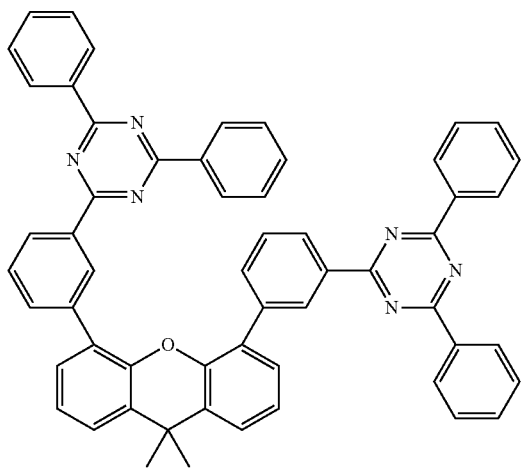
Compound 1-d-7
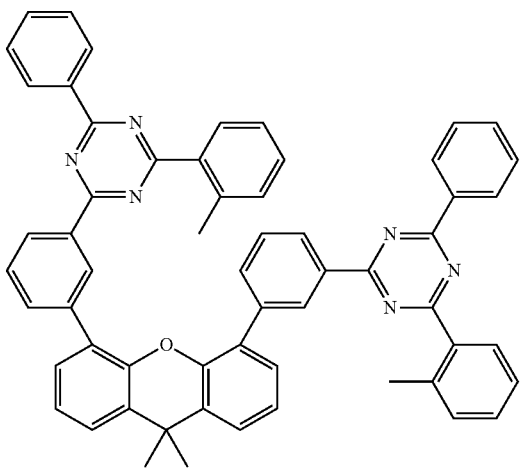
Compound 1-d-8
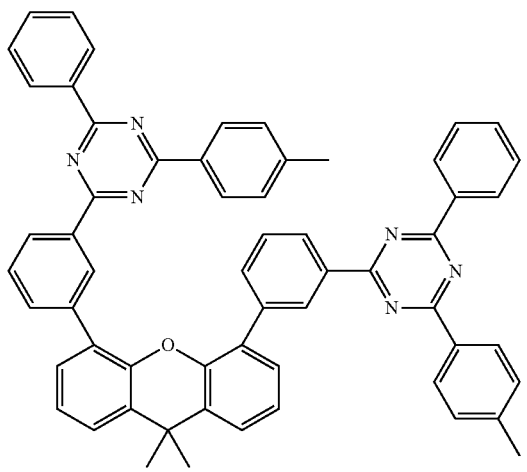
Compound 1-d-9
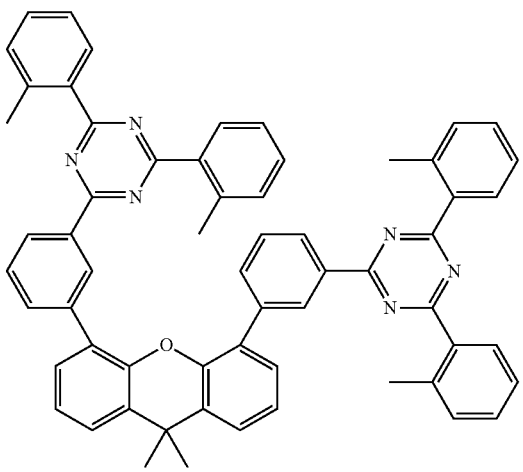

-continued
Compound 1-d-10
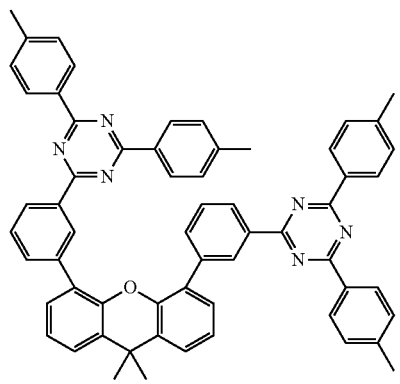
Compound 2-d-1
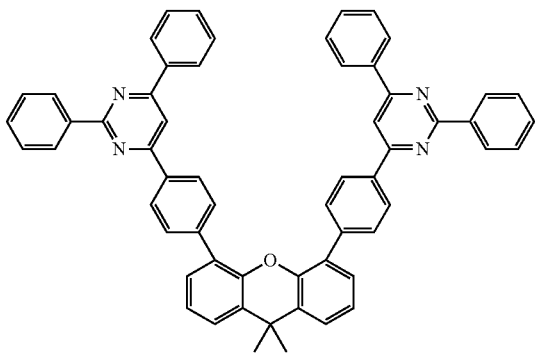
Compound 2-d-2
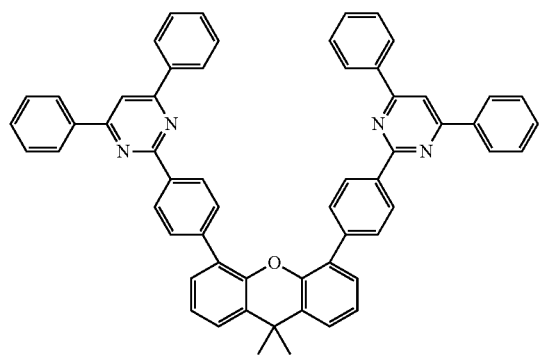
Compound 2-d-3
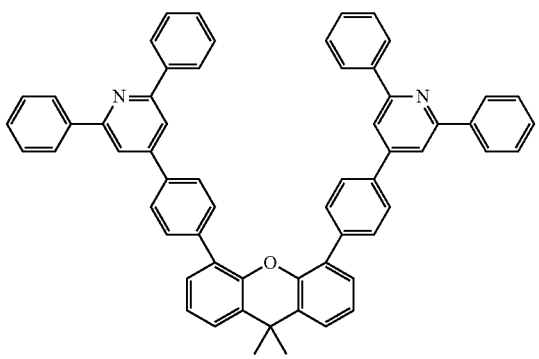
Compound 2-d-4
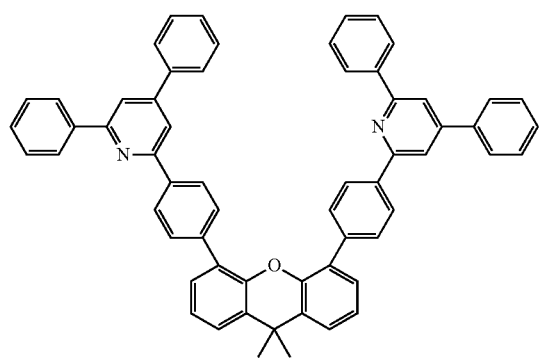
Compound 2-d-5
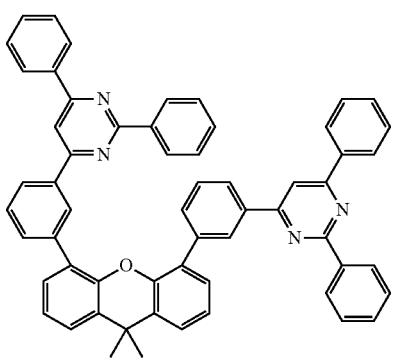
Compound 2-d-6
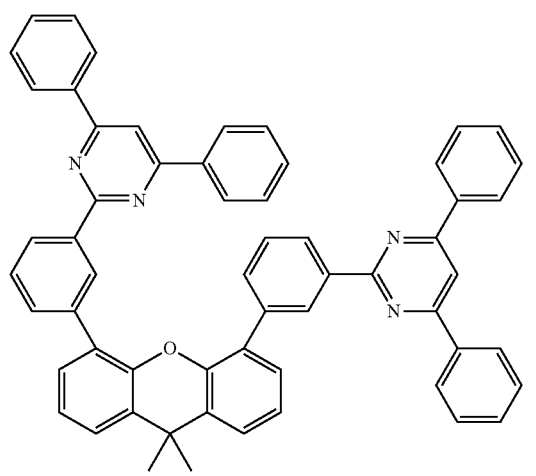
Compound 2-d-7
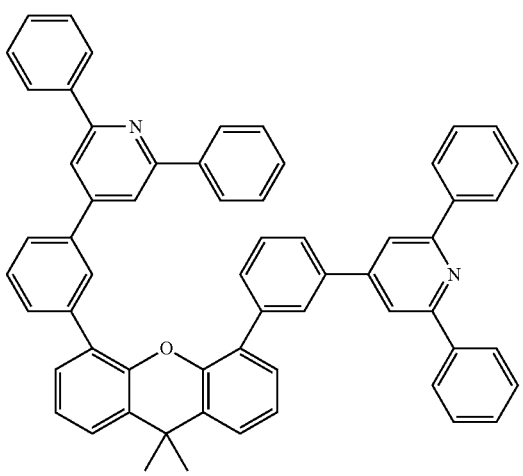

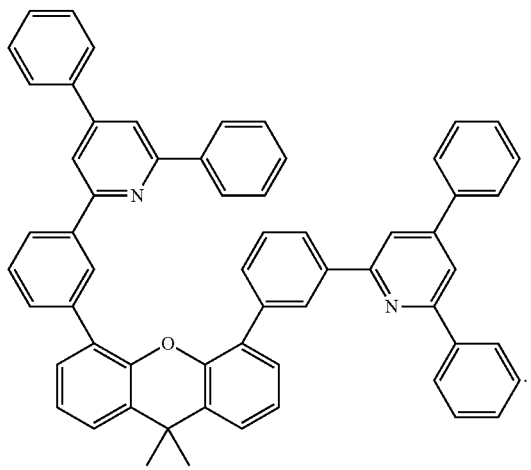
Compound 2-d-8
8. The heterocyclic compound of claim 1, wherein the compound represented by formula 1 is any one of the following compounds 1-e-1 to 1-e-10 and 2-e-1 to 2-e-8:
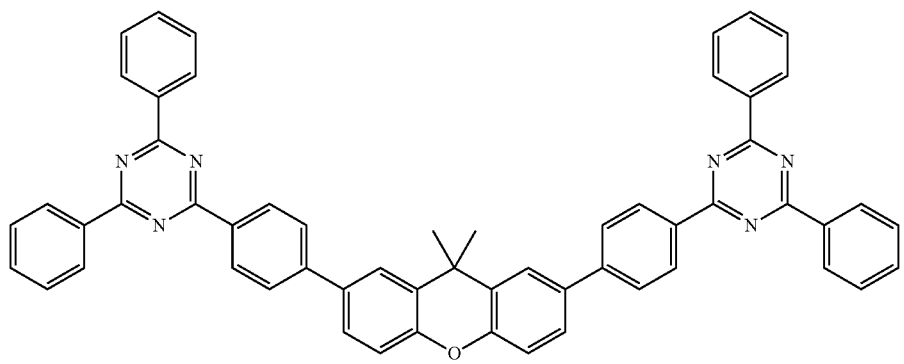
Compound 1-e-1
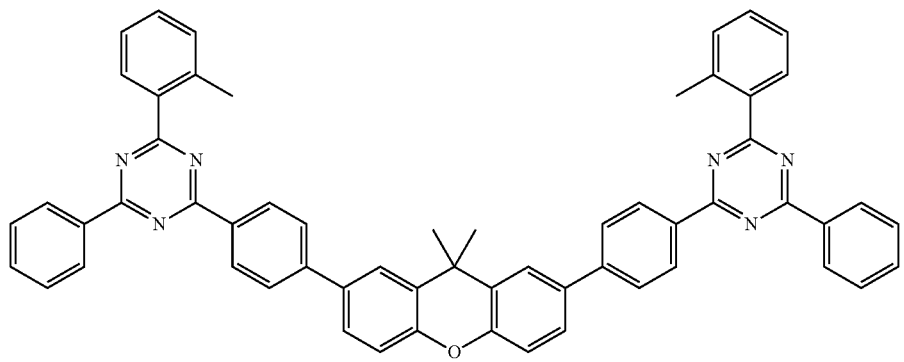
Compound 1-e-2

Compound 1-e-3
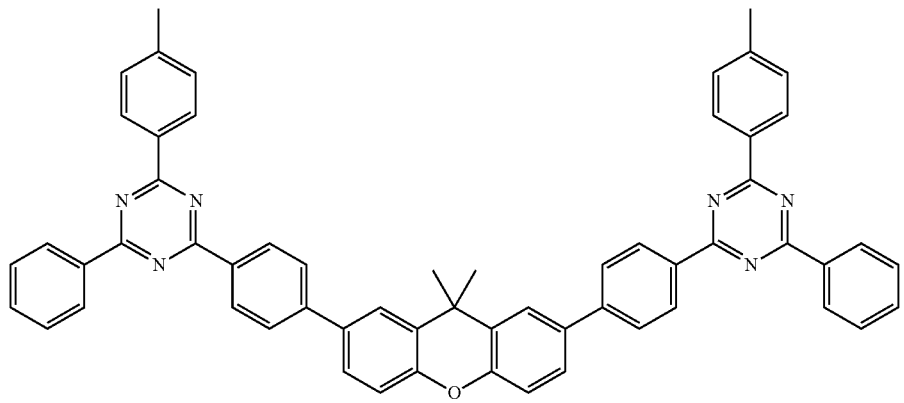
Compound 1-e-4
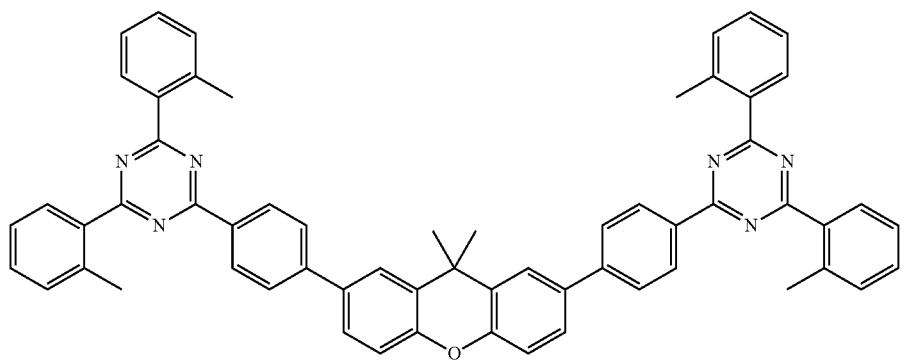
Compound 1-e-5
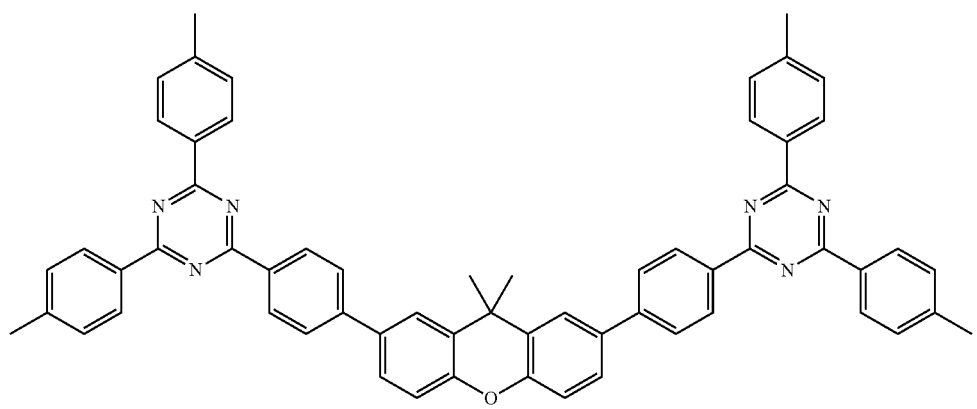
Compound 1-e-6
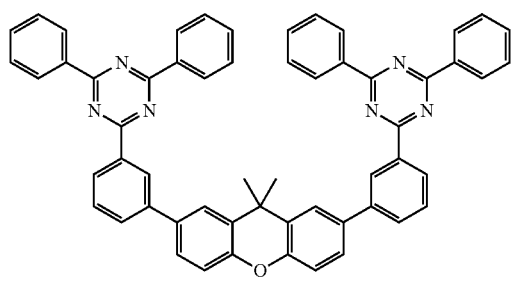
Compound 1-e-7
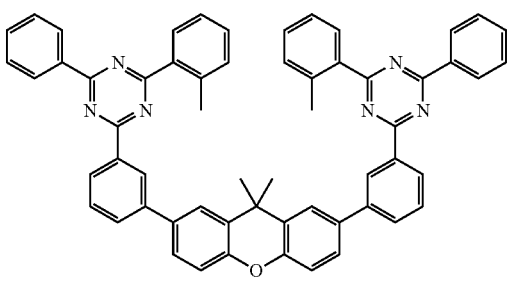

-continued
Compound 1-e-8
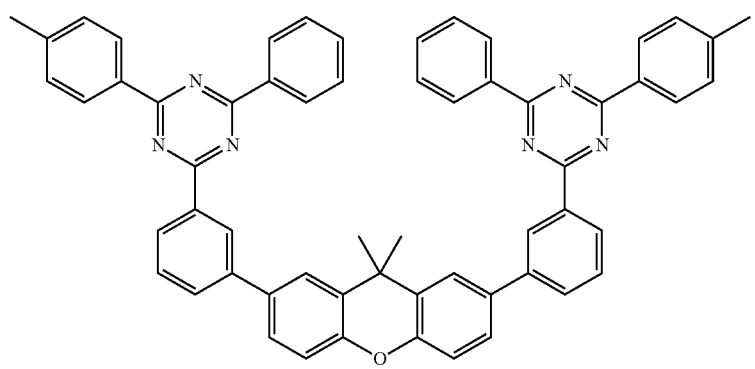
Compound 1-e-9
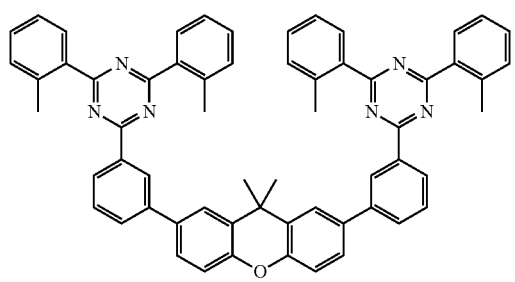
Compound 1-e-10
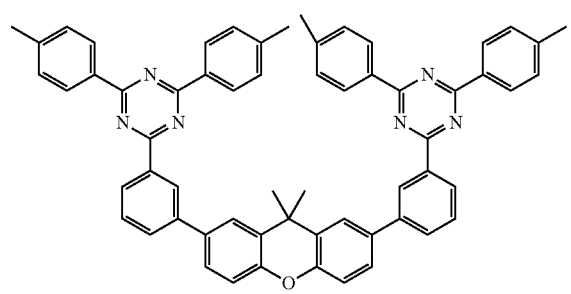
Compound 2-e-1
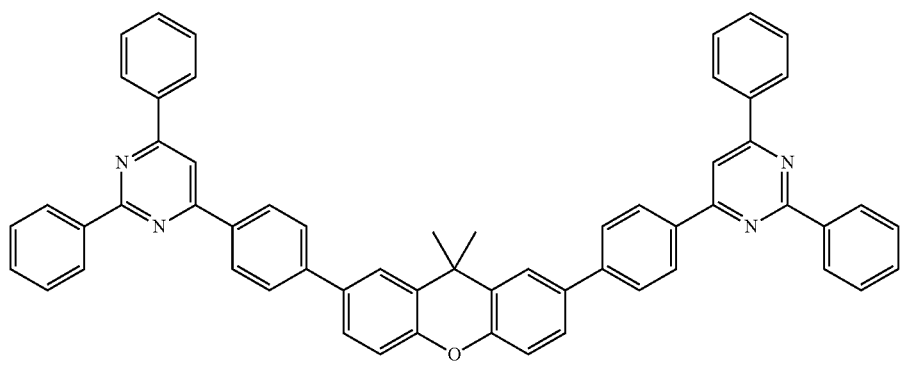
Compound 2-e-2
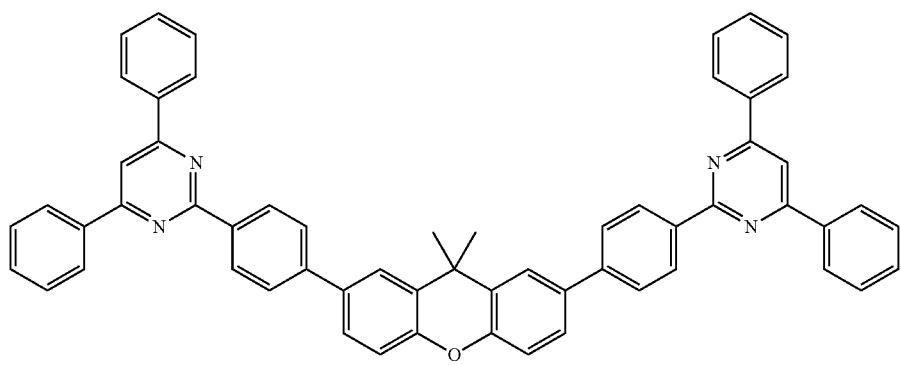

Compound 2-e-3
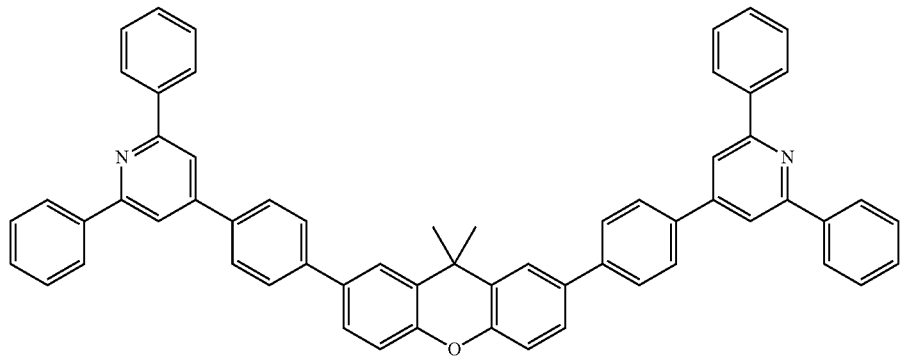
Compound 2-e-4
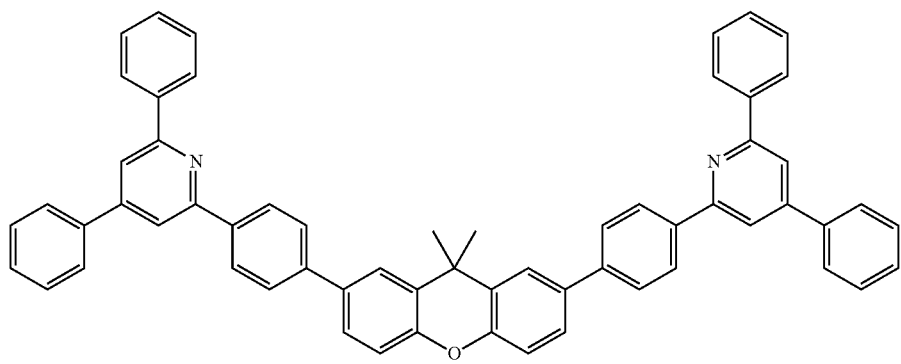
Compound 2-e-5
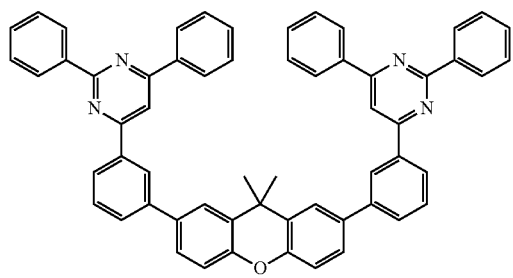
Compound 2-e-6
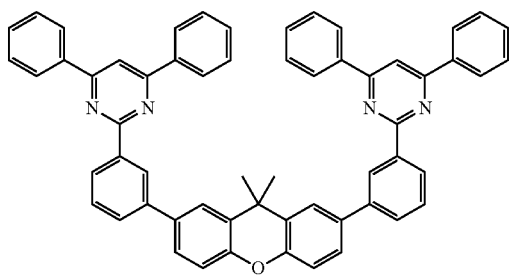
Compound 2-e-7
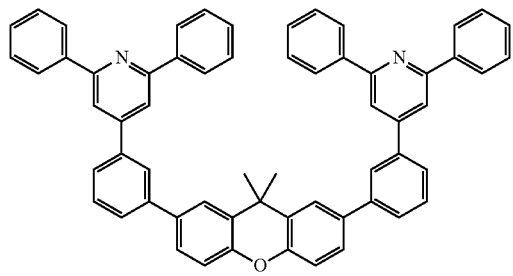
Compound 2-e-8
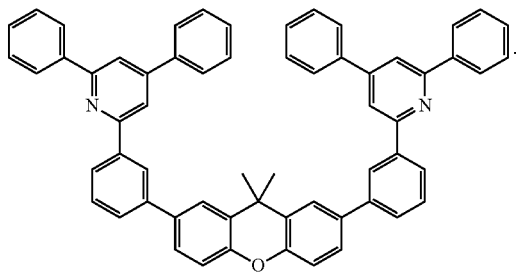

9. The heterocyclic compound of claim 1, wherein the Compound represented by formula 1 is any one of the following compounds 1-f-1 to 1-f-10 and 2-f-1 to 2-f-8:
Compound 1-f-1
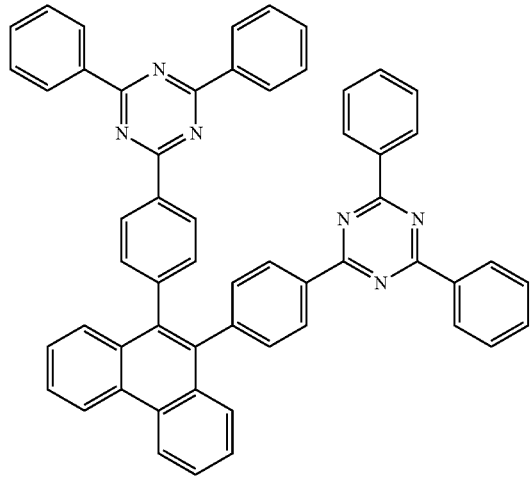
Compound 1-f-2
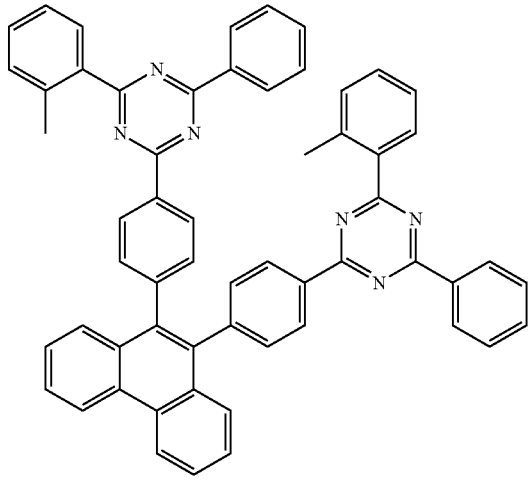
Compound 1-f-3
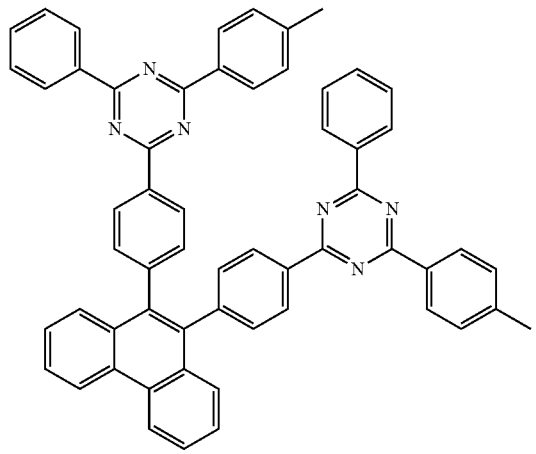
Compound 1-f-4
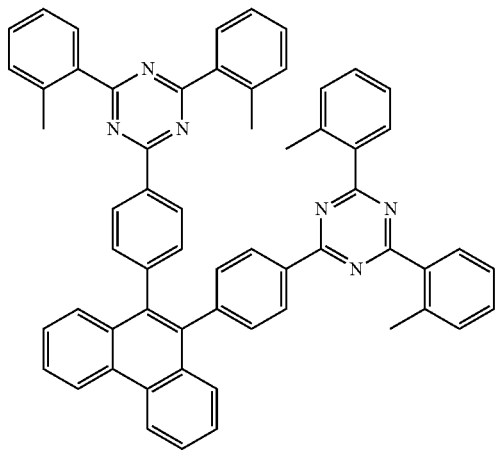
Compound 1-f-5
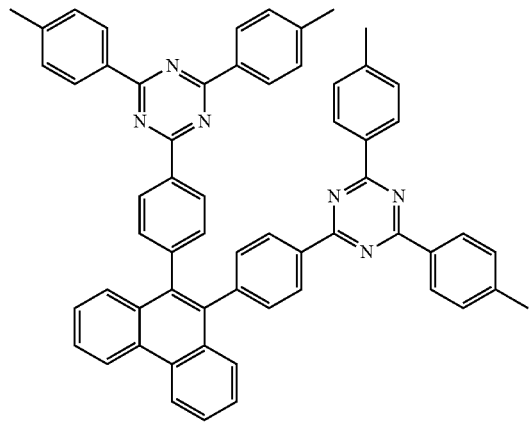
Compound 1-f-6
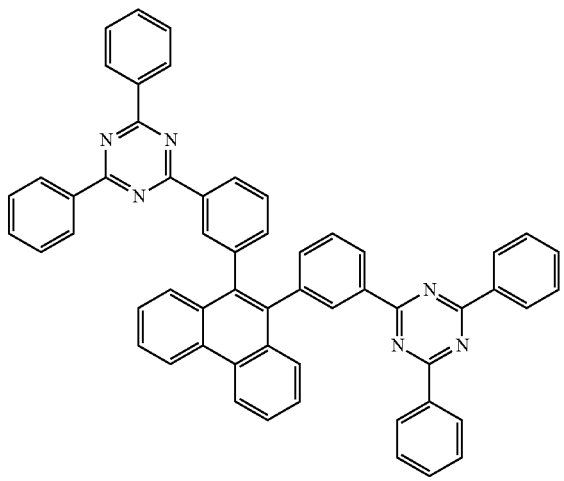

-continued
Compound 1-f-7
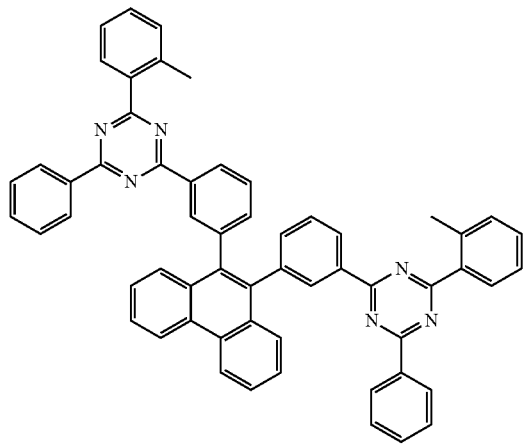
Compound 1-f-8
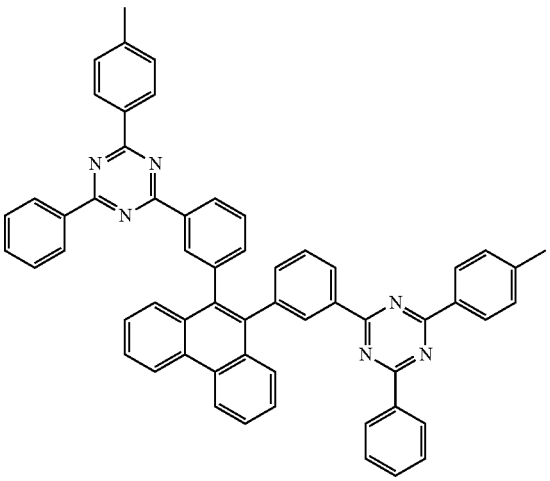
Compound 1-f-9
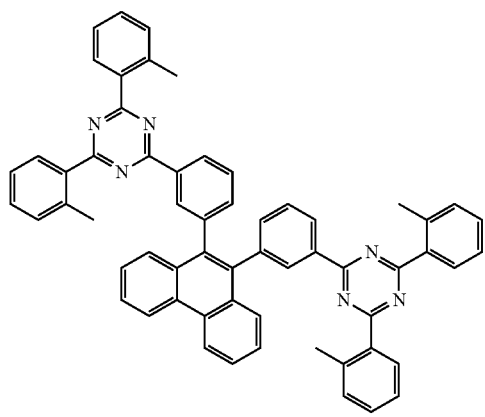
Compound 1-f-10
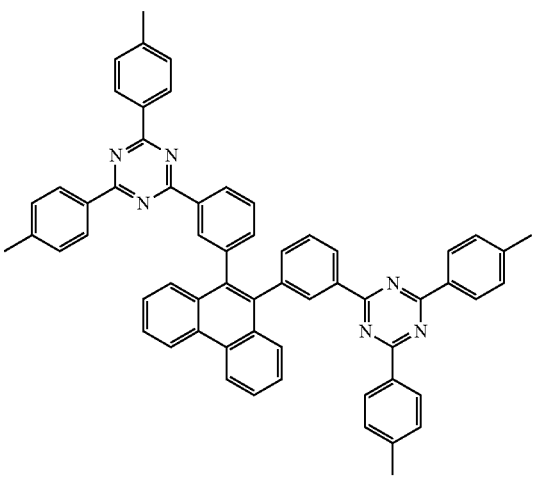
Compound 2-f-1
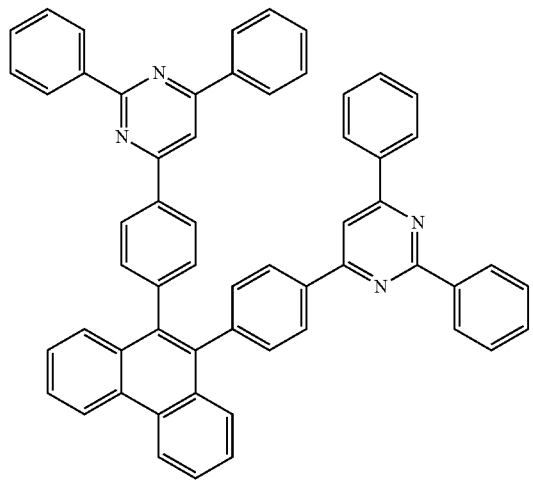
Compound 2-f-2
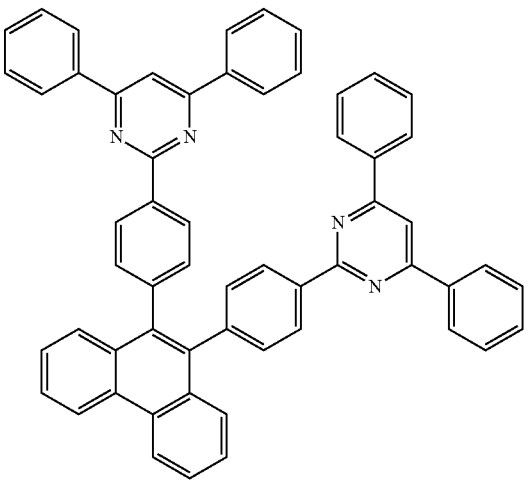

-continued
Compound 2-f-3
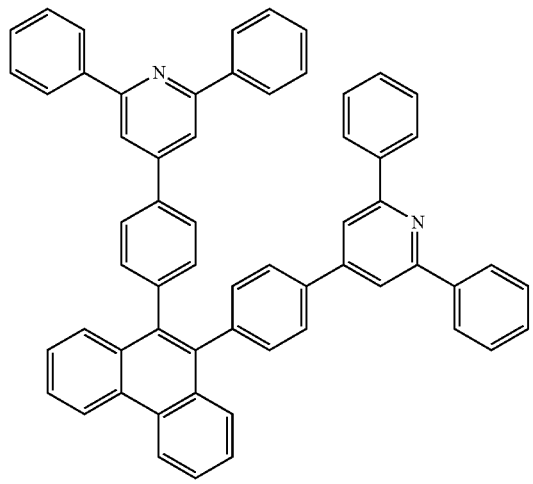
Compound 2-f-4
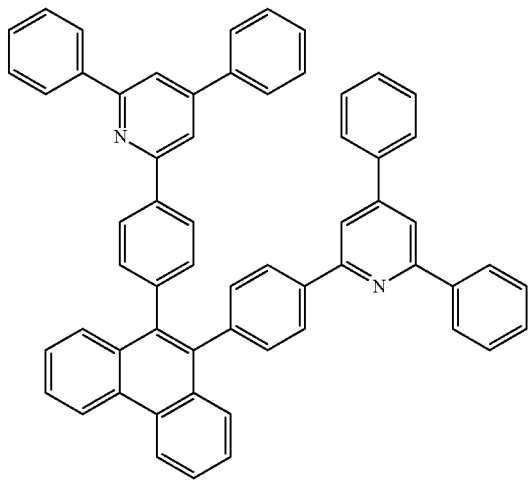
Compound 2-f-5
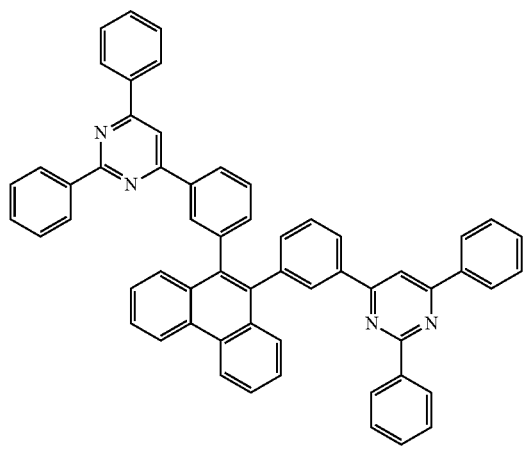
Compound 2-f-6
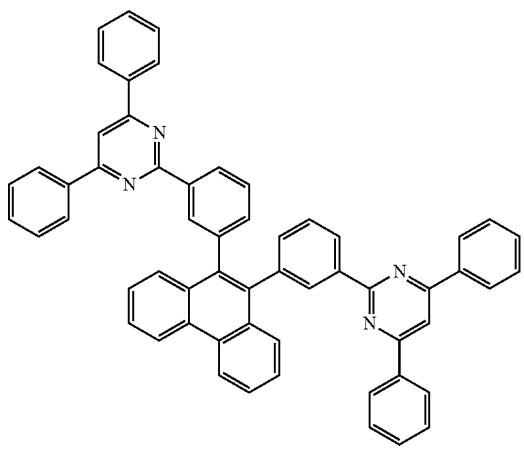
Compound 2-f-7
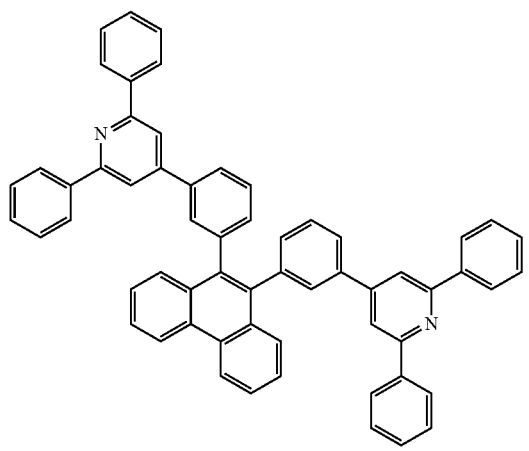
Compound 2-f-8
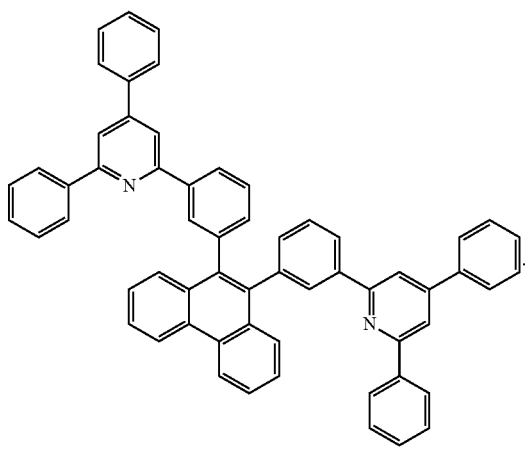

10. An organic electronic device comprising a first electrode, a second electrode and one or more organic material layers interposed between the first electrode and the second electrode, wherein the organic material layers comprises a hole-injecting layer, a hole-transporting layer, an electron-transporting layer, or a charge-generating layer, and wherein one or more of the hole-injecting layer, hole-transporting layer, electron-transporting layer, and charge-generating layer comprise the heterocyclic compound of claim 1.

11. The organic electronic device of claim 10, wherein the organic electronic device is selected from the group consisting of an organic light-emitting device, an organic solar cell and an organic transistor.

12. The organic electronic device of claim 10, wherein the organic electronic device is an organic light-emitting device comprising the first electrode, the second electrode and one or more organic material layers interposed between the first electrode and the second electrode.

13. The organic electronic device of claim 12, wherein the organic material layers include a hole-injecting layer or a hole-transporting layer, which comprises the heterocyclic compound.

14. The organic electronic device of claim 12, wherein the organic material layers include an electron-transporting layer comprising the heterocyclic compound.

15. The organic electronic device of claim 12, wherein the organic material layers include, in addition to the organic material layers comprising the heterocyclic compound, a hole-injecting layer or a hole-transporting layer including the compound which comprises an arylamino, carbazole or benzcarbazole group.

16. The organic electronic device of claim 12, wherein the organic material layers comprising the heterocyclic compound comprise the heterocyclic compound as a host and comprise another organic compound, a metal or a metal compound as a dopant.

17. The organic electronic device of claim 10, wherein the organic electronic device is an organic solar cell comprising the first electrode, the second electrode and one or more organic material layers, interposed between the first electrode and the second electrode.

18. The organic electronic device of claim 10, wherein the organic electronic device is an organic transistor comprising a source, a drain, a gate and one or more organic material layers.

* * * * *